(12) United States Patent
Pulé et al.

(10) Patent No.: US 11,345,734 B2
(45) Date of Patent: May 31, 2022

(54) CHIMERIC T CELL

(71) Applicant: AUTOLUS LIMITED, London (GB)

(72) Inventors: Martin Pulé, London (GB); Shaun Cordoba, London (GB); Simon Thomas, London (GB); Khai Kong, London (GB)

(73) Assignee: AUTOLUS LIMITED, London (GB)

( * ) Notice: Subject to any disclaimer, the term of this patent is extended or adjusted under 35 U.S.C. 154(b) by 0 days.

(21) Appl. No.: 15/577,378

(22) PCT Filed: May 31, 2016

(86) PCT No.: PCT/GB2016/051576
§ 371 (c)(1),
(2) Date: Nov. 28, 2017

(87) PCT Pub. No.: WO2016/193696
PCT Pub. Date: Dec. 8, 2016

(65) Prior Publication Data
US 2019/0023761 A1    Jan. 24, 2019

(30) Foreign Application Priority Data
Jun. 1, 2015    (GB) .................................. 1509413.9

(51) Int. Cl.
| | |
|---|---|
| C12N 5/0783 | (2010.01) |
| C07K 14/725 | (2006.01) |
| A61K 39/00 | (2006.01) |
| A61P 35/00 | (2006.01) |
| C07K 16/28 | (2006.01) |
| C12N 15/867 | (2006.01) |

(52) U.S. Cl.
CPC .......... *C07K 14/7051* (2013.01); *A61P 35/00* (2018.01); *C07K 16/2803* (2013.01); *C07K 16/2809* (2013.01); *C07K 16/2815* (2013.01); *C07K 16/2818* (2013.01); *C12N 5/0636* (2013.01); *C12N 15/867* (2013.01); *A61K 2039/5156* (2013.01); *A61K 2039/5158* (2013.01); *C07K 2317/622* (2013.01); *C07K 2319/02* (2013.01); *C07K 2319/033* (2013.01); *C12N 2501/998* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 6,004,811 A | 12/1999 | Seed et al. | |
| 7,052,906 B1 | 5/2006 | Lawson et al. | |
| 2002/0197606 A1 | 12/2002 | Craig | |
| 2015/0376296 A1* | 12/2015 | Fedorov | A61K 35/17 424/93.71 |

FOREIGN PATENT DOCUMENTS

| | | |
|---|---|---|
| WO | WO-96/40199 A1 | 12/1996 |
| WO | WO-97/31113 A1 | 8/1997 |
| WO | WO-2015/075468 A1 | 5/2015 |
| WO | WO-2015/075469 A1 | 5/2015 |
| WO | WO-2015/075470 A1 | 5/2015 |
| WO | WO-2018/096361 A1 | 5/2018 |
| WO | WO-2020/183131 A1 | 9/2020 |

OTHER PUBLICATIONS

Northrop et al, (Molecular and Cellular Biology, 16(5): 2255-2263, 1996) (Year: 1996).*
Lorenz et al, Immunol Rev, 228(1): 342-359, 2009 (Year: 2009).*
Odorizzi (J Immunol, 188: 2957-2965, 2012 (Year: 2012).*
Anselmi (J. Chem. Inf. Model, 60: 3157-3171, 2020) (Year: 2010).*
Yaffe (Nature Reviews, Molecular Biology, 31: 177-186, 2002 (Year: 2002).*
Bunda et al., Inhibition of SHP2-mediated dephosphorylation of Ras suppresses oncogenesis, *Nature Communications*, 6:8859 (2015).
Isakov et al., ZAP-70 binding specificity to T cell receptor tyrosine-based activation motifs: the tandem SH2 domains of ZAP-70 bind distinct tyrosine-based activation motifs with varying affinity, *J. Exp. Med.*, 181:375-80 (1995).
Kim et al., Synergistic inhibition of T-cell activation by a cell-permeable ZAP-70 mutant and ctCTLA-4, *Biochem. Biphys. Res. Comm.*, 381:355-60 (2009).
Wange et al., Tandem SH2 domains of ZAP-70 bind to T cell antigen receptor zeta and CD3 epsilon from activated Jurkat T cells, *J Biol Chem.*, 268 (26):19797-801 (1993).
Yamasaki et al., The kinase, SH3 and SH2 domains of Lck play critical roles in T-cell activation after ZAP-70 membrane localization, *Mol Cell Biol.*, 1(16):7151-7160 (1996).
Liu et al., "A Chimeric Switch-Receptor Targeting PD1 Augments the Efficacy of Second-Generation CAR T Cells in Advanced Solid Tumors," *Cancer Res.*, 76(6):1578-1590 (2016).

(Continued)

*Primary Examiner* — Anoop K Singh
*Assistant Examiner* — Magdalene K Sgagias
(74) *Attorney, Agent, or Firm* — Marshall, Gerstein & Borun LLP

(57) ABSTRACT

The present invention relates to a cell which comprises a chimeric antigen receptor (CAR) and a signal transduction modifying protein, selected from one of the following: (i) a truncated protein which comprises an SH2 domain from a protein which binds a phosphorylated immunoreceptor tyrosine-based activation motif (ITAM), but lacks a kinase domain; (ii) a truncated protein which comprises an SH2 domain from a protein which binds a phosphorylated immunoreceptor tyrosine-based inhibition motif (ITIM) but lacks a phosphatase domain; (iii) a fusion protein which comprises (a) an SH2 domain from a protein which binds a phosphorylated immunoreceptor tyrosine-based activation motif (ITAM) or from a protein which binds a phosphorylated immunoreceptor tyrosine-based inhibition motif (ITIM); and (ii) a heterologous domain.

5 Claims, 23 Drawing Sheets

Specification includes a Sequence Listing.

(56) References Cited

OTHER PUBLICATIONS

Menger et al., "TALEN-Mediated Inactivation of PD-1 in Tumor-Reactive Lymphocytes Promotes Intratumoral T-cell Persistence and Rejection of Established Tumors," Cancer Res., 76(8):2087-2093 (2016).
Northrop et al., "Characterization of the roles of SH2 domain-containing proteins in T-lymphocyte activation by using dominant negative SH2 domains," Mol Cell Biol., 16(5):2255-2263 (1996).
Odorizzi et al., "Inhibitory Receptors on Lymphocytes: Insights from Infections," J. Immunol., 188(7):2957/2965 (2012).
International Search Report and Written Opinion from corresponding International Application No. PCT/GB2016/051576 dated Sep. 21, 2016.
Liu et al., "A Comprehensive Immunoreceptor Phosphotyrosine-based Signaling Network Revealed by Reciprocal Protein-Peptide Array Screening," Molecular & Cell Proteomics 14.7:1846-1858 (2015).
Stanford et al., "Regulation of TCR Signalling by tyrosine phosphatases: from immune homeostasis to autoimmunity," Immunology 137(1):19 pages (2012).
Baba et al., "Dual regulation of BCR-mediated growth inhibition signaling by CD72," Eur. J. Immunol. 35:1634-1642 (2005).
Baldan et al., "A Dominant Negative 8HP-2 Which Abrogates PD-1 Sgnalling Pathways and Restores Function of Cytotoxic CART Cells," Blood 130:3190 (2017).
Chen et al., "CAR T-cell intrinsic PD-1 checkpoint blockade: A two-in-one approach for solid tumor immunotherapy," OncoImmunology 4 pages (2017).
John et al., "Blockade of PD-1 immunosuppression boosts CART-cell therapy," OncoImmunology 2(10):e26286-1, 4 pages (2013).
Dong et al., "Tumor-associated B7-H1 promotes T-cell apoptosis: A potential mechanism of immune evasion," Nature Medicine 8(8):793-800 (2002).
Hirano et al., "Blockade of B7-H1 and PD-1 by Monoclonal Antibodies Potentiates Cancer Therapeutic Immunity," Cancer Res 65(3):1089-1096 (2005).
Moon et al., "Multifactorial T-cell Hypofunction That is Reversible Can Limit the Efficacy of Chimeric Antigen Receptor-Transduced Human T cells in Solid Tumors," Clin Cancer Res 20(16):4262-4273 (2014).
Tamada et al., "Redirecting Gene-Modified T Cells toward Various Cancer Types Using Tagged Antibodies," Clin Cancer Res 18(23):6436-6445 (2012).
David et al., "The SH2 Domain-containing Tyrosine Phosphatase PTP1D Is Required for Interferon $\alpha/\beta$-induced Gene Expression," The Journal of Biological Chemistry 271(27):15862-15865 (1996).
Wang et al., "Specificity of the SH2 Domains of SHP-1 in the Interaction with the Immunoreceptor Tyrosine-Based Inhibitory Motif-Bearing Receptor gp49B," The Journal of Immunology, 1318-1323 (1999).
Collection of research reports of the Uehara Memorial Foundation, vol. 28, pp. 1-4, Dec. 5, 2014 (Including an English language translation).
Roitt et al., "Immunology", Publishing House "Mir", pp. 4-6 (2000). (Including an English language translation).
Stebbins et al., "Vav1 Dephosphorylation by the Tyrosine Phosphatase SHP-1 as a Mechanism for Inhibition of Cellular Cytotoxicity," Molecular and Cellular Biology, 23(17):6291-6299 (2003).

* cited by examiner

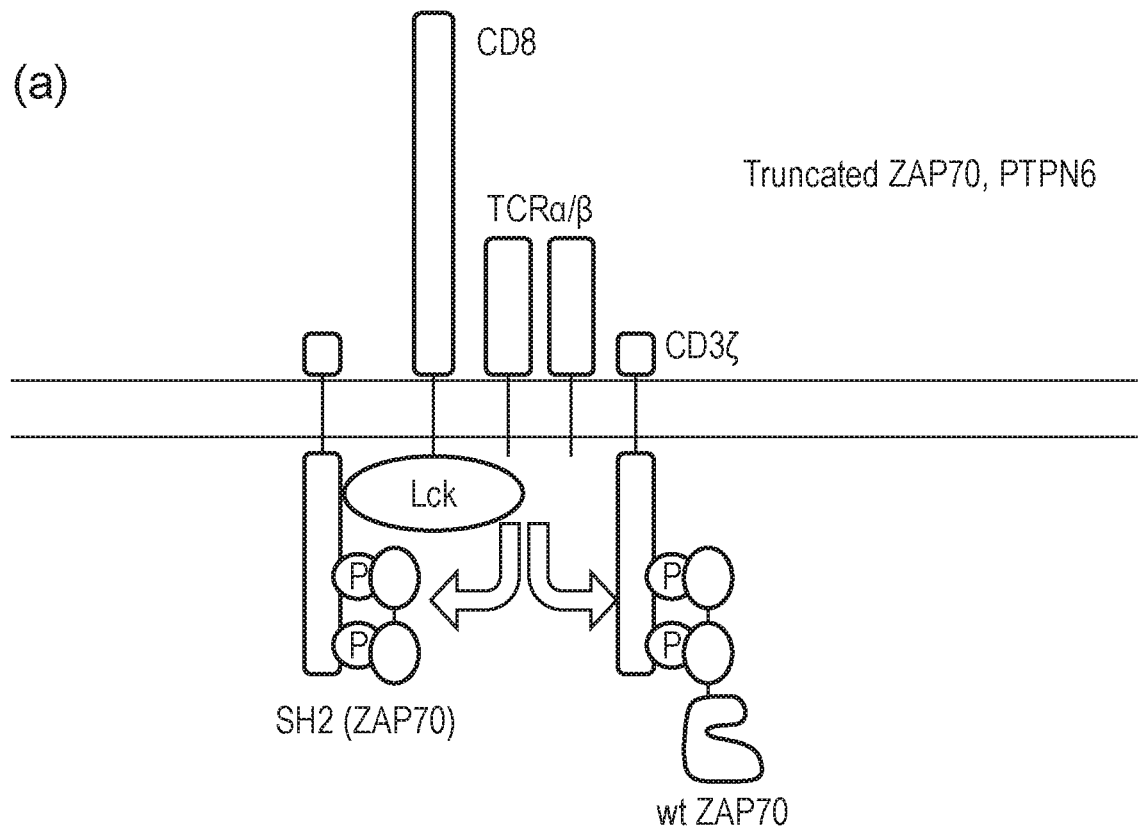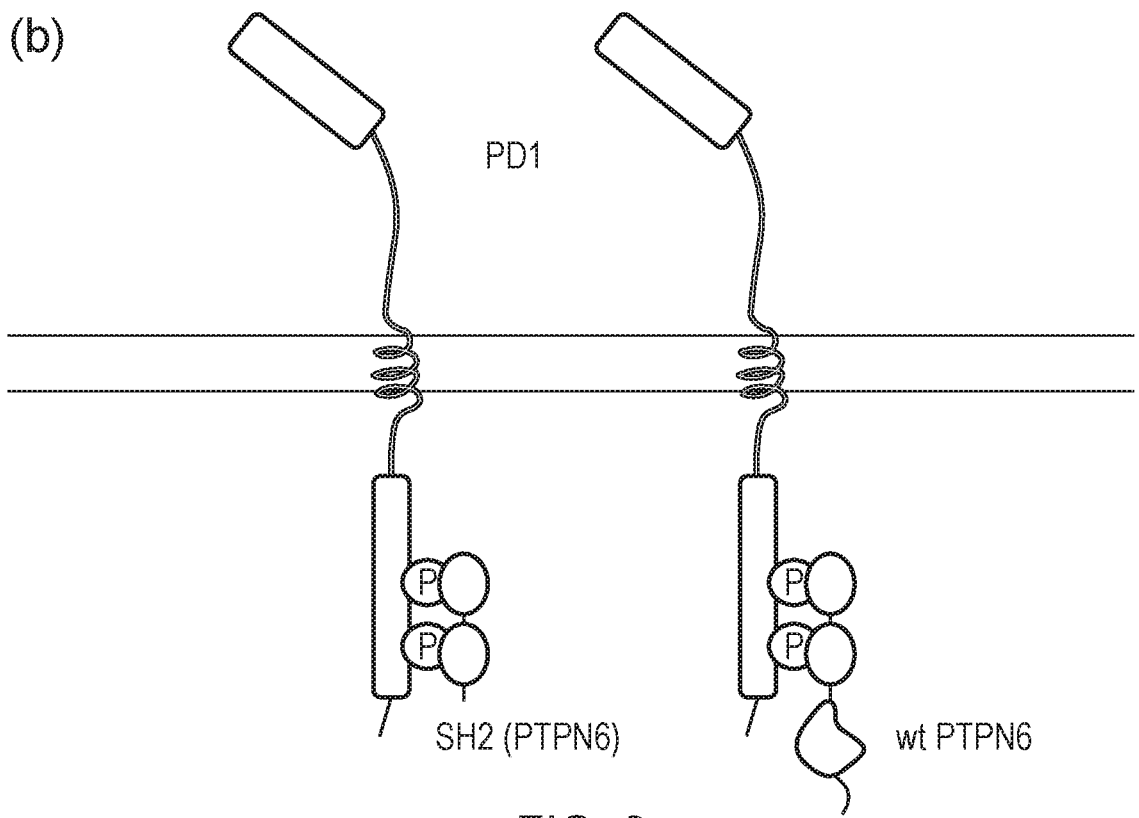
FIG. 2

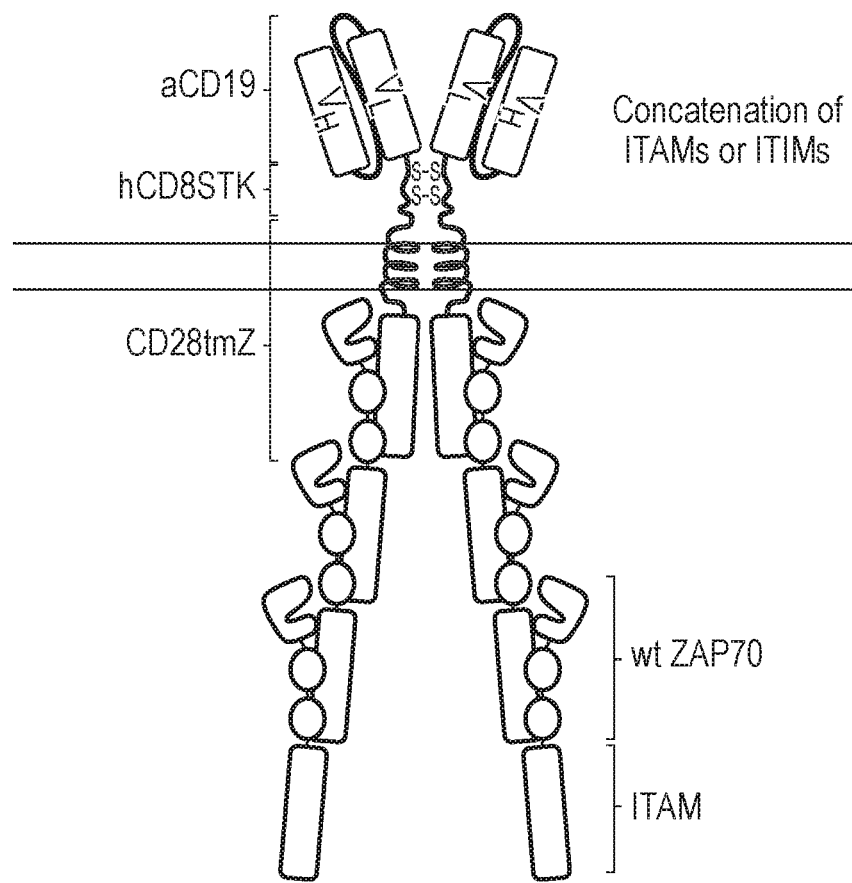
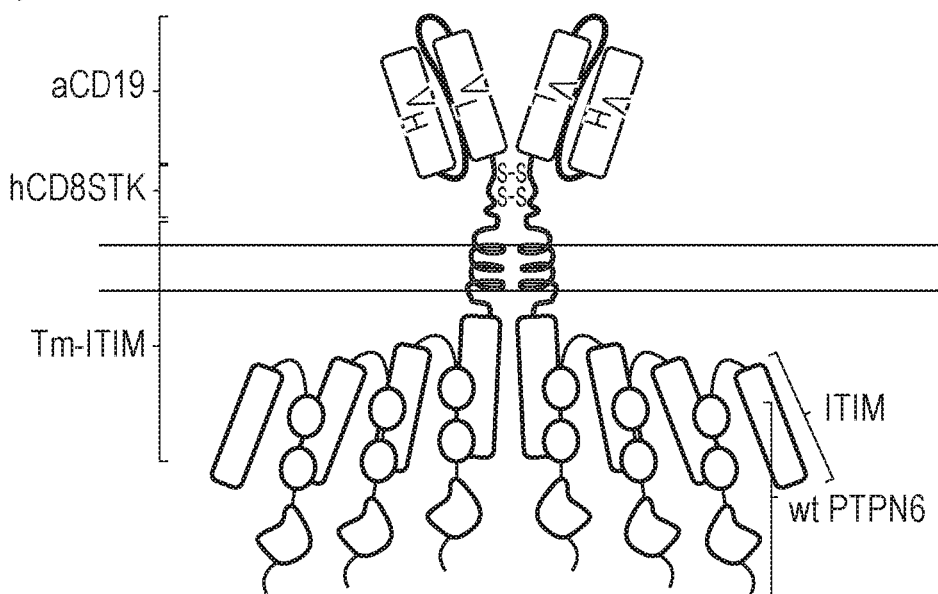
FIG. 4

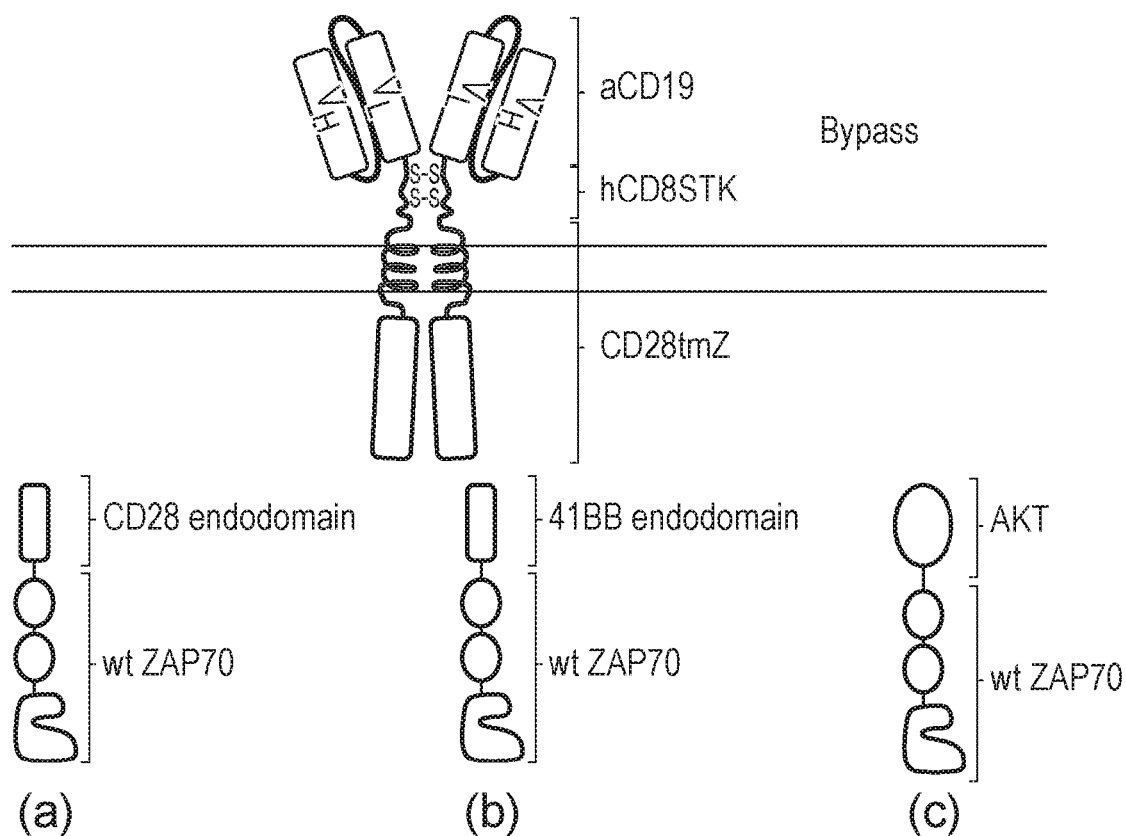
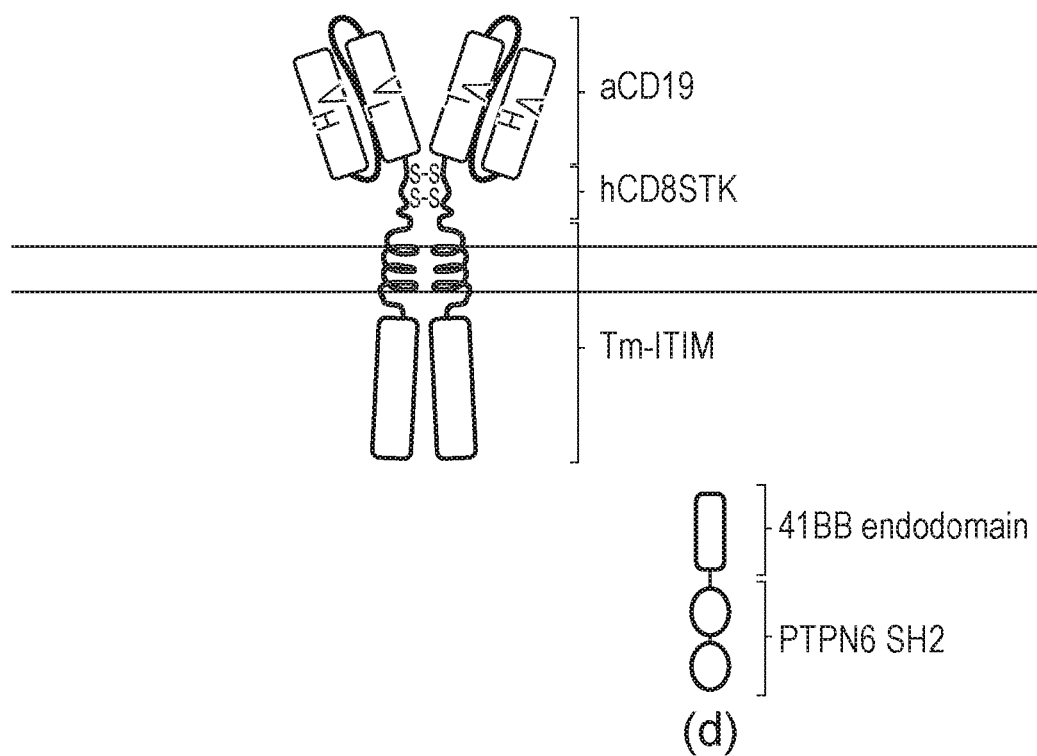
FIG. 5

Castration
(a)
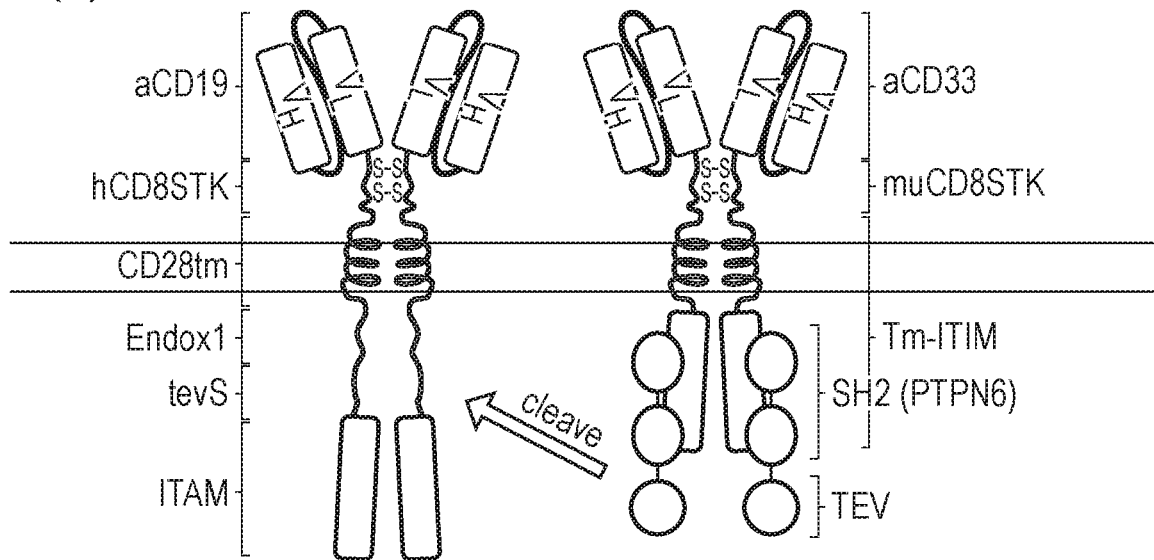
(b)
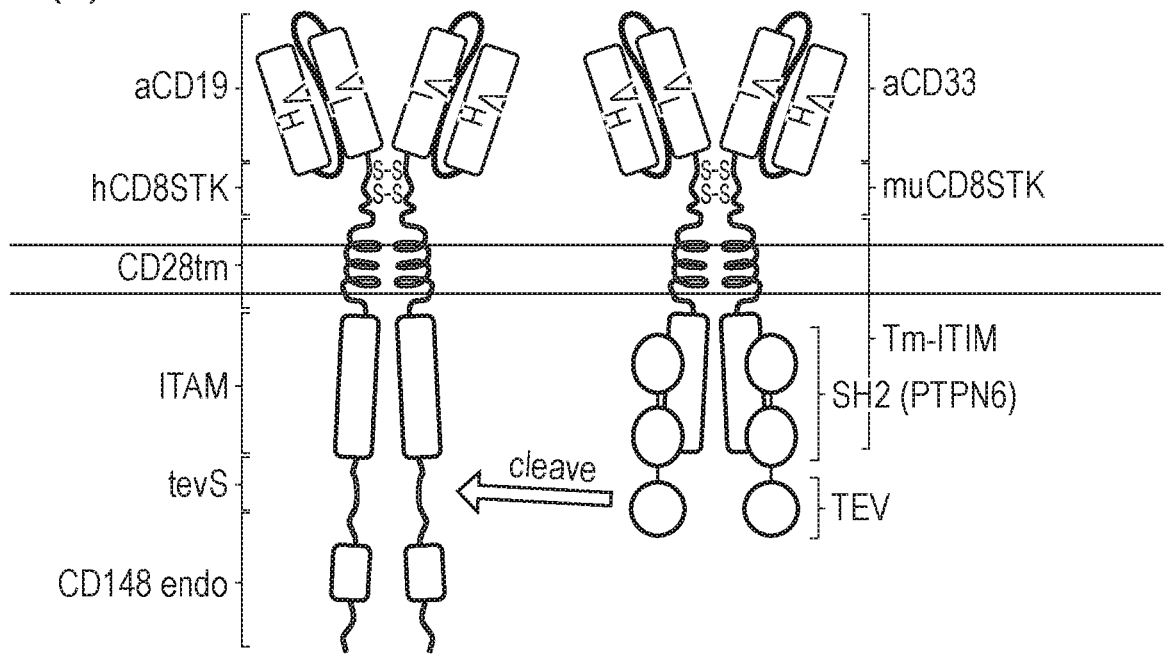
FIG. 7

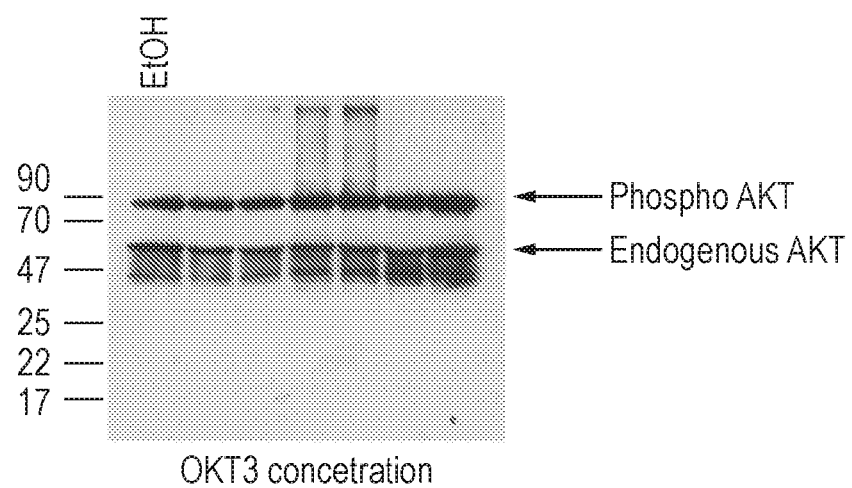
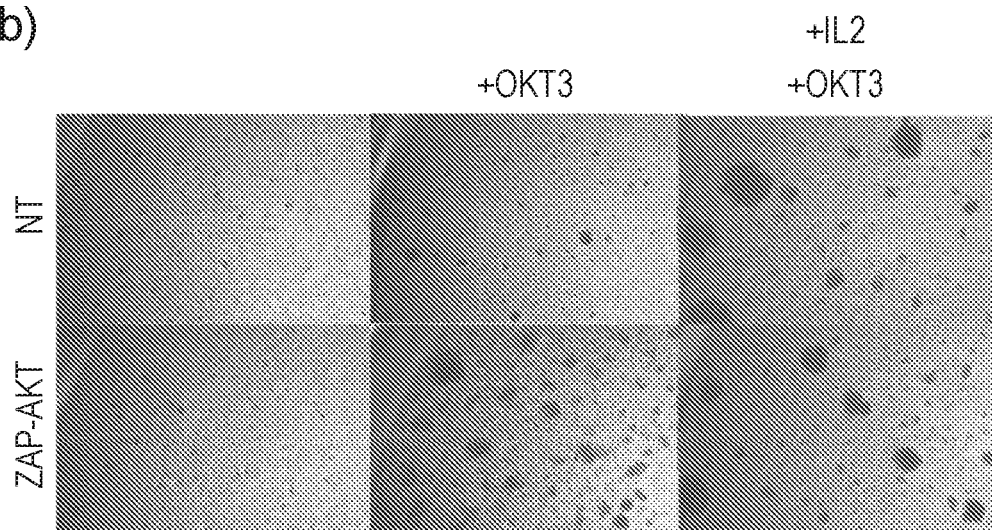
FIG. 10

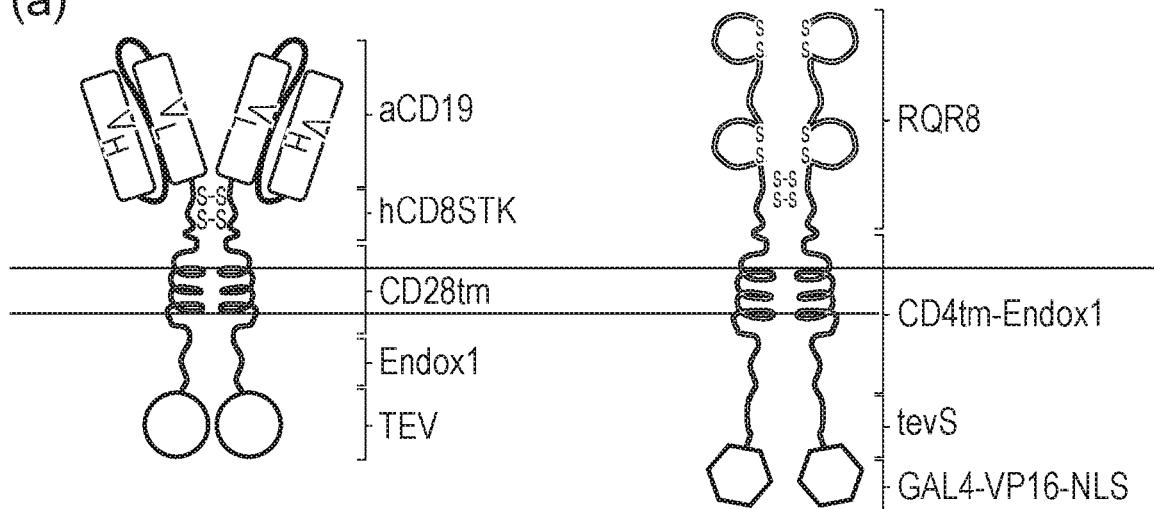
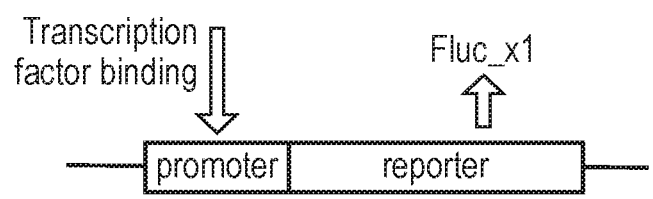
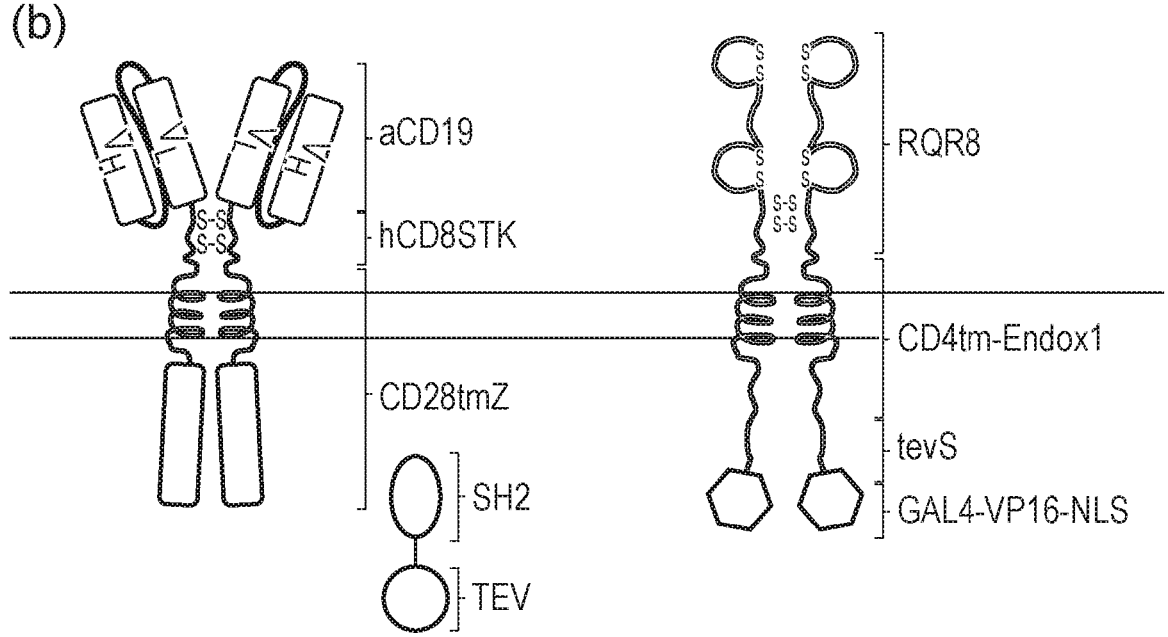
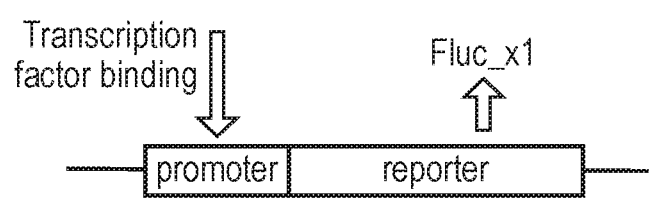
FIG. 11

>dZAP_SH2 (SEQ ID No. 2)
MPDPAAHLPFFYGSISRAEAEEHLKLAGMADGLFLLRQCLRSLGGYVLSLVHDVRFHHFPIERQLNGTYAI
AGGKAHCGPAELCEFYSRDPDGLPCNLRKPCNRPSGLEPQPGVFDCLRDAMVRDYVRQTWKLEGEALE
QAIISQAPQVEKLIATTAHERMPWYHSSLTREEAERKLYSGAQTDGKFLLRPRKEQGTYALSLIYGKTVYHY
LISQDKAGKYCIPEGTKFDTLWQLVEYLKLKADGLIYCLKEACPNSSASNASGAAAPTLPAHPSTLTHP

MPD – ZAP70 SH2 domain

>dPTPN6_SH2 (SEQ ID No. 6)
MVRWFHRDLSGLDAETLLKGRGVHGSFLARPSRKNQGDFSLSVRVGDQVTHIRIQNSGDFYDLYGGEKF
ATLTELVEYYTQQQGVLQDRDGTIIHLKYPLNCSDPTSERWYHGHMSGGQAETLLQAKGEPWTFLVRES
LSQPGDFVLSVLSDQPKAGPGSPLRVTHIKVMCEGGRYTVGGLETFDSLTDLVEHFKKTGIEEASGAFVYL
RQPYY

MVR – PTPN6 SH2 domain

>ZAP_SH2-PTPN6 (SEQ ID No. 30)
MPDPAAHLPFFYGSISRAEAEEHLKLAGMADGLFLLRQCLRSLGGYVLSLVHDVRFHHFPIERQLNGTYAI
AGGKAHCGPAELCEFYSRDPDGLPCNLRKPCNRPSGLEPQPGVFDCLRDAMVRDYVRQTWKLEGEALE
QAIISQAPQVEKLIATTAHERMPWYHSSLTREEAERKLYSGAQTDGKFLLRPRKEQGTYALSLIYGKTVYHY
LISQDKAGKYCIPEGTKFDTLWQLVEYLKLKADGLIYCLKEACPNSSASNASGAAAPTLPAHPSTLTHPSGG
GGSGGGGSGGGGSGGGGSFWEEFESLQKQEVKNLHQRLEGQRPENKGKNRYKNILPFDHSRVILQGRD
SNIPGSDYINANYIKNQLLGPDENAKTYIASQGCLEATVNDFWQMAWQENSRVIVMTTREVEKGRNKC
VPYWPEVGMQRAYGPYSVTNCGEHDTTEYKLRTLQVSPLDNGDLIREIWHYQYLSWPDHGVPSEPGGV
LSFLDQINQRQESLPHAGPIIVHCSAGIGRTGTIIVIDMLMENISTKGLDCDIDIQKTIQMVRAQRSGMVQ
TEAQYKFIYVAIAQFIETTKKKL

MPD – ZAP70 SH2 domain
SGG - Linker
FEW - PTPN6 kinase

>PTPN6_SH2-ZAP (SEQ ID No. 29)
MVRWFHRDLSGLDAETLLKGRGVHGSFLARPSRKNQGDFSLSVRVGDQVTHIRIQNSGDFYDLYGGEKF
ATLTELVEYYTQQQGVLQDRDGTIIHLKYPLNCSDPTSERWYHGHMSGGQAETLLQAKGEPWTFLVRES
LSQPGDFVLSVLSDQPKAGPGSPLRVTHIKVMCEGGRYTVGGLETFDSLTDLVEHFKKTGIEEASGAFVYL
RQPYYSGGGSDPEELKDKKLFLKRDNLLIADIELGCGNFGSVRQGVYRMRKKQIDVAIKVLKQGTEKAD
TEEMMREAQIMHQLDNPYIVRLIGVCQAEALMLVMEMAGGGPLHKFLVGKREEIPVSNVAELLHQVS
MGMKYLEEKNFVHRDLAARNVLLVNRHYAKISDFGLSKALGADDSYYTARSAGKWPLKWYAPECINFRK
FSSRSDVWSYGVTMWEALSYGQKPYKKMKGPEVMAFIEQGKRMECPPECPPELYALMSDCWIYKWED
RPDFLTVEQRMRACYYSLASKVEGPPGSTQKAEAACA

MVR - PTPN6 SH2 domain
SGG - Linker

FIG. 14

DPE – ZAP70 kinase

>ZETA-ZAP (SEQ ID No. 14)

MRRVKFSRSADAPAYQQGQNQLYNELNLGRREEYDVLDKRRGRDPEMGGKPRRKNPQEGLYNELQKD
KMAEAYSEIGMKGERRRGKGHDGLYQGLSTATKDTYDALHMQALPPRSGGGGSGGGGSGGGGSGGG
GSMPDPAAHLPFFYGSISRAEAEEHLKLAGMADGLFLLRQCLRSLGGYVLSLVHDVRFHHFPIERQLNGTY
AIAGGKAHCGPAELCEFYSRDPDGLPCNLRKPCNRPSGLEPQPGVFDCLRDAMVRDYVRQTWKLEGEAL
EQAIISQAPQVEKLIATTAHERMPWYHSSLTREEAERKLYSGAQTDGKFLLRPRKEQGTYALSLIYGKTVYH
YLISQDKAGKYCIPEGTKFDTLWQLVEYLKLKADGLIYCLKEACPNSSASNASGAAAPTLPAHPSTLTHPQR
RIDTLNSDGYTPEPARITSPDKPRPMPMDTSVYESPYSDPEELKDKKLFLKRDNLLIADIELGCGNFGSVRQ
GVYRMRKKQIDVAIKVLKQGTEKADTEEMMREAQIMHQLDNPYIVRLIGVCQAEALMLVMEMAGGGP
LHKFLVGKREEIPVSNVAELLHQVSMGMKYLEEKNFVHRDLAARNVLLVNRHYAKISDFGLSKALGADDS
YYTARSAGKWPLKWYAPECINFRKFSSRSDVWSYGVTMWEALSYGQKPYKKMKGPEVMAFIEQGKRM
ECPPECPPELYALMSDCWIYKWEDRPDFLTVEQRMRACYYSLASKVEGPPGSTQKAEAACA

MRR - CD3Zeta endodomain
SGG - Linker
MPD - full-length ZAP70

> PD1_endo-PTPN6 (SEQ ID No. 25)

MTGQPLKEDPSAVPVFSVDYGELDFQWREKTPEPPVPCVPEQTEYATIVFPSGMGTSSPARRGSADGPR
SAQPLRPEDGHCSWPLSGGGGSGGGGSGGGGSGGGGSMVRWFHRDLSGLDAETLLKGRGVHGSFLA
RPSRKNQGDFSLSVRVGDQVTHIRIQNSGDFYDLYGGEKFATLTELVEYYTQQQGVLQDRDGTIIHLKYPL
NCSDPTSERWYHGHMSGGQAETLLQAKGEPWTFLVRESLSQPGDFVLSVLSDQPKAGPGSPLRVTHIKV
MCEGGRYTVGGLETFDSLTDLVEHFKKTGIEEASGAFVYLRQPYYATRVNAADIENRVLELNKKQESEDTA
KAGFWEEFESLQKQEVKNLHQRLEGQRPENKGKNRYKNILPFDHSRVILQGRDSNIPGSDYINANYIKNQ
LLGPDENAKTYIASQGCLEATVNDFWQMAWQENSRVIVMTTREVEKGRNKCVPYWPEVGMQRAYGP
YSVTNCGEHDTTEYKLRTLQVSPLDNGDLIREIWHYQYLSWPDHGVPSEPGGVLSFLDQINQRQESLPHA
GPIIVHCSAGIGRTGTIIVIDMLMENISTKGLDCDIDIQKTIQMVRAQRSGMVQTEAQYKFIYVAIAQFIETT
KKKLEVLQSQKGQESEYGNITYPPAMKNAHAKASRTSSKHKEDVYENLHTKNKREEKVKKQRSADKEKSK
GSLKRK

MTG - PD1 endodomain
SGG - Linker
MVR - full length PTPN6

>CD28-ZAP (SEQ ID No. 40)

MRSKRSRLLHSDYMNMTPRRPGPTRKHYQPYAPPRDFAAYRSSGGGGSGGGGSGGGGSGGGGSMPD
PAAHLPFFYGSISRAEAEEHLKLAGMADGLFLLRQCLRSLGGYVLSLVHDVRFHHFPIERQLNGTYAIAGG
KAHCGPAELCEFYSRDPDGLPCNLRKPCNRPSGLEPQPGVFDCLRDAMVRDYVRQTWKLEGEALEQAIIS
QAPQVEKLIATTAHERMPWYHSSLTREEAERKLYSGAQTDGKFLLRPRKEQGTYALSLIYGKTVYHYLISQ
DKAGKYCIPEGTKFDTLWQLVEYLKLKADGLIYCLKEACPNSSASNASGAAAPTLPAHPSTLTHPQRRIDTL
NSDGYTPEPARITSPDKPRPMPMDTSVYESPYSDPEELKDKKLFLKRDNLLIADIELGCGNFGSVRQGVYR
MRKKQIDVAIKVLKQGTEKADTEEMMREAQIMHQLDNPYIVRLIGVCQAEALMLVMEMAGGGPLHKF
LVGKREEIPVSNVAELLHQVSMGMKYLEEKNFVHRDLAARNVLLVNRHYAKISDFGLSKALGADDSYYTA

FIG. 14 (continued)

RSAGKWPLKWYAPECINFRKFSSRSDVWSYGVTMWEALSYGQKPYKKMKGPEVMAFIEQGKRMECPP
ECPPELYALMSDCWIYKWEDRPDFLTVEQRMRACYYSLASKVEGPPGSTQKAEAACA

MRS - CD28 endodomain
SGG - Linker
MPD - full-length ZAP70

>41BB-ZAP (SEQ ID No. 41)
MKRGRKKLLYIFKQPFMRPVQTTQEEDGCSCRFPEEEEGGCELSGGGGSGGGGSGGGGSGGGGSMPD
PAAHLPFFYGSISRAEAEEHLKLAGMADGLFLLRQCLRSLGGYVLSLVHDVRFHHFPIERQLNGTYAIAGG
KAHCGPAELCEFYSRDPDGLPCNLRKPCNRPSGLEPQPGVFDCLRDAMVRDYVRQTWKLEGEALEQAIIS
QAPQVEKLIATTAHERMPWYHSSLTREEAERKLYSGAQTDGKFLLRPRKEQGTYALSLIYGKTVYHYLISQ
DKAGKYCIPEGTKFDTLWQLVEYLKLKADGLIYCLKEACPNSSASNASGAAAPTLPAHPSTLTHPQRRIDTL
NSDGYTPEPARITSPDKPRPMPMDTSVYESPYSDPEELKDKKLFLKRDNLLIADIELGCGNFGSVRQGVYR
MRKKQIDVAIKVLKQGTEKADTEEMMREAQIMHQLDNPYIVRLIGVCQAEALMLVMEMAGGGPLHKF
LVGKREEIPVSNVAELLHQVSMGMKYLEEKNFVHRDLAARNVLLVNRHYAKISDFGLSKALGADDSYYTA
RSAGKWPLKWYAPECINFRKFSSRSDVWSYGVTMWEALSYGQKPYKKMKGPEVMAFIEQGKRMECPP
ECPPELYALMSDCWIYKWEDRPDFLTVEQRMRACYYSLASKVEGPPGSTQKAEAACA

MKR - 41BB endodomain
SGG - Linker
MPD - full-length ZAP70

>OX40-ZAP (SEQ ID No. 42)
MRDQRLPPDAHKPPGGGSFRTPIQEEQADAHSTLAKSGGGGSGGGGSGGGGSGGGGSMPDPAAHLP
FFYGSISRAEAEEHLKLAGMADGLFLLRQCLRSLGGYVLSLVHDVRFHHFPIERQLNGTYAIAGGKAHCGP
AELCEFYSRDPDGLPCNLRKPCNRPSGLEPQPGVFDCLRDAMVRDYVRQTWKLEGEALEQAIISQAPQV
EKLIATTAHERMPWYHSSLTREEAERKLYSGAQTDGKFLLRPRKEQGTYALSLIYGKTVYHYLISQDKAGKY
CIPEGTKFDTLWQLVEYLKLKADGLIYCLKEACPNSSASNASGAAAPTLPAHPSTLTHPQRRIDTLNSDGYT
PEPARITSPDKPRPMPMDTSVYESPYSDPEELKDKKLFLKRDNLLIADIELGCGNFGSVRQGVYRMRKKQ
DVAIKVLKQGTEKADTEEMMREAQIMHQLDNPYIVRLIGVCQAEALMLVMEMAGGGPLHKFLVGKRE
EIPVSNVAELLHQVSMGMKYLEEKNFVHRDLAARNVLLVNRHYAKISDFGLSKALGADDSYYTARSAGK
WPLKWYAPECINFRKFSSRSDVWSYGVTMWEALSYGQKPYKKMKGPEVMAFIEQGKRMECPPECPPE
LYALMSDCWIYKWEDRPDFLTVEQRMRACYYSLASKVEGPPGSTQKAEAACA

MRD - OX40 endodomain
SGG - Linker
MPD - full-length ZAP70

>CD28-PTPN6_SH2 (SEQ ID No. 43)
MRSKRSRLLHSDYMNMTPRRPGPTRKHYQPYAPPRDFAAYRSSGGGGSGGGGSGGGGSGGGGSMVR
WFHRDLSGLDAETLLKGRGVHGSFLARPSRKNQGDFSLSVRVGDQVTHIRIQNSGDFYDLYGGEKFATLT
ELVEYYTQQQGVLQDRDGTIIHLKYPLNCSDPTSERWYHGHMSGGQAETLLQAKGEPWTFLVRESLSQP
GDFVLSVLSDQPKAGPGSPLRVTHIKVMCEGGRYTVGGLETFDSLTDLVEHFKKTGIEEASGAFVYLRQPY

FIG. 14 (continued)

MRS - CD28 endodomain
SGG - Linker
MVR - amino-terminus of PTPN6 SH2 domain

>41BB-PTPN6_SH2 (SEQ ID No. 44)
MKRGRKKLLYIFKQPFMRPVQTTQEEDGCSCRFPEEEEGGCELSGGGGSGGGGSGGGGSGGGGSMVR
WFHRDLSGLDAETLLKGRGVHGSFLARPSRKNQGDFSLSVRVGDQVTHIRIQNSGDFYDLYGGEKFATLT
ELVEYYTQQQGVLQDRDGTIIHLKYPLNCSDPTSERWYHGHMSGGQAETLLQAKGEPWTFLVRESLSQP
GDFVLSVLSDQPKAGPGSPLRVTHIKVMCEGGRYTVGGLETFDSLTDLVEHFKKTGIEEASGAFVYLRQPY

MKR - 41BB endodomain
SGG - Linker
MVR - amino-terminus of PTPN6 SH2 domain

>OX40-PTPN6_SH2 (SEQ ID No. 45)
MRDQRLPPDAHKPPGGGSFRTPIQEEQADAHSTLAKISGGGGSGGGGSGGGGSGGGGSMVRWFHRD
LSGLDAETLLKGRGVHGSFLARPSRKNQGDFSLSVRVGDQVTHIRIQNSGDFYDLYGGEKFATLTELVEYY
TQQQGVLQDRDGTIIHLKYPLNCSDPTSERWYHGHMSGGQAETLLQAKGEPWTFLVRESLSQPGDFVL
SVLSDQPKAGPGSPLRVTHIKVMCEGGRYTVGGLETFDSLTDLVEHFKKTGIEEASGAFVYLRQPY

MRD - OX40 endodomain
SGG - Linker
MVR - amino-terminus of PTPN6 SH2 domain

>ZAP_SH2-AKT (SEQ ID No. 47)
MPDPAAHLPFFYGSISRAEAEEHLKLAGMADGLFLLRQCLRSLGGYVLSLVHDVRFHHFPIERQLNGTYAI
AGGKAHCGPAELCEFYSRDPDGLPCNLRKPCNRPSGLEPQPGVFDCLRDAMVRDYVRQTWKLEGEALE
QAIISQAPQVEKLIATTAHERMPWYHSSLTREEAERKLYSGAQTDGKFLLRPRKEQGTYALSLIYGKTVYHY
LISQDKAGKYCIPEGTKFDTLWQLVEYLKLKADGLIYCLKEACPNSSASNASGAAAPTLPAHPSTLTHPAEE
MEVSLAKPKHRVTMNEFEYLKLLGKGTFGKVILVKEKATGRYYAMKILKKEVIVAKDEVAHTLTENRVLQN
SRHPFLTALKYSFQTHDRLCFVMEYANGGELFFHLSRERVFSEDRARFYGAEIVSALDYLHSEKNVVYRDLK
LENLMLDKDGHIKITDFGLCKEGIKDGATMKTFCGTPEYLAPEVLEDNDYGRAVDWWGLGVVMYEMM
CGRLPFYNQDHEKLFELILMEEIRFPRTLGPEAKSLLSGLLKKDPKQRLGGGSEDAKEIMQHRFFAGIVWQ
HVYEKKLSPPFKPQVTSETDTRYFDEEFTAQMITITPPDQDDSMECVDSERRPHFPQFSYSASGTA

MPD - ZAP70 SH2 domain
AEE - AKT kinase

>ZAP_SH2-L-AKT (SEQ ID No. 48)
fused with via a linker
MPDPAAHLPFFYGSISRAEAEEHLKLAGMADGLFLLRQCLRSLGGYVLSLVHDVRFHHFPIERQLNGTYAI
AGGKAHCGPAELCEFYSRDPDGLPCNLRKPCNRPSGLEPQPGVFDCLRDAMVRDYVRQTWKLEGEALE
QAIISQAPQVEKLIATTAHERMPWYHSSLTREEAERKLYSGAQTDGKFLLRPRKEQGTYALSLIYGKTVYHY
LISQDKAGKYCIPEGTKFDTLWQLVEYLKLKADGLIYCLKEACPNSSASNASGAAAPTLPAHPSTLTHPSGG
GGSGGGGSGGGGSGGGGSAEEMEVSLAKPKHRVTMNEFEYLKLLGKGTFGKVILVKEKATGRYYAMKIL FIG. 14 (continued)

KKEVIVAKDEVAHTLTENRVLQNSRHPFLTALKYSFQTHDRLCFVMEYANGGELFFHLSRERVFSEDRARF
YGAEIVSALDYLHSEKNVVYRDLKLENLMLDKDGHIKITDFGLCKEGIKDGATMKTFCGTPEYLAPEVLED
NDYGRAVDWWGLGVVMYEMMCGRLPFYNQDHEKLFELILMEEIRFPRTLGPEAKSLLSGLLKKDPKQR
LGGGSEDAKEIMQHRFFAGIVWQHVYEKKLSPPFKPQVTSETDTRYFDEEFTAQMITITPPDQDDSMEG
VDSERRPHFPQFSYSASGTA

MPD - ZAP70 SH2 domain
SGG - Linker
AEE - AKT kinase domain

>ZAPnf-AKT (SEQ ID No. 49)
MPDPAAHLPFFYGSISRAEAEEHLKLAGMADGLFLLRQCLRSLGGYVLSLVHDVRFHHFPIERQLNGTYAI
AGGKAHCGPAELCEFYSRDPDGLPCNLRKPCNRPSGLEPQPGVFDCLRDAMVRDYVRQTWKLEGEALE
QAIISQAPQVEKLIATTAHERMPWYHSSLTREEAERKLYSGAQTDGKFLLKPRKEQGTYALSLIYGKTVYHY
LISQDKAGKYCIPEGTKFDTLWQLVEYLKLKADGLIYCLKEACPNSSASNASGAAAPTLPAHPSTLTHPAEE
MEVSLAKPKHRVTMNEFEYLKLLGKGTFGKVILVKEKATGRYYAMKILKKEVIVAKDEVAHTLTENRVLQN
SRHPFLTALKYSFQTHDRLCFVMEYANGGELFFHLSRERVFSEDRARFYGAEIVSALDYLHSEKNVVYRDLK
LENLMLDKDGHIKITDFGLCKEGIKDGATMKTFCGTPEYLAPEVLEDNDYGRAVDWWGLGVVMYEMM
CGRLPFYNQDHEKLFELILMEEIRFPRTLGPEAKSLLSGLLKKDPKQRLGGGSEDAKEIMQHRFFAGIVWQ
HVYEKKLSPPFKPQVTSETDTRYFDEEFTAQMITITPPDQDDSMECVDSERRPHFPQFSYSASGTA

MPD - ZAP70 mutated to be non-functional
AEE - AKT kinase

>ZAP_SH2-TEV (SEQ ID No. 53)
MPDPAAHLPFFYGSISRAEAEEHLKLAGMADGLFLLRQCLRSLGGYVLSLVHDVRFHHFPIERQLNGTYAI
AGGKAHCGPAELCEFYSRDPDGLPCNLRKPCNRPSGLEPQPGVFDCLRDAMVRDYVRQTWKLEGEALE
QAIISQAPQVEKLIATTAHERMPWYHSSLTREEAERKLYSGAQTDGKFLLRPRKEQGTYALSLIYGKTVYHY
LISQDKAGKYCIPEGTKFDTLWQLVEYLKLKADGLIYCLKEACPNSSASNASGAAAPTLPAHPSTLTHPSGG
GGSGGGGSGGGGSGGGGSSLFKGPRDYNPISSTICHLTNESDGHTTSLYGIGFGPFIITNKHLFRRNNGTL
LVQSLHGVFKVKNTTTLQQHLIDGRDMIIIRMPKDFPPFPQKLKFREPQREERICLVTTNFQTKSMSSMVS
DTSCTFPSSDGIFWKHWIQTKDGQCGSPLVSTRDGFIVGIHSASNFTNTNNYFTSVPKNFMELLTNQEAQ
QWVSGWRLNADSVLWGGHKVFMSKPEEPFQPVKEATQLMNELVYSQ

MPD - ZAP70 SH2 domain
SLH - TEV protease

>PTPN6_SH2-TEV (SEQ ID No. 54)
MVRWFHRDLSGLDAETLLKGRGVHGSFLARPSRKNQGDFSLSVRVGDQVTHIRIQNSGDFYDLYGGEKR
ATLTELVEYYTQQQGVLQDRDGTIIHLKYPLNCSDPTSERWYHGHMSGGQAETLLQAKGEPWTFLVRES
LSQPGDFVLSVLSDQPKAGPGSPLRVTHIKVMCEGGRYTVGGLETFDSLTDLVEHFKKTGIEEASGAFVYL
RQPYYSGGGGSSLFKGPRDYNPISSTICHLTNESDGHTTSLYGIGFGPFIITNKHLFRRNNGTLLVQSLHGVF
KVKNTTTLQQHLIDGRDMIIIRMPKDFPPFPQKLKFREPQREERICLVTTNFQTKSMSSMVSDTSCTFPSS
DGIFWKHWIQTKDGQCGSPLVSTRDGFIVGIHSASNFTNTNNYFTSVPKNFMELLTNQEAQQWVSGW
RLNADSVLWGGHKVFMSKPEEPFQPVKEATQLMNELVYSQ

FIG. 14 (continued)

MVR - PTPN6 SH2 domain
SGG - Linker
SLH - TEV protease

>RQR8-CD4tm-Endox1-tevS-VP16-GAL4 (SEQ ID No. 55)
MGTSLLCWMALCLLGADHADACPYSNPSLCSGGGGSELPTQGTFSNVSTNVSPAKPTTTACPYSNPSLG
SGGGGSPAPRPPTPAPTIASQPLSLRPEACRPAAGGAVHTRGLDFACDMALIVLGGVAGLLLFIGLGIFFC
VRCRHRRRQAERMAQIKRVVSEKKTAQAPHRFQKTCSPSGGGGSENLYFQMPKKKRKVAPPTDVSLGD
ELHLDGEDVAMAHADALDDFDLDMLGDGDSPGPGFTPHDSAPYGALDMADFEFEQMFTDALGIDEYG
GSGGGSMQILVASDATMKLLSSIEQACDICRLKKLKCSKEKPKCAKCLKNNWECRYSPKTKRSPLTRAHLT
EVESRLERLEQLFLLIFPREDLDMILKMDSLQDIKALLTGLFVQDNVNKDAVTDRLASVETDMPLTLRQHR
SATSSSEESSNKGQRQLTV MGT – RQR8 domain
RCR - CD4tm
SGG - Linker
ENL – TEV recognition site
PKK - VP16
MQI - GAL4

>aCD33-muCD8STK-PD1_tm_endo (SEQ ID No. 56)
MAVPTQVLGLLLLWLTDARCDIQMTQSPSSLSASVGDRVTITCRASEDIYFNLVWYQQKPGKAPKLLIYD
TNRLADGVPSRFSGSGSGTQYTLTISSLQPEDFATYYCQHYKNYPLTFGQGTKLEIKRSGGGGSGGGGSG
GGGSGGGGSRSEVQLVESGGGLVQPGGSLRLSCAASGFTLSNYGMHWIRQAPGKGLEWVSSISLNGGS
TYYRDSVKGRFTISRDNAKSTLYLQMNSLRAEDTAVYYCAAQDAYTGGYFDYWGQGTLVTVSSMDPATT
TKPVLRTPSPVHPTGTSQPQRPEDCRPRGSVKGTGLDFACDIVGVVGGLLGSLVLLVWVLAVICSRAAR
GTIGARRTGQPLKEDPSAVPVFSVDYGELDFQWREKTPEPPVPCVPEQTEYATIVFPSGMGTSSPARRGS
ADGPRSAQPLRPEDGHCSWPL MAV – anti-CD33
TTT - Mouse CD8alpha stalk
VGV – PD-1 endodomain >aCD19-hCD8STK-CD28tm-Endox1-tevS-Z (SEQ ID No. 57)
CAR against CD19 with cleavable Zeta endodomain
MSLPVTALLLPLALLLHAARPDIQMTQTTSSLSASLGDRVTISCRASQDISKYLNWYQQKPDGTVKLLIYHT
SRLHSGVPSRFSGSGSGTDYSLTISNLEQEDIATYFCQQGNTLPYTFGGGTKLEITKAGGGGSGGGGSGGG
GSGGGGSEVKLQESGPGLVAPSQSLSVTCTVSGVSLPDYGVSWIRQPPRKGLEWLGVIWGSETTYYNSAL
KSRLTIIKDNSKSQVFLKMNSLQTDDTAIYYCAKHYYYGGSYAMDYWGQGTSVTVSSDPTTTPAPRPPTP
APTIASQPLSLRPEACRPAAGGAVHTRGLDFACDFWVLVVVGGVLACYSLLVTVAFIIFWVRCRHRRRQ
AERMAQIKRVVSEKKTAQAPHRFQKTCSPSGGGGSENLYFQMRRVKFSRSADAPAYQQGQNQLYNEL
NLGRREEYDVLDKRRGRDPEMGGKPRRKNPQEGLYNELQKDKMAEAYSEIGMKGERRRGKGHDGLYQ
GLSTATKDTYDALHMQALPPR FIG. 14 (continued)

MSL – anti-CD19
PTT – CD8alpha stalk
FWV – CD28 transmembrane domain
RCR – Endox1
ENL – TEV recognition site
RRV – CD3 zeta endodomain >aCD19-hCD8STK-CD28tmZ-tevS-CD148endo (SEQ ID No. 58)
CAR against CD19 with Zeta endodomain and cleavable CD148 catalytic domain MSLPVTALLLPLALLLHAARPDIQMTQTTSSLSASLGDRVTISCRASQDISKYLNWYQQKPDGTVKLLIYHT
SRLHSGVPSRFSGSGSGTDYSLTISNLEQEDIATYFCQQGNTLPYTFGGGTKLEITKAGGGGSGGGGSGGG
GSGGGGSEVKLQESGPGLVAPSQSLSVTCTVSGVSLPDYGVSWIRQPPRKGLEWLGVIWGSETTYYNSAL
KSRLTIIKDNSKSQVFLKMNSLQTDDTAIYYCAKHYYYGGSYAMDYWGQGTSVTVSSDPTTTPAPRPPTP
APTIASQPLSLRPEACRPAAGGAVHTRGLDFACDIFWVLVVVGGVLACYSLLVTVAFIIFWVRRVKFSRSA
DAPAYQQGQNQLYNELNLGRREEYDVLDKRRGRDPEMGGKPRRKNPQEGLYNELQKDKMAEAYSEIG
MKGERRRGKGHDGLYQGLSTATKDTYDALHMQALPPRENLYFQMAVFGCIFGALVIVTVGGFIFWRKK
RKDAKNNEVSFSQIKPKKSKLIRVENFEAYFKKQQADSNCGFAEEYEDLKLVGISQPKYAAELAENRGKNR
YNNVLPYDISRVKLSVQTHSTDDYINANYMPGYHSKKDFIATQGPLPNTLKDFWRMVWEKNVYAIIMLT
KCVEQGRTKCEEYWPSKQAQDYGDITVAMTSEIVLPEWTIRDFTVKNIQTSESHPLRQFHFTSWPDHGV
PDTTDLLINFRYLVRDYMKQSPPESPILVHCSAGVGRTGTFIAIDRLIYQIENENTVDVYGIVYDLRMHRPL
MVQTEDQYVFLNQCVLDIVRSQKDSKVDLIYQNTTAMTIYENLAPVTTFGKTNGYIA MSL – anti-CD19
PTT – CD8alpha stalk
FWV – CD28 transmembrane domain
RRV – CD3 zeta endodomain
ENL – TEV recognition site
AVF – CD148 endodomain >dualSH2 SHP-1-ZAP70 kinase (SEQ ID No. 61)
MFHPNITGVEAENLLLTRGVDGSFLARPSKSNPGDFTLSVRRNGAVTHIKIQNTGDYYDLYG
GEKFATLAELVQYYMEHHGQLKEKNGDVIELKYPLNCADPTSERWFHGHLSGKEAEKLLTE
KGKHGSFLVRESQSHPGDFVLSVRTGDDKGESNDGKSKVTHVMIRCQELKYDVGGGERFD
SLTDLVEHYKKNPMVETLGTVLQLKQPLNTTRINPNSSASNASGAAAPTLPAHPSTLTHPQR
RIDTLNSDGYTPEPARITSPDKPRPMPMDTSVYESPYSDPEELKDKKLFLKRDNLTADIELGC
GNFGSVRQGVYRMRKKQIDVAIKVLKQGTEKADTEEMMREAQIMHQLDNPYIVRLIGVCQAE
ALMLVMEMAGGGPLHKFLVGKREEIPVSNVAELLHQVSMGMKYLEEKNFVHRDLAARNVLLT
VNRHYAKISDFGLSKALGADDSYYTARSAGKWPLKWYAPECINFRKFSSRSDVWSYGVTM
WEALSYGQKPYKKMKGPEVMAFIEQGKRMECPPECPPELYALMSDCWIYKWEDRPDFLTV
EQRMRACYYSL WFH – First SH2 domain from SHP-2
NCA – Linker
WFH – Second SH2 domain from SHP-2
NTT – Linker
LIA – Zap-70 protein kinase >-dualSH2 SHP-2-Akt Kinase (SEQ ID No. 62)
MFHPNITGVEAENLLLTRGVDGSFLARPSKSNPGDFTLSVRRNGAVTHIKIQNTGDYYDLYG
GEKFATLAELVQYYMEHHGQLKEKNGDVIELKYPLNCADPTSERWFHGHLSGKEAEKLLTE
KGKHGSFLVRESQSHPGDFVLSVRTGDDKGESNDGKSKVTHVMIRCQELKYDVGGGERFD FIG. 14 (continued)

SLTDLVEHYKKNPMVETLGTVLQLKQPLNTTRINAEEMEVSLAKPKHRVTMNEFEYLKLLGK
GTFGKVILVKEKATGRYYAMKILKKEVIVAKDEVAHTLTENRVLQNSRHPFLTALKYSFQTHD
RLCFVMEYANGGELFFHLSRERVFSEDRARFYGAEIVSALDYLHSEKNVVYRDLKLENLMLD
KDGHIKITDFGLCKEGIKDGATMKTFCGTPEYLAPEVLEDNDYGRAVDWWGLGVVMYEMMC
GRLPFYNQDHEKLFELILMEEIRFPRTLGPEAKSLLSGLLKKDPKQRLGGGSEDAKEIMQHRF
FAGIVWQHVYEKKLSPPFKPQVTSETDTRYFDEEFTAQMITITPPDQDDSMECVDSERRPHF
PQFSYSASGTA

WFH - First SH2 domain from SHP-2
NCA - Linker
WFH - Second SH2 domain from SHP-2
NTT - Linker
FEY - AKT protein kinase
RFF – Linker
AGI - AKT AGC-kinase C-terminal FIG. 14 (continued)

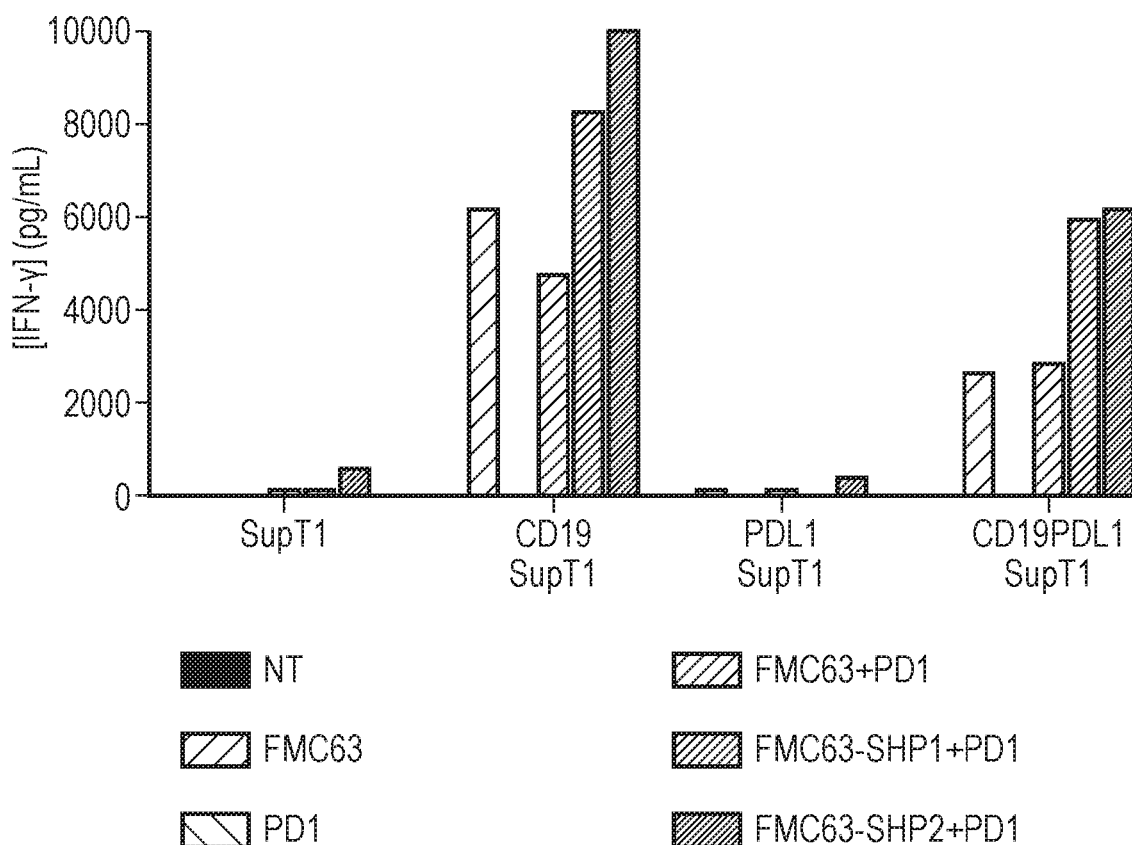

FIG. 15

SEQUENCE LISTING

<160> NUMBER OF SEQ ID NOS: 63

<210> SEQ ID NO 1
<211> LENGTH: 619
<212> TYPE: PRT
<213> ORGANISM: Homo sapiens

<400> SEQUENCE: 1

```
Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65              70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
    210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Ala Pro Thr Leu Pro Ala
            260                 265                 270

His Pro Ser Thr Leu Thr His Pro Gln Arg Arg Ile Asp Thr Leu Asn
        275                 280                 285

Ser Asp Gly Tyr Thr Pro Glu Pro Ala Arg Ile Thr Ser Pro Asp Lys
    290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Leu Phe Leu Lys Arg Asp Asn
                325                 330                 335

Leu Leu Ile Ala Asp Ile Glu Leu Gly Cys Gly Asn Phe Gly Ser Val
            340                 345                 350

Arg Gln Gly Val Tyr Arg Met Arg Lys Lys Gln Ile Asp Val Ala Ile
        355                 360                 365
```

```
Lys Val Leu Lys Gln Gly Thr Glu Lys Ala Asp Thr Glu Met Met
        370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Met Glu Met
                405                 410                 415

Ala Gly Gly Gly Pro Leu His Lys Phe Leu Val Gly Lys Arg Glu Glu
            420                 425                 430

Ile Pro Val Ser Asn Val Ala Glu Leu Leu His Gln Val Ser Met Gly
            435                 440                 445

Met Lys Tyr Leu Glu Glu Lys Asn Phe Val His Arg Asp Leu Ala Ala
    450                 455                 460

Arg Asn Val Leu Leu Val Asn Arg His Tyr Ala Lys Ile Ser Asp Phe
465                 470                 475                 480

Gly Leu Ser Lys Ala Leu Gly Ala Asp Asp Ser Tyr Tyr Thr Ala Arg
                485                 490                 495

Ser Ala Gly Lys Trp Pro Leu Lys Trp Tyr Ala Pro Glu Cys Ile Asn
            500                 505                 510

Phe Arg Lys Phe Ser Ser Arg Ser Asp Val Trp Ser Tyr Gly Val Thr
    515                 520                 525

Met Trp Glu Ala Leu Ser Tyr Gly Gln Lys Pro Tyr Lys Lys Met Lys
    530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
                565                 570                 575

Ile Tyr Lys Trp Glu Asp Arg Pro Asp Phe Leu Thr Val Glu Gln Arg
            580                 585                 590

Met Arg Ala Cys Tyr Tyr Ser Leu Ala Ser Lys Val Glu Gly Pro Pro
            595                 600                 605

Gly Ser Thr Gln Lys Ala Glu Ala Ala Cys Ala
            610                 615

<210> SEQ ID NO 2
<211> LENGTH: 280
<212> TYPE: PRT
<213> ORGANISM: Artificial Sequence
<220> FEATURE:
<223> OTHER INFORMATION: ZAP70 complete SH2 domain

<400> SEQUENCE: 2

Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110
```

```
Gly Val Phe Asp Cys Leu Arg Asp Ala Met Val Arg Asp Tyr Val Arg
            115                 120                 125

Gln Thr Trp Lys Leu Glu Gly Glu Ala Leu Glu Gln Ala Ile Ile Ser
130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
            165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
            195                 200                 205

Tyr His Tyr Leu Ile Ser Gln Asp Lys Ala Gly Lys Tyr Cys Ile Pro
            210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
            245                 250                 255

Ser Ser Ala Ser Asn Ala Ser Gly Ala Ala Pro Thr Leu Pro Ala
            260                 265                 270

His Pro Ser Thr Leu Thr His Pro
            275                 280

<210> SEQ ID NO 3
<211> LENGTH: 93
<212> TYPE: PRT
<213> ORGANISM: Artificial Sequence
<220> FEATURE:
<223> OTHER INFORMATION: ZAP70 SH2 1

<400> SEQUENCE: 3

Phe Phe Tyr Gly Ser Ile Ser Arg Ala Glu Ala Glu Glu His Leu Lys
1               5                   10                  15

Leu Ala Gly Met Ala Asp Gly Leu Phe Leu Leu Arg Gln Cys Leu Arg
            20                  25                  30

Ser Leu Gly Gly Tyr Val Leu Ser Leu Val His Asp Val Arg Phe His
            35                  40                  45

His Phe Pro Ile Glu Arg Gln Leu Asn Gly Thr Tyr Ala Ile Ala Gly
    50                  55                  60

Gly Lys Ala His Cys Gly Pro Ala Glu Leu Cys Glu Phe Tyr Ser Arg
65                  70                  75                  80

Asp Pro Asp Gly Leu Pro Cys Asn Leu Arg Lys Pro Cys
                85                  90

<210> SEQ ID NO 4
<211> LENGTH: 92
<212> TYPE: PRT
<213> ORGANISM: Artificial Sequence
<220> FEATURE:
<223> OTHER INFORMATION: ZAP70 SH2 2

<400> SEQUENCE: 4

Trp Tyr His Ser Ser Leu Thr Arg Glu Glu Ala Glu Arg Lys Leu Tyr
1               5                   10                  15

Ser Gly Ala Gln Thr Asp Gly Lys Phe Leu Leu Arg Pro Arg Lys Glu
            20                  25                  30

Gln Gly Thr Tyr Ala Leu Ser Leu Ile Tyr Gly Lys Thr Val Tyr His
            35                  40                  45
```

```
Tyr Leu Ile Ser Gln Asp Lys Ala Gly Lys Tyr Cys Ile Pro Glu Gly
        50                  55                  60

Thr Lys Phe Asp Thr Leu Trp Gln Leu Val Glu Tyr Leu Lys Leu Lys
65                  70                  75                  80

Ala Asp Gly Leu Ile Tyr Cys Leu Lys Glu Ala Cys
                85                  90

<210> SEQ ID NO 5
<211> LENGTH: 595
<212> TYPE: PRT
<213> ORGANISM: Homo sapiens

<400> SEQUENCE: 5

Met Val Arg Trp Phe His Arg Asp Leu Ser Gly Leu Asp Ala Glu Thr
1               5                   10                  15

Leu Leu Lys Gly Arg Gly Val His Gly Ser Phe Leu Ala Arg Pro Ser
            20                  25                  30

Arg Lys Asn Gln Gly Asp Phe Ser Leu Ser Val Arg Val Gly Asp Gln
        35                  40                  45

Val Thr His Ile Arg Ile Gln Asn Ser Gly Asp Phe Tyr Asp Leu Tyr
    50                  55                  60

Gly Gly Glu Lys Phe Ala Thr Leu Thr Glu Leu Val Glu Tyr Tyr Thr
65                  70                  75                  80

Gln Gln Gln Gly Val Leu Gln Asp Arg Asp Gly Thr Ile Ile His Leu
                85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125

Glu Pro Trp Thr Phe Leu Val Arg Glu Ser Leu Ser Gln Pro Gly Asp
    130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr Ala Thr Arg Val Asn Ala Ala Asp Ile Glu
    210                 215                 220

Asn Arg Val Leu Glu Leu Asn Lys Lys Gln Glu Ser Glu Asp Thr Ala
225                 230                 235                 240

Lys Ala Gly Phe Trp Glu Glu Phe Glu Ser Leu Gln Lys Gln Glu Val
                245                 250                 255

Lys Asn Leu His Gln Arg Leu Glu Gly Gln Arg Pro Glu Asn Lys Gly
            260                 265                 270

Lys Asn Arg Tyr Lys Asn Ile Leu Pro Phe Asp His Ser Arg Val Ile
        275                 280                 285

Leu Gln Gly Arg Asp Ser Asn Ile Pro Gly Ser Asp Tyr Ile Asn Ala
    290                 295                 300

Asn Tyr Ile Lys Asn Gln Leu Leu Gly Pro Asp Glu Asn Ala Lys Thr
305                 310                 315                 320

Tyr Ile Ala Ser Gln Gly Cys Leu Glu Ala Thr Val Asn Asp Phe Trp
```

```
                  325                 330                 335
Gln Met Ala Trp Gln Glu Asn Ser Arg Val Ile Val Met Thr Thr Arg
            340                 345                 350
Glu Val Glu Lys Gly Arg Asn Lys Cys Val Pro Tyr Trp Pro Glu Val
            355                 360                 365
Gly Met Gln Arg Ala Tyr Gly Pro Tyr Ser Val Thr Asn Cys Gly Glu
            370                 375                 380
His Asp Thr Thr Glu Tyr Lys Leu Arg Thr Leu Gln Val Ser Pro Leu
385                 390                 395                 400
Asp Asn Gly Asp Leu Ile Arg Glu Ile Trp His Tyr Gln Tyr Leu Ser
                405                 410                 415
Trp Pro Asp His Gly Val Pro Ser Glu Pro Gly Gly Val Leu Ser Phe
            420                 425                 430
Leu Asp Gln Ile Asn Gln Arg Gln Glu Ser Leu Pro His Ala Gly Pro
            435                 440                 445
Ile Ile Val His Cys Ser Ala Gly Ile Gly Arg Thr Gly Thr Ile Ile
            450                 455                 460
Val Ile Asp Met Leu Met Glu Asn Ile Ser Thr Lys Gly Leu Asp Cys
465                 470                 475                 480
Asp Ile Asp Ile Gln Lys Thr Ile Gln Met Val Arg Ala Gln Arg Ser
                485                 490                 495
Gly Met Val Gln Thr Glu Ala Gln Tyr Lys Phe Ile Tyr Val Ala Ile
            500                 505                 510
Ala Gln Phe Ile Glu Thr Thr Lys Lys Lys Leu Glu Val Leu Gln Ser
            515                 520                 525
Gln Lys Gly Gln Glu Ser Glu Tyr Gly Asn Ile Thr Tyr Pro Pro Ala
            530                 535                 540
Met Lys Asn Ala His Ala Lys Ala Ser Arg Thr Ser Lys His Lys
545                 550                 555                 560
Glu Asp Val Tyr Glu Asn Leu His Thr Lys Asn Lys Arg Glu Lys
                565                 570                 575
Val Lys Lys Gln Arg Ser Ala Asp Lys Glu Lys Ser Lys Gly Ser Leu
            580                 585                 590
Lys Arg Lys
        595

<210> SEQ ID NO 6
<211> LENGTH: 214
<212> TYPE: PRT
<213> ORGANISM: Artificial Sequence
<220> FEATURE:
<223> OTHER INFORMATION: PTPN6 SH2 complete domain

<400> SEQUENCE: 6

Met Val Arg Trp Phe His Arg Asp Leu Ser Gly Leu Asp Ala Glu Thr
1               5                   10                  15
Leu Leu Lys Gly Arg Gly Val His Gly Ser Phe Leu Ala Arg Pro Ser
            20                  25                  30
Arg Lys Asn Gln Gly Asp Phe Ser Leu Ser Val Arg Val Gly Asp Gln
        35                  40                  45
Val Thr His Ile Arg Ile Gln Asn Ser Gly Asp Phe Tyr Asp Leu Tyr
    50                  55                  60
Gly Gly Glu Lys Phe Ala Thr Leu Thr Glu Leu Val Glu Tyr Tyr Thr
65                  70                  75                  80
Gln Gln Gln Gly Val Leu Gln Asp Arg Asp Gly Thr Ile Ile His Leu
```

```
                        85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
            115                 120                 125

Glu Pro Trp Thr Phe Leu Val Arg Glu Ser Leu Ser Gln Pro Gly Asp
            130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
            195                 200                 205

Leu Arg Gln Pro Tyr Tyr
            210

<210> SEQ ID NO 7
<211> LENGTH: 97
<212> TYPE: PRT
<213> ORGANISM: Artificial Sequence
<220> FEATURE:
<223> OTHER INFORMATION: PTPN6 SH2 1

<400> SEQUENCE: 7

Trp Phe His Arg Asp Leu Ser Gly Leu Asp Ala Glu Thr Leu Leu Lys
1               5                   10                  15

Gly Arg Gly Val His Gly Ser Phe Leu Ala Arg Pro Ser Arg Lys Asn
            20                  25                  30

Gln Gly Asp Phe Ser Leu Ser Val Arg Val Gly Asp Gln Val Thr His
        35                  40                  45

Ile Arg Ile Gln Asn Ser Gly Asp Phe Tyr Asp Leu Tyr Gly Gly Glu
50                  55                  60

Lys Phe Ala Thr Leu Thr Glu Leu Val Glu Tyr Tyr Thr Gln Gln Gln
65                  70                  75                  80

Gly Val Leu Gln Asp Arg Asp Gly Thr Ile Ile His Leu Lys Tyr Pro
                85                  90                  95

Leu

<210> SEQ ID NO 8
<211> LENGTH: 104
<212> TYPE: PRT
<213> ORGANISM: Artificial Sequence
<220> FEATURE:
<223> OTHER INFORMATION: PTPN6 SH2 2

<400> SEQUENCE: 8

Trp Tyr His Gly His Met Ser Gly Gly Gln Ala Glu Thr Leu Leu Gln
1               5                   10                  15

Ala Lys Gly Glu Pro Trp Thr Phe Leu Val Arg Glu Ser Leu Ser Gln
            20                  25                  30

Pro Gly Asp Phe Val Leu Ser Val Leu Ser Asp Gln Pro Lys Ala Gly
        35                  40                  45

Pro Gly Ser Pro Leu Arg Val Thr His Ile Lys Val Met Cys Glu Gly
50                  55                  60

Gly Arg Tyr Thr Val Gly Gly Leu Glu Thr Phe Asp Ser Leu Thr Asp
```

```
                65                  70                  75                  80
Leu Val Glu His Phe Lys Lys Thr Gly Ile Glu Glu Ala Ser Gly Ala
                    85                  90                  95

Phe Val Tyr Leu Arg Gln Pro Tyr
                100

<210> SEQ ID NO 9
<211> LENGTH: 597
<212> TYPE: PRT
<213> ORGANISM: Homo sapiens

<400> SEQUENCE: 9

Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Arg
                20                  25                  30

Pro Ser Lys Ser Asn Pro Gly Asp Phe Thr Leu Ser Val Arg Arg Asn
            35                  40                  45

Gly Ala Val Thr His Ile Lys Ile Gln Asn Thr Gly Asp Tyr Tyr Asp
        50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
                100                 105                 110

Phe His Gly His Leu Ser Gly Lys Glu Ala Glu Lys Leu Leu Thr Glu
            115                 120                 125

Lys Gly Lys His Gly Ser Phe Leu Val Arg Glu Ser Gln Ser His Pro
        130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
                180                 185                 190

Leu Val Glu His Tyr Lys Lys Asn Pro Met Val Glu Thr Leu Gly Thr
            195                 200                 205

Val Leu Gln Leu Lys Gln Pro Leu Asn Thr Thr Arg Ile Asn Ala Ala
        210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
                260                 265                 270

Asn Lys Asn Lys Asn Arg Tyr Lys Asn Ile Leu Pro Phe Asp His Thr
            275                 280                 285

Arg Val Val Leu His Asp Gly Asp Pro Asn Glu Pro Val Ser Asp Tyr
        290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335
```

```
Thr Val Asn Asp Phe Trp Arg Met Val Phe Gln Glu Asn Ser Arg Val
                340                 345                 350

Ile Val Met Thr Thr Lys Glu Val Glu Arg Gly Lys Ser Lys Cys Val
            355                 360                 365

Lys Tyr Trp Pro Asp Glu Tyr Ala Leu Lys Glu Tyr Gly Val Met Arg
        370                 375                 380

Val Arg Asn Val Lys Glu Ser Ala Ala His Asp Tyr Thr Leu Arg Glu
385                 390                 395                 400

Leu Lys Leu Ser Lys Val Gly Gln Ala Leu Gln Gly Asn Thr Glu
                405                 410                 415

Arg Thr Val Trp Gln Tyr His Phe Arg Thr Trp Pro Asp His Gly Val
            420                 425                 430

Pro Ser Asp Pro Gly Gly Val Leu Asp Phe Leu Glu Glu Val His His
        435                 440                 445

Lys Gln Glu Ser Ile Val Asp Ala Gly Pro Val Val His Cys Ser
                450                 455                 460

Ala Gly Ile Gly Arg Thr Gly Thr Phe Ile Val Ile Asp Ile Leu Ile
465                 470                 475                 480

Asp Ile Ile Arg Glu Lys Gly Val Asp Cys Asp Ile Asp Val Pro Lys
                485                 490                 495

Thr Ile Gln Met Val Arg Ser Gln Arg Ser Gly Met Val Gln Thr Glu
            500                 505                 510

Ala Gln Tyr Arg Phe Ile Tyr Met Ala Val Gln His Tyr Ile Glu Thr
        515                 520                 525

Leu Gln Arg Arg Ile Glu Glu Gln Lys Ser Lys Arg Lys Gly His
            530                 535                 540

Glu Tyr Thr Asn Ile Lys Tyr Ser Leu Val Asp Gln Thr Ser Gly Asp
545                 550                 555                 560

Gln Ser Pro Leu Pro Pro Cys Thr Pro Thr Pro Cys Ala Glu Met
                565                 570                 575

Arg Glu Asp Ser Ala Arg Val Tyr Glu Asn Val Gly Leu Met Gln Gln
            580                 585                 590

Gln Arg Ser Phe Arg
        595

<210> SEQ ID NO 10
<211> LENGTH: 97
<212> TYPE: PRT
<213> ORGANISM: Artificial Sequence
<220> FEATURE:
<223> OTHER INFORMATION: SHP-2 first SH2 domain

<400> SEQUENCE: 10

Trp Phe His Pro Asn Ile Thr Gly Val Glu Ala Glu Asn Leu Leu Leu
1               5                   10                  15

Thr Arg Gly Val Asp Gly Ser Phe Leu Ala Arg Pro Ser Lys Ser Asn
            20                  25                  30

Pro Gly Asp Phe Thr Leu Ser Val Arg Arg Asn Gly Ala Val Thr His
        35                  40                  45

Ile Lys Ile Gln Asn Thr Gly Asp Tyr Tyr Asp Leu Tyr Gly Gly Glu
    50                  55                  60

Lys Phe Ala Thr Leu Ala Glu Leu Val Gln Tyr Tyr Met Glu His His
65                  70                  75                  80

Gly Gln Leu Lys Glu Lys Asn Gly Asp Val Ile Glu Leu Lys Tyr Pro
                85                  90                  95
```

Leu

<210> SEQ ID NO 11
<211> LENGTH: 105
<212> TYPE: PRT
<213> ORGANISM: Artificial Sequence
<220> FEATURE:
<223> OTHER INFORMATION: SHP-2 second SH2 domain

<400> SEQUENCE: 11

```
Trp Phe His Gly His Leu Ser Gly Lys Glu Ala Glu Lys Leu Leu Thr
1               5                   10                  15
Glu Lys Gly Lys His Gly Ser Phe Leu Val Arg Glu Ser Gln Ser His
            20                  25                  30
Pro Gly Asp Phe Val Leu Ser Val Arg Thr Gly Asp Asp Lys Gly Glu
        35                  40                  45
Ser Asn Asp Gly Lys Ser Lys Val Thr His Val Met Ile Arg Cys Gln
    50                  55                  60
Glu Leu Lys Tyr Asp Val Gly Gly Gly Glu Arg Phe Asp Ser Leu Thr
65                  70                  75                  80
Asp Leu Val Glu His Tyr Lys Lys Asn Pro Met Val Glu Thr Leu Gly
                85                  90                  95
Thr Val Leu Gln Leu Lys Gln Pro Leu
            100                 105
```

<210> SEQ ID NO 12
<211> LENGTH: 211
<212> TYPE: PRT
<213> ORGANISM: Artificial Sequence
<220> FEATURE:
<223> OTHER INFORMATION: SHP-2 both SH2 domains

<400> SEQUENCE: 12

```
Trp Phe His Pro Asn Ile Thr Gly Val Glu Ala Glu Asn Leu Leu Leu
1               5                   10                  15
Thr Arg Gly Val Asp Gly Ser Phe Leu Ala Arg Pro Ser Lys Ser Asn
            20                  25                  30
Pro Gly Asp Phe Thr Leu Ser Val Arg Arg Asn Gly Ala Val Thr His
        35                  40                  45
Ile Lys Ile Gln Asn Thr Gly Asp Tyr Tyr Asp Leu Tyr Gly Gly Glu
    50                  55                  60
Lys Phe Ala Thr Leu Ala Glu Leu Val Gln Tyr Tyr Met Glu His His
65                  70                  75                  80
Gly Gln Leu Lys Glu Lys Asn Gly Asp Val Ile Glu Leu Lys Tyr Pro
                85                  90                  95
Leu Asn Cys Ala Asp Pro Thr Ser Glu Arg Trp Phe His Gly His Leu
            100                 105                 110
Ser Gly Lys Glu Ala Glu Lys Leu Leu Thr Glu Lys Gly Lys His Gly
        115                 120                 125
Ser Phe Leu Val Arg Glu Ser Gln Ser His Pro Gly Asp Phe Val Leu
    130                 135                 140
Ser Val Arg Thr Gly Asp Asp Lys Gly Glu Ser Asn Asp Gly Lys Ser
145                 150                 155                 160
Lys Val Thr His Val Met Ile Arg Cys Gln Glu Leu Lys Tyr Asp Val
                165                 170                 175
Gly Gly Gly Glu Arg Phe Asp Ser Leu Thr Asp Leu Val Glu His Tyr
            180                 185                 190
```

Lys Lys Asn Pro Met Val Glu Thr Leu Gly Thr Val Leu Gln Leu Lys
        195                 200                 205

Gln Pro Leu
    210

<210> SEQ ID NO 13
<211> LENGTH: 112
<212> TYPE: PRT
<213> ORGANISM: Artificial Sequence
<220> FEATURE:
<223> OTHER INFORMATION: CD3-zeta endodomain

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 754
<212> TYPE: PRT
<213> ORGANISM: Artificial Sequence
<220> FEATURE:
<223> OTHER INFORMATION: ZAP70-SH2 domain fused to a CD3-zeta endodomain

<400> SEQUENCE: 14

Met Arg Arg Val Lys Phe Ser Arg Ser Ala Asp Ala Pro Ala Tyr Gln
1               5                   10                  15

Gln Gly Gln Asn Gln Leu Tyr Asn Glu Leu Asn Leu Gly Arg Arg Glu
            20                  25                  30

Glu Tyr Asp Val Leu Asp Lys Arg Arg Gly Arg Asp Pro Glu Met Gly
        35                  40                  45

Gly Lys Pro Arg Arg Lys Asn Pro Gln Glu Gly Leu Tyr Asn Glu Leu
    50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Tyr Gln Gly Leu Ser
                85                  90                  95

Thr Ala Thr Lys Asp Thr Tyr Asp Ala Leu His Met Gln Ala Leu Pro
            100                 105                 110

Pro Arg Ser Gly Gly Gly Gly Ser Gly Gly Gly Gly Ser Gly Gly Gly
        115                 120                 125

Gly Ser Gly Gly Gly Gly Ser Met Pro Asp Pro Ala Ala His Leu Pro
    130                 135                 140

Phe Phe Tyr Gly Ser Ile Ser Arg Ala Glu Ala Glu Glu His Leu Lys
145                 150                 155                 160

Leu Ala Gly Met Ala Asp Gly Leu Phe Leu Leu Arg Gln Cys Leu Arg
                165                 170                 175

-continued

Ser Leu Gly Gly Tyr Val Leu Ser Leu Val His Asp Val Arg Phe His
              180                 185                 190

His Phe Pro Ile Glu Arg Gln Leu Asn Gly Thr Tyr Ala Ile Ala Gly
            195                 200                 205

Gly Lys Ala His Cys Gly Pro Ala Glu Leu Cys Glu Phe Tyr Ser Arg
    210                 215                 220

Asp Pro Asp Gly Leu Pro Cys Asn Leu Arg Lys Pro Cys Asn Arg Pro
225                 230                 235                 240

Ser Gly Leu Glu Pro Gln Pro Gly Val Phe Asp Cys Leu Arg Asp Ala
                245                 250                 255

Met Val Arg Asp Tyr Val Arg Gln Thr Trp Lys Leu Glu Gly Glu Ala
            260                 265                 270

Leu Glu Gln Ala Ile Ile Ser Gln Ala Pro Gln Val Glu Lys Leu Ile
        275                 280                 285

Ala Thr Thr Ala His Glu Arg Met Pro Trp Tyr His Ser Ser Leu Thr
    290                 295                 300

Arg Glu Glu Ala Glu Arg Lys Leu Tyr Ser Gly Ala Gln Thr Asp Gly
305                 310                 315                 320

Lys Phe Leu Leu Arg Pro Arg Lys Glu Gln Gly Thr Tyr Ala Leu Ser
                325                 330                 335

Leu Ile Tyr Gly Lys Thr Val Tyr His Tyr Leu Ile Ser Gln Asp Lys
            340                 345                 350

Ala Gly Lys Tyr Cys Ile Pro Glu Gly Thr Lys Phe Asp Thr Leu Trp
        355                 360                 365

Gln Leu Val Glu Tyr Leu Lys Leu Lys Ala Asp Gly Leu Ile Tyr Cys
    370                 375                 380

Leu Lys Glu Ala Cys Pro Asn Ser Ser Ala Ser Asn Ala Ser Gly Ala
385                 390                 395                 400

Ala Ala Pro Thr Leu Pro Ala His Pro Ser Thr Leu Thr His Pro Gln
                405                 410                 415

Arg Arg Ile Asp Thr Leu Asn Ser Asp Gly Tyr Thr Pro Glu Pro Ala
            420                 425                 430

Arg Ile Thr Ser Pro Asp Lys Pro Arg Pro Met Pro Met Asp Thr Ser
        435                 440                 445

Val Tyr Glu Ser Pro Tyr Ser Asp Pro Glu Glu Leu Lys Asp Lys Lys
    450                 455                 460

Leu Phe Leu Lys Arg Asp Asn Leu Leu Ile Ala Asp Ile Glu Leu Gly
465                 470                 475                 480

Cys Gly Asn Phe Gly Ser Val Arg Gln Gly Val Tyr Arg Met Arg Lys
                485                 490                 495

Lys Gln Ile Asp Val Ala Ile Lys Val Leu Lys Gln Gly Thr Glu Lys
            500                 505                 510

Ala Asp Thr Glu Glu Met Met Arg Glu Ala Gln Ile Met His Gln Leu
        515                 520                 525

Asp Asn Pro Tyr Ile Val Arg Leu Ile Gly Val Cys Gln Ala Glu Ala
    530                 535                 540

Leu Met Leu Val Met Glu Met Ala Gly Gly Gly Pro Leu His Lys Phe
545                 550                 555                 560

Leu Val Gly Lys Arg Glu Glu Ile Pro Val Ser Asn Val Ala Glu Leu
                565                 570                 575

Leu His Gln Val Ser Met Gly Met Lys Tyr Leu Glu Glu Lys Asn Phe
            580                 585                 590

```
Val His Arg Asp Leu Ala Ala Arg Asn Val Leu Leu Val Asn Arg His
        595                 600                 605

Tyr Ala Lys Ile Ser Asp Phe Gly Leu Ser Lys Ala Leu Gly Ala Asp
610                 615                 620

Asp Ser Tyr Tyr Thr Ala Arg Ser Ala Gly Lys Trp Pro Leu Lys Trp
625                 630                 635                 640

Tyr Ala Pro Glu Cys Ile Asn Phe Arg Lys Phe Ser Ser Arg Ser Asp
                645                 650                 655

Val Trp Ser Tyr Gly Val Thr Met Trp Glu Ala Leu Ser Tyr Gly Gln
            660                 665                 670

Lys Pro Tyr Lys Lys Met Lys Gly Pro Glu Val Met Ala Phe Ile Glu
        675                 680                 685

Gln Gly Lys Arg Met Glu Cys Pro Pro Glu Cys Pro Pro Glu Leu Tyr
690                 695                 700

Ala Leu Met Ser Asp Cys Trp Ile Tyr Lys Trp Glu Asp Arg Pro Asp
705                 710                 715                 720

Phe Leu Thr Val Glu Gln Arg Met Arg Ala Cys Tyr Tyr Ser Leu Ala
                725                 730                 735

Ser Lys Val Glu Gly Pro Pro Gly Ser Thr Gln Lys Ala Glu Ala Ala
            740                 745                 750

Cys Ala

<210> SEQ ID NO 15
<211> LENGTH: 97
<212> TYPE: PRT
<213> ORGANISM: Artificial Sequence
<220> FEATURE:
<223> OTHER INFORMATION: PDCD1 endodomain

<400> SEQUENCE: 15

Cys Ser Arg Ala Ala Arg Gly Thr Ile Gly Ala Arg Arg Thr Gly Gln
1               5                   10                  15

Pro Leu Lys Glu Asp Pro Ser Ala Val Pro Val Phe Ser Val Asp Tyr
            20                  25                  30

Gly Glu Leu Asp Phe Gln Trp Arg Glu Lys Thr Pro Glu Pro Pro Val
        35                  40                  45

Pro Cys Val Pro Glu Gln Thr Glu Tyr Ala Thr Ile Val Phe Pro Ser
    50                  55                  60

Gly Met Gly Thr Ser Ser Pro Ala Arg Arg Gly Ser Ala Asp Gly Pro
65                  70                  75                  80

Arg Ser Ala Gln Pro Leu Arg Pro Glu Asp Gly His Cys Ser Trp Pro
                85                  90                  95

Leu

<210> SEQ ID NO 16
<211> LENGTH: 141
<212> TYPE: PRT
<213> ORGANISM: Artificial Sequence
<220> FEATURE:
<223> OTHER INFORMATION: BTLA4 endodomain

<400> SEQUENCE: 16

Lys Leu Gln Arg Arg Trp Lys Arg Thr Gln Ser Gln Gln Gly Leu Gln
1               5                   10                  15

Glu Asn Ser Ser Gly Gln Ser Phe Phe Val Arg Asn Lys Lys Val Arg
            20                  25                  30

Arg Ala Pro Leu Ser Glu Gly Pro His Ser Leu Gly Cys Tyr Asn Pro
```

```
                35                  40                  45
Met Met Glu Asp Gly Ile Ser Tyr Thr Thr Leu Arg Phe Pro Glu Met
 50                  55                  60

Asn Ile Pro Arg Thr Gly Asp Ala Glu Ser Ser Glu Met Gln Arg Pro
 65                  70                  75                  80

Pro Pro Asp Cys Asp Asp Thr Val Thr Tyr Ser Ala Leu His Lys Arg
                 85                  90                  95

Gln Val Gly Asp Tyr Glu Asn Val Ile Pro Asp Phe Pro Glu Asp Glu
                100                 105                 110

Gly Ile His Tyr Ser Glu Leu Ile Gln Phe Gly Val Gly Glu Arg Pro
            115                 120                 125

Gln Ala Gln Glu Asn Val Asp Tyr Val Ile Leu Lys His
        130                 135                 140

<210> SEQ ID NO 17
<211> LENGTH: 168
<212> TYPE: PRT
<213> ORGANISM: Artificial Sequence
<220> FEATURE:
<223> OTHER INFORMATION: LILRB1 endodomain

<400> SEQUENCE: 17

Leu Arg His Arg Arg Gln Gly Lys His Trp Thr Ser Thr Gln Arg Lys
 1               5                  10                  15

Ala Asp Phe Gln His Pro Ala Gly Ala Val Gly Pro Glu Pro Thr Asp
                20                  25                  30

Arg Gly Leu Gln Trp Arg Ser Ser Pro Ala Ala Asp Ala Gln Glu Glu
            35                  40                  45

Asn Leu Tyr Ala Ala Val Lys His Thr Gln Pro Glu Asp Gly Val Glu
 50                  55                  60

Met Asp Thr Arg Ser Pro His Asp Glu Asp Pro Gln Ala Val Thr Tyr
 65                  70                  75                  80

Ala Glu Val Lys His Ser Arg Pro Arg Arg Glu Met Ala Ser Pro Pro
                 85                  90                  95

Ser Pro Leu Ser Gly Glu Phe Leu Asp Thr Lys Asp Arg Gln Ala Glu
                100                 105                 110

Glu Asp Arg Gln Met Asp Thr Glu Ala Ala Ala Ser Glu Ala Pro Gln
            115                 120                 125

Asp Val Thr Tyr Ala Gln Leu His Ser Leu Thr Leu Arg Arg Glu Ala
        130                 135                 140

Thr Glu Pro Pro Pro Ser Gln Glu Gly Pro Ser Pro Ala Val Pro Ser
145                 150                 155                 160

Ile Tyr Ala Thr Leu Ala Ile His
                165

<210> SEQ ID NO 18
<211> LENGTH: 101
<212> TYPE: PRT
<213> ORGANISM: Artificial Sequence
<220> FEATURE:
<223> OTHER INFORMATION: LAIR1 endodomain

<400> SEQUENCE: 18

His Arg Gln Asn Gln Ile Lys Gln Gly Pro Pro Arg Ser Lys Asp Glu
 1               5                  10                  15

Glu Gln Lys Pro Gln Gln Arg Pro Asp Leu Ala Val Asp Val Leu Glu
                20                  25                  30
```

Arg Thr Ala Asp Lys Ala Thr Val Asn Gly Leu Pro Glu Lys Asp Arg
            35                  40                  45

Glu Thr Asp Thr Ser Ala Leu Ala Ala Gly Ser Ser Gln Glu Val Thr
 50                  55                  60

Tyr Ala Gln Leu Asp His Trp Ala Leu Thr Gln Arg Thr Ala Arg Ala
 65                  70                  75                  80

Val Ser Pro Gln Ser Thr Lys Pro Met Ala Glu Ser Ile Thr Tyr Ala
                85                  90                  95

Ala Val Ala Arg His
            100

<210> SEQ ID NO 19
<211> LENGTH: 62
<212> TYPE: PRT
<213> ORGANISM: Artificial Sequence
<220> FEATURE:
<223> OTHER INFORMATION: CTLA4 endodomain

<400> SEQUENCE: 19

Phe Leu Leu Trp Ile Leu Ala Ala Val Ser Ser Gly Leu Phe Phe Tyr
 1               5                  10                  15

Ser Phe Leu Leu Thr Ala Val Ser Leu Ser Lys Met Leu Lys Lys Arg
                20                  25                  30

Ser Pro Leu Thr Thr Gly Val Tyr Val Lys Met Pro Pro Thr Glu Pro
            35                  40                  45

Glu Cys Glu Lys Gln Phe Gln Pro Tyr Phe Ile Pro Ile Asn
 50                  55                  60

<210> SEQ ID NO 20
<211> LENGTH: 111
<212> TYPE: PRT
<213> ORGANISM: Artificial Sequence
<220> FEATURE:
<223> OTHER INFORMATION: KIR2DL1 endodomain

<400> SEQUENCE: 20

Gly Asn Ser Arg His Leu His Val Leu Ile Gly Thr Ser Val Val Ile
 1               5                  10                  15

Ile Pro Phe Ala Ile Leu Leu Phe Phe Leu Leu His Arg Trp Cys Ala
                20                  25                  30

Asn Lys Lys Asn Ala Val Val Met Asp Gln Glu Pro Ala Gly Asn Arg
            35                  40                  45

Thr Val Asn Arg Glu Asp Ser Asp Glu Gln Asp Pro Gln Glu Val Thr
 50                  55                  60

Tyr Thr Gln Leu Asn His Cys Val Phe Thr Gln Arg Lys Ile Thr Arg
 65                  70                  75                  80

Pro Ser Gln Arg Pro Lys Thr Pro Pro Thr Asp Ile Ile Val Tyr Thr
                85                  90                  95

Glu Leu Pro Asn Ala Glu Ser Arg Ser Lys Val Val Ser Cys Pro
            100                 105                 110

<210> SEQ ID NO 21
<211> LENGTH: 143
<212> TYPE: PRT
<213> ORGANISM: Artificial Sequence
<220> FEATURE:
<223> OTHER INFORMATION: KIR2DL4 endodomain

<400> SEQUENCE: 21

Gly Ile Ala Arg His Leu His Ala Val Ile Arg Tyr Ser Val Ala Ile
 1               5                  10                  15

```
1               5                   10                  15
Ile Leu Phe Thr Ile Leu Pro Phe Phe Leu Leu His Arg Trp Cys Ser
                20                  25                  30

Lys Lys Lys Glu Asn Ala Ala Val Met Asn Gln Glu Pro Ala Gly His
            35                  40                  45

Arg Thr Val Asn Arg Glu Asp Ser Asp Glu Gln Asp Pro Gln Glu Val
        50                  55                  60

Thr Tyr Ala Gln Leu Asp His Cys Ile Phe Thr Gln Arg Lys Ile Thr
65                  70                  75                  80

Gly Pro Ser Gln Arg Ser Lys Arg Pro Ser Thr Asp Thr Ser Val Cys
                85                  90                  95

Ile Glu Leu Pro Asn Ala Glu Pro Arg Ala Leu Ser Pro Ala His Glu
                100                 105                 110

His His Ser Gln Ala Leu Met Gly Ser Ser Arg Glu Thr Thr Ala Leu
            115                 120                 125

Ser Gln Thr Gln Leu Ala Ser Ser Asn Val Pro Ala Ala Gly Ile
        130                 135                 140
```

<210> SEQ ID NO 22
<211> LENGTH: 143
<212> TYPE: PRT
<213> ORGANISM: Artificial Sequence
<220> FEATURE:
<223> OTHER INFORMATION: KIR2DL5 endodomain

<400> SEQUENCE: 22

```
Thr Gly Ile Arg Arg His Leu His Ile Leu Ile Gly Thr Ser Val Ala
1               5                   10                  15

Ile Ile Leu Phe Ile Ile Leu Phe Phe Leu Leu His Cys Cys Cys
                20                  25                  30

Ser Asn Lys Lys Asn Ala Ala Val Met Asp Gln Glu Pro Ala Gly Asp
            35                  40                  45

Arg Thr Val Asn Arg Glu Asp Ser Asp Gln Asp Pro Gln Glu Val
        50                  55                  60

Thr Tyr Ala Gln Leu Asp His Cys Val Phe Thr Gln Thr Lys Ile Thr
65                  70                  75                  80

Ser Pro Ser Gln Arg Pro Lys Thr Pro Pro Thr Asp Thr Thr Met Tyr
                85                  90                  95

Met Glu Leu Pro Asn Ala Lys Pro Arg Ser Leu Ser Pro Ala His Lys
                100                 105                 110

His His Ser Gln Ala Leu Arg Gly Ser Ser Arg Glu Thr Thr Ala Leu
            115                 120                 125

Ser Gln Asn Arg Val Ala Ser Ser His Val Pro Ala Ala Gly Ile
        130                 135                 140
```

<210> SEQ ID NO 23
<211> LENGTH: 111
<212> TYPE: PRT
<213> ORGANISM: Artificial Sequence
<220> FEATURE:
<223> OTHER INFORMATION: KIR3DL1 endodomain

<400> SEQUENCE: 23

```
Lys Asp Pro Arg His Leu His Ile Leu Ile Gly Thr Ser Val Val Ile
1               5                   10                  15

Ile Leu Phe Ile Leu Leu Leu Phe Phe Leu Leu His Leu Trp Cys Ser
                20                  25                  30
```

Asn Lys Lys Asn Ala Ala Val Met Asp Gln Glu Pro Ala Gly Asn Arg
                35                  40                  45

Thr Ala Asn Ser Glu Asp Ser Asp Glu Gln Asp Pro Glu Glu Val Thr
 50                  55                  60

Tyr Ala Gln Leu Asp His Cys Val Phe Thr Gln Arg Lys Ile Thr Arg
 65                  70                  75                  80

Pro Ser Gln Arg Pro Lys Thr Pro Thr Asp Thr Ile Leu Tyr Thr
                85                  90                  95

Glu Leu Pro Asn Ala Lys Pro Arg Ser Lys Val Val Ser Cys Pro
                100                 105                 110

<210> SEQ ID NO 24
<211> LENGTH: 97
<212> TYPE: PRT
<213> ORGANISM: Artificial Sequence
<220> FEATURE:
<223> OTHER INFORMATION: KIR3DL3 endodomain

<400> SEQUENCE: 24

Lys Asp Pro Gly Asn Ser Arg His Leu His Val Leu Ile Gly Thr Ser
 1                5                  10                  15

Val Val Ile Ile Pro Phe Ala Ile Leu Leu Phe Phe Leu Leu His Arg
                20                  25                  30

Trp Cys Ala Asn Lys Lys Asn Ala Val Val Met Asp Gln Glu Pro Ala
                35                  40                  45

Gly Asn Arg Thr Val Asn Arg Glu Asp Ser Asp Glu Gln Asp Pro Gln
 50                  55                  60

Glu Val Thr Tyr Ala Gln Leu Asn His Cys Val Phe Thr Gln Arg Lys
 65                  70                  75                  80

Ile Thr Arg Pro Ser Gln Arg Pro Lys Thr Pro Pro Thr Asp Thr Ser
                85                  90                  95

Val

<210> SEQ ID NO 25
<211> LENGTH: 701
<212> TYPE: PRT
<213> ORGANISM: Artificial Sequence
<220> FEATURE:
<223> OTHER INFORMATION: PTPN6-SH2 domain fused to a PD1 endodomain

<400> SEQUENCE: 25

Met Thr Gly Gln Pro Leu Lys Glu Asp Pro Ser Ala Val Pro Val Phe
 1                5                  10                  15

Ser Val Asp Tyr Gly Glu Leu Asp Phe Gln Trp Arg Glu Lys Thr Pro
                20                  25                  30

Glu Pro Pro Val Pro Cys Val Pro Glu Gln Thr Glu Tyr Ala Thr Ile
                35                  40                  45

Val Phe Pro Ser Gly Met Gly Thr Ser Ser Pro Ala Arg Arg Gly Ser
 50                  55                  60

Ala Asp Gly Pro Arg Ser Ala Gln Pro Leu Arg Pro Glu Asp Gly His
 65                  70                  75                  80

Cys Ser Trp Pro Leu Ser Gly Gly Gly Ser Gly Gly Gly Gly Ser
                85                  90                  95

Gly Gly Gly Gly Ser Gly Gly Gly Ser Met Val Arg Trp Phe His
                100                 105                 110

Arg Asp Leu Ser Gly Leu Asp Ala Glu Thr Leu Leu Lys Gly Arg Gly
                115                 120                 125

-continued

```
Val His Gly Ser Phe Leu Ala Arg Pro Ser Arg Lys Asn Gln Gly Asp
    130                 135                 140
Phe Ser Leu Ser Val Arg Val Gly Asp Gln Val Thr His Ile Arg Ile
145                 150                 155                 160
Gln Asn Ser Gly Asp Phe Tyr Asp Leu Tyr Gly Gly Glu Lys Phe Ala
                165                 170                 175
Thr Leu Thr Glu Leu Val Glu Tyr Tyr Thr Gln Gln Gln Gly Val Leu
            180                 185                 190
Gln Asp Arg Asp Gly Thr Ile Ile His Leu Lys Tyr Pro Leu Asn Cys
        195                 200                 205
Ser Asp Pro Thr Ser Glu Arg Trp Tyr His Gly His Met Ser Gly Gly
210                 215                 220
Gln Ala Glu Thr Leu Leu Gln Ala Lys Gly Glu Pro Trp Thr Phe Leu
225                 230                 235                 240
Val Arg Glu Ser Leu Ser Gln Pro Gly Asp Phe Val Leu Ser Val Leu
                245                 250                 255
Ser Asp Gln Pro Lys Ala Gly Pro Gly Ser Pro Leu Arg Val Thr His
            260                 265                 270
Ile Lys Val Met Cys Glu Gly Gly Arg Tyr Thr Val Gly Gly Leu Glu
        275                 280                 285
Thr Phe Asp Ser Leu Thr Asp Leu Val Glu His Phe Lys Lys Thr Gly
290                 295                 300
Ile Glu Glu Ala Ser Gly Ala Phe Val Tyr Leu Arg Gln Pro Tyr Tyr
305                 310                 315                 320
Ala Thr Arg Val Asn Ala Ala Asp Ile Glu Asn Arg Val Leu Glu Leu
                325                 330                 335
Asn Lys Lys Gln Glu Ser Glu Asp Thr Ala Lys Ala Gly Phe Trp Glu
            340                 345                 350
Glu Phe Glu Ser Leu Gln Lys Gln Glu Val Lys Asn Leu His Gln Arg
        355                 360                 365
Leu Glu Gly Gln Arg Pro Glu Asn Lys Gly Lys Asn Arg Tyr Lys Asn
370                 375                 380
Ile Leu Pro Phe Asp His Ser Arg Val Ile Leu Gln Gly Arg Asp Ser
385                 390                 395                 400
Asn Ile Pro Gly Ser Asp Tyr Ile Asn Ala Asn Tyr Ile Lys Asn Gln
                405                 410                 415
Leu Leu Gly Pro Asp Glu Asn Ala Lys Thr Tyr Ile Ala Ser Gln Gly
            420                 425                 430
Cys Leu Glu Ala Thr Val Asn Asp Phe Trp Gln Met Ala Trp Gln Glu
        435                 440                 445
Asn Ser Arg Val Ile Val Met Thr Thr Arg Glu Val Glu Lys Gly Arg
450                 455                 460
Asn Lys Cys Val Pro Tyr Trp Pro Glu Val Gly Met Gln Arg Ala Tyr
465                 470                 475                 480
Gly Pro Tyr Ser Val Thr Asn Cys Gly Glu His Asp Thr Thr Glu Tyr
                485                 490                 495
Lys Leu Arg Thr Leu Gln Val Ser Pro Leu Asp Asn Gly Asp Leu Ile
            500                 505                 510
Arg Glu Ile Trp His Tyr Gln Tyr Leu Ser Trp Pro Asp His Gly Val
        515                 520                 525
Pro Ser Glu Pro Gly Gly Val Leu Ser Phe Leu Asp Gln Ile Asn Gln
530                 535                 540
Arg Gln Glu Ser Leu Pro His Ala Gly Pro Ile Ile Val His Cys Ser
```

```
                545                 550                 555                 560
Ala Gly Ile Gly Arg Thr Gly Thr Ile Ile Val Ile Asp Met Leu Met
                    565                 570                 575

Glu Asn Ile Ser Thr Lys Gly Leu Asp Cys Asp Ile Asp Ile Gln Lys
                580                 585                 590

Thr Ile Gln Met Val Arg Ala Gln Arg Ser Gly Met Val Gln Thr Glu
                595                 600                 605

Ala Gln Tyr Lys Phe Ile Tyr Val Ala Ile Ala Gln Phe Ile Glu Thr
            610                 615                 620

Thr Lys Lys Lys Leu Glu Val Leu Gln Ser Gln Lys Gly Gln Glu Ser
625                 630                 635                 640

Glu Tyr Gly Asn Ile Thr Tyr Pro Pro Ala Met Lys Asn Ala His Ala
                    645                 650                 655

Lys Ala Ser Arg Thr Ser Ser Lys His Lys Glu Asp Val Tyr Glu Asn
                660                 665                 670

Leu His Thr Lys Asn Lys Arg Glu Gly Lys Val Lys Lys Gln Arg Ser
                675                 680                 685

Ala Asp Lys Glu Lys Ser Lys Gly Ser Leu Lys Arg Lys
            690                 695                 700

<210> SEQ ID NO 26
<211> LENGTH: 299
<212> TYPE: PRT
<213> ORGANISM: Artificial Sequence
<220> FEATURE:
<223> OTHER INFORMATION: ZAP70 kinase domain

<400> SEQUENCE: 26

Asp Pro Glu Glu Leu Lys Asp Lys Lys Leu Phe Leu Lys Arg Asp Asn
1               5                   10                  15

Leu Leu Ile Ala Asp Ile Glu Leu Gly Cys Gly Asn Phe Gly Ser Val
                20                  25                  30

Arg Gln Gly Val Tyr Arg Met Arg Lys Lys Gln Ile Asp Val Ala Ile
            35                  40                  45

Lys Val Leu Lys Gln Gly Thr Glu Lys Ala Asp Thr Glu Glu Met Met
        50                  55                  60

Arg Glu Ala Gln Ile Met His Gln Leu Asp Asn Pro Tyr Ile Val Arg
65                  70                  75                  80

Leu Ile Gly Val Cys Gln Ala Glu Ala Leu Met Leu Val Met Glu Met
                85                  90                  95

Ala Gly Gly Gly Pro Leu His Lys Phe Leu Val Gly Lys Arg Glu Glu
            100                 105                 110

Ile Pro Val Ser Asn Val Ala Glu Leu Leu His Gln Val Ser Met Gly
        115                 120                 125

Met Lys Tyr Leu Glu Glu Lys Asn Phe Val His Arg Asp Leu Ala Ala
        130                 135                 140

Arg Asn Val Leu Leu Val Asn Arg His Tyr Ala Lys Ile Ser Asp Phe
145                 150                 155                 160

Gly Leu Ser Lys Ala Leu Gly Ala Asp Asp Ser Tyr Tyr Thr Ala Arg
                165                 170                 175

Ser Ala Gly Lys Trp Pro Leu Lys Trp Tyr Ala Pro Glu Cys Ile Asn
            180                 185                 190

Phe Arg Lys Phe Ser Ser Arg Ser Asp Val Trp Ser Tyr Gly Val Thr
        195                 200                 205

Met Trp Glu Ala Leu Ser Tyr Gly Gln Lys Pro Tyr Lys Lys Met Lys
```

```
            210                 215                 220
Gly Pro Glu Val Met Ala Phe Ile Glu Gln Gly Lys Arg Met Glu Cys
225                 230                 235                 240

Pro Pro Glu Cys Pro Pro Glu Leu Tyr Ala Leu Met Ser Asp Cys Trp
                245                 250                 255

Ile Tyr Lys Trp Glu Asp Arg Pro Asp Phe Leu Thr Val Glu Gln Arg
                260                 265                 270

Met Arg Ala Cys Tyr Tyr Ser Leu Ala Ser Lys Val Glu Gly Pro Pro
                275                 280                 285

Gly Ser Thr Gln Lys Ala Glu Ala Ala Cys Ala
                290                 295
```

<210> SEQ ID NO 27
<211> LENGTH: 280
<212> TYPE: PRT
<213> ORGANISM: Artificial Sequence
<220> FEATURE:
<223> OTHER INFORMATION: PTPN6 phosphatase domain

<400> SEQUENCE: 27

```
Phe Trp Glu Glu Phe Glu Ser Leu Gln Lys Gln Glu Val Lys Asn Leu
1               5                   10                  15

His Gln Arg Leu Glu Gly Gln Arg Pro Glu Asn Lys Gly Lys Asn Arg
                20                  25                  30

Tyr Lys Asn Ile Leu Pro Phe Asp His Ser Arg Val Ile Leu Gln Gly
                35                  40                  45

Arg Asp Ser Asn Ile Pro Gly Ser Asp Tyr Ile Asn Ala Asn Tyr Ile
50                  55                  60

Lys Asn Gln Leu Leu Gly Pro Asp Glu Asn Ala Lys Thr Tyr Ile Ala
65                  70                  75                  80

Ser Gln Gly Cys Leu Glu Ala Thr Val Asn Asp Phe Trp Gln Met Ala
                85                  90                  95

Trp Gln Glu Asn Ser Arg Val Ile Val Met Thr Thr Arg Glu Val Glu
                100                 105                 110

Lys Gly Arg Asn Lys Cys Val Pro Tyr Trp Pro Glu Val Gly Met Gln
                115                 120                 125

Arg Ala Tyr Gly Pro Tyr Ser Val Thr Asn Cys Gly Glu His Asp Thr
                130                 135                 140

Thr Glu Tyr Lys Leu Arg Thr Leu Gln Val Ser Pro Leu Asp Asn Gly
145                 150                 155                 160

Asp Leu Ile Arg Glu Ile Trp His Tyr Gln Tyr Leu Ser Trp Pro Asp
                165                 170                 175

His Gly Val Pro Ser Glu Pro Gly Gly Val Leu Ser Phe Leu Asp Gln
                180                 185                 190

Ile Asn Gln Arg Gln Glu Ser Leu Pro His Ala Gly Pro Ile Ile Val
                195                 200                 205

His Cys Ser Ala Gly Ile Gly Arg Thr Gly Thr Ile Ile Val Ile Asp
                210                 215                 220

Met Leu Met Glu Asn Ile Ser Thr Lys Gly Leu Asp Cys Asp Ile Asp
225                 230                 235                 240

Ile Gln Lys Thr Ile Gln Met Val Arg Ala Gln Arg Ser Gly Met Val
                245                 250                 255

Gln Thr Glu Ala Gln Tyr Lys Phe Ile Tyr Val Ala Ile Ala Gln Phe
                260                 265                 270

Ile Glu Thr Thr Lys Lys Lys Leu
```

<210> SEQ ID NO 28
<211> LENGTH: 274
<212> TYPE: PRT
<213> ORGANISM: Artificial Sequence
<220> FEATURE:
<223> OTHER INFORMATION: SHP-2 phosphatase domain

<400> SEQUENCE: 28

```
Trp Glu Glu Phe Glu Thr Leu Gln Gln Gln Glu Cys Lys Leu Leu Tyr
1               5                   10                  15

Ser Arg Lys Glu Gly Gln Arg Gln Glu Asn Lys Asn Lys Asn Arg Tyr
            20                  25                  30

Lys Asn Ile Leu Pro Phe Asp His Thr Arg Val Val Leu His Asp Gly
        35                  40                  45

Asp Pro Asn Glu Pro Val Ser Asp Tyr Ile Asn Ala Asn Ile Ile Met
    50                  55                  60

Pro Glu Phe Glu Thr Lys Cys Asn Asn Ser Lys Pro Lys Lys Ser Tyr
65                  70                  75                  80

Ile Ala Thr Gln Gly Cys Leu Gln Asn Thr Val Asn Asp Phe Trp Arg
                85                  90                  95

Met Val Phe Gln Glu Asn Ser Arg Val Ile Val Met Thr Thr Lys Glu
            100                 105                 110

Val Glu Arg Gly Lys Ser Lys Cys Val Lys Tyr Trp Pro Asp Glu Tyr
        115                 120                 125

Ala Leu Lys Glu Tyr Gly Val Met Arg Val Arg Asn Val Lys Glu Ser
    130                 135                 140

Ala Ala His Asp Tyr Thr Leu Arg Glu Leu Lys Leu Ser Lys Val Gly
145                 150                 155                 160

Gln Ala Leu Leu Gln Gly Asn Thr Glu Arg Thr Val Trp Gln Tyr His
                165                 170                 175

Phe Arg Thr Trp Pro Asp His Gly Val Pro Ser Asp Pro Gly Gly Val
            180                 185                 190

Leu Asp Phe Leu Glu Glu Val His His Lys Gln Glu Ser Ile Met Asp
        195                 200                 205

Ala Gly Pro Val Val Val His Cys Ser Ala Gly Ile Gly Arg Thr Gly
    210                 215                 220

Thr Phe Ile Val Ile Asp Ile Leu Ile Asp Ile Ile Arg Glu Lys Gly
225                 230                 235                 240

Val Asp Cys Asp Ile Asp Val Pro Lys Thr Ile Gln Met Val Arg Ser
                245                 250                 255

Gln Arg Ser Gly Met Val Gln Thr Glu Ala Gln Tyr Arg Phe Ile Tyr
            260                 265                 270

Met Ala
```

<210> SEQ ID NO 29
<211> LENGTH: 519
<212> TYPE: PRT
<213> ORGANISM: Artificial Sequence
<220> FEATURE:
<223> OTHER INFORMATION: PTPN6 SH2 domain fusion: ZAP70 kinase domain

<400> SEQUENCE: 29

```
Met Val Arg Trp Phe His Arg Asp Leu Ser Gly Leu Asp Ala Glu Thr
1               5                   10                  15

Leu Leu Lys Gly Arg Gly Val His Gly Ser Phe Leu Ala Arg Pro Ser
```

```
                    20                  25                  30
Arg Lys Asn Gln Gly Asp Phe Ser Leu Ser Val Arg Val Gly Asp Gln
                35                  40                  45
Val Thr His Ile Arg Ile Gln Asn Ser Gly Asp Phe Tyr Asp Leu Tyr
            50                  55                  60
Gly Gly Glu Lys Phe Ala Thr Leu Thr Glu Leu Val Glu Tyr Tyr Thr
65                  70                  75                  80
Gln Gln Gln Gly Val Leu Gln Asp Arg Asp Gly Thr Ile Ile His Leu
                85                  90                  95
Lys Tyr Pro Leu Asn Cys Ser Asp Pro Thr Ser Glu Arg Trp Tyr His
                100                 105                 110
Gly His Met Ser Gly Gly Gln Ala Glu Thr Leu Leu Gln Ala Lys Gly
            115                 120                 125
Glu Pro Trp Thr Phe Leu Val Arg Glu Ser Leu Ser Gln Pro Gly Asp
            130                 135                 140
Phe Val Leu Ser Val Leu Ser Asp Gln Pro Lys Ala Gly Pro Gly Ser
145                 150                 155                 160
Pro Leu Arg Val Thr His Ile Lys Val Met Cys Glu Gly Gly Arg Tyr
                165                 170                 175
Thr Val Gly Gly Leu Glu Thr Phe Asp Ser Leu Thr Asp Leu Val Glu
                180                 185                 190
His Phe Lys Lys Thr Gly Ile Glu Glu Ala Ser Gly Ala Phe Val Tyr
            195                 200                 205
Leu Arg Gln Pro Tyr Tyr Ser Gly Gly Gly Ser Asp Pro Glu Glu
            210                 215                 220
Leu Lys Asp Lys Lys Leu Phe Leu Lys Arg Asp Asn Leu Leu Ile Ala
225                 230                 235                 240
Asp Ile Glu Leu Gly Cys Gly Asn Phe Gly Ser Val Arg Gln Gly Val
                245                 250                 255
Tyr Arg Met Arg Lys Lys Gln Ile Asp Val Ala Ile Lys Val Leu Lys
                260                 265                 270
Gln Gly Thr Glu Lys Ala Asp Thr Glu Glu Met Met Arg Glu Ala Gln
            275                 280                 285
Ile Met His Gln Leu Asp Asn Pro Tyr Ile Val Arg Leu Ile Gly Val
            290                 295                 300
Cys Gln Ala Glu Ala Leu Met Leu Val Met Glu Met Ala Gly Gly Gly
305                 310                 315                 320
Pro Leu His Lys Phe Leu Val Gly Lys Arg Glu Glu Ile Pro Val Ser
                325                 330                 335
Asn Val Ala Glu Leu Leu His Gln Val Ser Met Gly Met Lys Tyr Leu
            340                 345                 350
Glu Glu Lys Asn Phe Val His Arg Asp Leu Ala Ala Arg Asn Val Leu
            355                 360                 365
Leu Val Asn Arg His Tyr Ala Lys Ile Ser Asp Phe Gly Leu Ser Lys
            370                 375                 380
Ala Leu Gly Ala Asp Asp Ser Tyr Tyr Thr Ala Arg Ser Ala Gly Lys
385                 390                 395                 400
Trp Pro Leu Lys Trp Tyr Ala Pro Glu Cys Ile Asn Phe Arg Lys Phe
                405                 410                 415
Ser Ser Arg Ser Asp Val Trp Ser Tyr Gly Val Thr Met Trp Glu Ala
                420                 425                 430
Leu Ser Tyr Gly Gln Lys Pro Tyr Lys Lys Met Lys Gly Pro Glu Val
            435                 440                 445
```

```
Met Ala Phe Ile Glu Gln Gly Lys Arg Met Glu Cys Pro Pro Glu Cys
    450                 455                 460

Pro Pro Glu Leu Tyr Ala Leu Met Ser Asp Cys Trp Ile Tyr Lys Trp
465                 470                 475                 480

Glu Asp Arg Pro Asp Phe Leu Thr Val Glu Gln Arg Met Arg Ala Cys
                485                 490                 495

Tyr Tyr Ser Leu Ala Ser Lys Val Glu Gly Pro Pro Gly Ser Thr Gln
            500                 505                 510

Lys Ala Glu Ala Ala Cys Ala
            515

<210> SEQ ID NO 30
<211> LENGTH: 581
<212> TYPE: PRT
<213> ORGANISM: Artificial Sequence
<220> FEATURE:
<223> OTHER INFORMATION: ZAP70 SH2 domain fusion: PTPN6 phosphatase
      domain

<400> SEQUENCE: 30

Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45

Ser Leu Val His Asp Val Arg Phe His His Phe Pro Ile Glu Arg Gln
50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
130                 135                 140

Gln Ala Pro Gln Val Glu Lys Leu Ile Ala Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Ala Pro Thr Leu Pro Ala
            260                 265                 270

His Pro Ser Thr Leu Thr His Pro Ser Gly Gly Gly Gly Ser Gly Gly
```

```
                275                 280                 285
Gly Gly Ser Gly Gly Gly Ser Gly Gly Gly Ser Phe Trp Glu
    290                 295                 300

Glu Phe Glu Ser Leu Gln Lys Gln Glu Val Lys Asn Leu His Gln Arg
305                 310                 315                 320

Leu Glu Gly Gln Arg Pro Glu Asn Lys Gly Lys Asn Arg Tyr Lys Asn
                325                 330                 335

Ile Leu Pro Phe Asp His Ser Arg Val Ile Leu Gln Gly Arg Asp Ser
            340                 345                 350

Asn Ile Pro Gly Ser Asp Tyr Ile Asn Ala Asn Tyr Ile Lys Asn Gln
        355                 360                 365

Leu Leu Gly Pro Asp Glu Asn Ala Lys Thr Tyr Ile Ala Ser Gln Gly
    370                 375                 380

Cys Leu Glu Ala Thr Val Asn Asp Phe Trp Gln Met Ala Trp Gln Glu
385                 390                 395                 400

Asn Ser Arg Val Ile Val Met Thr Thr Arg Glu Val Glu Lys Gly Arg
                405                 410                 415

Asn Lys Cys Val Pro Tyr Trp Pro Glu Val Gly Met Gln Arg Ala Tyr
            420                 425                 430

Gly Pro Tyr Ser Val Thr Asn Cys Gly Glu His Asp Thr Thr Glu Tyr
        435                 440                 445

Lys Leu Arg Thr Leu Gln Val Ser Pro Leu Asp Asn Gly Asp Leu Ile
    450                 455                 460

Arg Glu Ile Trp His Tyr Gln Tyr Leu Ser Trp Pro Asp His Gly Val
465                 470                 475                 480

Pro Ser Glu Pro Gly Gly Val Leu Ser Phe Leu Asp Gln Ile Asn Gln
                485                 490                 495

Arg Gln Glu Ser Leu Pro His Ala Gly Pro Ile Ile Val His Cys Ser
            500                 505                 510

Ala Gly Ile Gly Arg Thr Gly Thr Ile Ile Val Ile Asp Met Leu Met
        515                 520                 525

Glu Asn Ile Ser Thr Lys Gly Leu Asp Cys Asp Ile Asp Ile Gln Lys
    530                 535                 540

Thr Ile Gln Met Val Arg Ala Gln Arg Ser Gly Met Val Gln Thr Glu
545                 550                 555                 560

Ala Gln Tyr Lys Phe Ile Tyr Val Ala Ile Ala Gln Phe Ile Glu Thr
                565                 570                 575

Thr Lys Lys Lys Leu
            580

<210> SEQ ID NO 31
<211> LENGTH: 42
<212> TYPE: PRT
<213> ORGANISM: Artificial Sequence
<220> FEATURE:
<223> OTHER INFORMATION: CD28 endodomain

<400> SEQUENCE: 31

Met Arg Ser Lys Arg Ser Arg Leu Leu His Ser Asp Tyr Met Asn Met
1               5                   10                  15

Thr Pro Arg Arg Pro Gly Pro Thr Arg Lys His Tyr Gln Pro Tyr Ala
                20                  25                  30

Pro Pro Arg Asp Phe Ala Ala Tyr Arg Ser
            35                  40
```

```
<210> SEQ ID NO 32
<211> LENGTH: 43
<212> TYPE: PRT
<213> ORGANISM: Artificial Sequence
<220> FEATURE:
<223> OTHER INFORMATION: 41BB endodomain

<400> SEQUENCE: 32

Met Lys Arg Gly Arg Lys Lys Leu Leu Tyr Ile Phe Lys Gln Pro Phe
1               5                   10                  15

Met Arg Pro Val Gln Thr Thr Gln Glu Glu Asp Gly Cys Ser Cys Arg
            20                  25                  30

Phe Pro Glu Glu Glu Glu Gly Gly Cys Glu Leu
        35                  40

<210> SEQ ID NO 33
<211> LENGTH: 37
<212> TYPE: PRT
<213> ORGANISM: Artificial Sequence
<220> FEATURE:
<223> OTHER INFORMATION: OX40 endodomain

<400> SEQUENCE: 33

Met Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
        35

<210> SEQ ID NO 34
<211> LENGTH: 38
<212> TYPE: PRT
<213> ORGANISM: Artificial Sequence
<220> FEATURE:
<223> OTHER INFORMATION: ICOS endodomain

<400> SEQUENCE: 34

Cys Trp Leu Thr Lys Lys Lys Tyr Ser Ser Ser Val His Asp Pro Asn
1               5                   10                  15

Gly Glu Tyr Met Phe Met Arg Ala Val Asn Thr Ala Lys Lys Ser Arg
            20                  25                  30

Leu Thr Asp Val Thr Leu
        35

<210> SEQ ID NO 35
<211> LENGTH: 48
<212> TYPE: PRT
<213> ORGANISM: Artificial Sequence
<220> FEATURE:
<223> OTHER INFORMATION: CD27 endodomain

<400> SEQUENCE: 35

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 36
<211> LENGTH: 111
<212> TYPE: PRT
```

<213> ORGANISM: Artificial Sequence
<220> FEATURE:
<223> OTHER INFORMATION: BTLA endodomain

<400> SEQUENCE: 36

```
Arg Arg His Gln Gly Lys Gln Asn Glu Leu Ser Asp Thr Ala Gly Arg
1               5                   10                  15
Glu Ile Asn Leu Val Asp Ala His Leu Lys Ser Glu Gln Thr Glu Ala
            20                  25                  30
Ser Thr Arg Gln Asn Ser Gln Val Leu Leu Ser Glu Thr Gly Ile Tyr
        35                  40                  45
Asp Asn Asp Pro Asp Leu Cys Phe Arg Met Gln Glu Gly Ser Glu Val
50                  55                  60
Tyr Ser Asn Pro Cys Leu Glu Glu Asn Lys Pro Gly Ile Val Tyr Ala
65                  70                  75                  80
Ser Leu Asn His Ser Val Ile Gly Pro Asn Ser Arg Leu Ala Arg Asn
                85                  90                  95
Val Lys Glu Ala Pro Thr Glu Tyr Ala Ser Ile Cys Val Arg Ser
            100                 105                 110
```

<210> SEQ ID NO 37
<211> LENGTH: 188
<212> TYPE: PRT
<213> ORGANISM: Artificial Sequence
<220> FEATURE:
<223> OTHER INFORMATION: CD30 endodomain

<400> SEQUENCE: 37

```
His Arg Arg Ala Cys Arg Lys Arg Ile Arg Gln Lys Leu His Leu Cys
1               5                   10                  15
Tyr Pro Val Gln Thr Ser Gln Pro Lys Leu Glu Leu Val Asp Ser Arg
            20                  25                  30
Pro Arg Arg Ser Ser Thr Gln Leu Arg Ser Gly Ala Ser Val Thr Glu
        35                  40                  45
Pro Val Ala Glu Glu Arg Gly Leu Met Ser Gln Pro Leu Met Glu Thr
50                  55                  60
Cys His Ser Val Gly Ala Ala Tyr Leu Glu Ser Leu Pro Leu Gln Asp
65                  70                  75                  80
Ala Ser Pro Ala Gly Gly Pro Ser Ser Pro Arg Asp Leu Pro Glu Pro
                85                  90                  95
Arg Val Ser Thr Glu His Thr Asn Asn Lys Ile Glu Lys Ile Tyr Ile
            100                 105                 110
Met Lys Ala Asp Thr Val Ile Val Gly Thr Val Lys Ala Glu Leu Pro
        115                 120                 125
Glu Gly Arg Gly Leu Ala Gly Pro Ala Glu Pro Glu Leu Glu Glu Glu
    130                 135                 140
Leu Glu Ala Asp His Thr Pro His Tyr Pro Glu Gln Glu Thr Glu Pro
145                 150                 155                 160
Pro Leu Gly Ser Cys Ser Asp Val Met Leu Ser Val Glu Glu Glu Gly
                165                 170                 175
Lys Glu Asp Pro Leu Pro Thr Ala Ala Ser Gly Lys
            180                 185
```

<210> SEQ ID NO 38
<211> LENGTH: 58
<212> TYPE: PRT
<213> ORGANISM: Artificial Sequence
<220> FEATURE:

<223> OTHER INFORMATION: GITR endodomain

<400> SEQUENCE: 38

```
Gln Leu Gly Leu His Ile Trp Gln Leu Arg Ser Gln Cys Met Trp Pro
1               5                   10                  15

Arg Glu Thr Gln Leu Leu Leu Glu Val Pro Pro Ser Thr Glu Asp Ala
            20                  25                  30

Arg Ser Cys Gln Phe Pro Glu Glu Glu Arg Gly Glu Arg Ser Ala Glu
        35                  40                  45

Glu Lys Gly Arg Leu Gly Asp Leu Trp Val
    50                  55
```

<210> SEQ ID NO 39
<211> LENGTH: 60
<212> TYPE: PRT
<213> ORGANISM: Artificial Sequence
<220> FEATURE:
<223> OTHER INFORMATION: HVEM endodomain

<400> SEQUENCE: 39

```
Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
            20                  25                  30

Glu Ala Leu Gln Ala Pro Pro Asp Val Thr Thr Val Ala Val Glu Glu
        35                  40                  45

Thr Ile Pro Ser Phe Thr Gly Arg Ser Pro Asn His
    50                  55                  60
```

<210> SEQ ID NO 40
<211> LENGTH: 682
<212> TYPE: PRT
<213> ORGANISM: Artificial Sequence
<220> FEATURE:
<223> OTHER INFORMATION: CD28 endodomain fused to amino-terminus of
      full-length ZAP

<400> SEQUENCE: 40

```
Met Arg Ser Lys Arg Ser Arg Leu Leu His Ser Asp Tyr Met Asn Met
1               5                   10                  15

Thr Pro Arg Arg Pro Gly Pro Thr Arg Lys His Tyr Gln Pro Tyr Ala
            20                  25                  30

Pro Pro Arg Asp Phe Ala Ala Tyr Arg Ser Ser Gly Gly Gly Gly Ser
        35                  40                  45

Gly Gly Gly Gly Ser Gly Gly Gly Ser Gly Gly Gly Gly Ser Met
    50                  55                  60

Pro Asp Pro Ala Ala His Leu Pro Phe Phe Tyr Gly Ser Ile Ser Arg
65                  70                  75                  80

Ala Glu Ala Glu Glu His Leu Lys Leu Ala Gly Met Ala Asp Gly Leu
                85                  90                  95

Phe Leu Leu Arg Gln Cys Leu Arg Ser Leu Gly Gly Tyr Val Leu Ser
            100                 105                 110

Leu Val His Asp Val Arg Phe His His Phe Pro Ile Glu Arg Gln Leu
        115                 120                 125

Asn Gly Thr Tyr Ala Ile Ala Gly Gly Lys Ala His Cys Gly Pro Ala
    130                 135                 140

Glu Leu Cys Glu Phe Tyr Ser Arg Asp Pro Asp Gly Leu Pro Cys Asn
145                 150                 155                 160
```

-continued

```
Leu Arg Lys Pro Cys Asn Arg Pro Ser Gly Leu Glu Pro Gln Pro Gly
            165                 170                 175

Val Phe Asp Cys Leu Arg Asp Ala Met Val Arg Asp Tyr Val Arg Gln
            180                 185                 190

Thr Trp Lys Leu Glu Gly Glu Ala Leu Glu Gln Ala Ile Ile Ser Gln
            195                 200                 205

Ala Pro Gln Val Glu Lys Leu Ile Ala Thr Thr Ala His Glu Arg Met
210                 215                 220

Pro Trp Tyr His Ser Ser Leu Thr Arg Glu Glu Ala Glu Arg Lys Leu
225                 230                 235                 240

Tyr Ser Gly Ala Gln Thr Asp Gly Lys Phe Leu Leu Arg Pro Arg Lys
            245                 250                 255

Glu Gln Gly Thr Tyr Ala Leu Ser Leu Ile Tyr Gly Lys Thr Val Tyr
            260                 265                 270

His Tyr Leu Ile Ser Gln Asp Lys Ala Gly Lys Tyr Cys Ile Pro Glu
            275                 280                 285

Gly Thr Lys Phe Asp Thr Leu Trp Gln Leu Val Glu Tyr Leu Lys Leu
            290                 295                 300

Lys Ala Asp Gly Leu Ile Tyr Cys Leu Lys Glu Ala Cys Pro Asn Ser
305                 310                 315                 320

Ser Ala Ser Asn Ala Ser Gly Ala Ala Ala Pro Thr Leu Pro Ala His
            325                 330                 335

Pro Ser Thr Leu Thr His Pro Gln Arg Arg Ile Asp Thr Leu Asn Ser
            340                 345                 350

Asp Gly Tyr Thr Pro Glu Pro Ala Arg Ile Thr Ser Pro Asp Lys Pro
            355                 360                 365

Arg Pro Met Pro Met Asp Thr Ser Val Tyr Glu Ser Pro Tyr Ser Asp
            370                 375                 380

Pro Glu Glu Leu Lys Asp Lys Lys Leu Phe Leu Lys Arg Asp Asn Leu
385                 390                 395                 400

Leu Ile Ala Asp Ile Glu Leu Gly Cys Gly Asn Phe Gly Ser Val Arg
            405                 410                 415

Gln Gly Val Tyr Arg Met Arg Lys Lys Gln Ile Asp Val Ala Ile Lys
            420                 425                 430

Val Leu Lys Gln Gly Thr Glu Lys Ala Asp Thr Glu Glu Met Met Arg
            435                 440                 445

Glu Ala Gln Ile Met His Gln Leu Asp Asn Pro Tyr Ile Val Arg Leu
            450                 455                 460

Ile Gly Val Cys Gln Ala Glu Ala Leu Met Leu Val Met Glu Met Ala
465                 470                 475                 480

Gly Gly Gly Pro Leu His Lys Phe Leu Val Gly Lys Arg Glu Glu Ile
            485                 490                 495

Pro Val Ser Asn Val Ala Glu Leu Leu His Gln Val Ser Met Gly Met
            500                 505                 510

Lys Tyr Leu Glu Glu Lys Asn Phe Val His Arg Asp Leu Ala Ala Arg
            515                 520                 525

Asn Val Leu Leu Val Asn Arg His Tyr Ala Lys Ile Ser Asp Phe Gly
            530                 535                 540

Leu Ser Lys Ala Leu Gly Ala Asp Asp Ser Tyr Tyr Thr Ala Arg Ser
545                 550                 555                 560

Ala Gly Lys Trp Pro Leu Lys Trp Tyr Ala Pro Glu Cys Ile Asn Phe
            565                 570                 575

Arg Lys Phe Ser Ser Arg Ser Asp Val Trp Ser Tyr Gly Val Thr Met
```

-continued

```
                580                 585                 590
Trp Glu Ala Leu Ser Tyr Gly Gln Lys Pro Tyr Lys Met Lys Gly
                595                 600                 605

Pro Glu Val Met Ala Phe Ile Glu Gln Gly Lys Arg Met Glu Cys Pro
            610                 615                 620

Pro Glu Cys Pro Pro Glu Leu Tyr Ala Leu Met Ser Asp Cys Trp Ile
625                 630                 635                 640

Tyr Lys Trp Glu Asp Arg Pro Asp Phe Leu Thr Val Glu Gln Arg Met
                645                 650                 655

Arg Ala Cys Tyr Tyr Ser Leu Ala Ser Lys Val Glu Gly Pro Pro Gly
                660                 665                 670

Ser Thr Gln Lys Ala Glu Ala Ala Cys Ala
                675                 680

<210> SEQ ID NO 41
<211> LENGTH: 683
<212> TYPE: PRT
<213> ORGANISM: Artificial Sequence
<220> FEATURE:
<223> OTHER INFORMATION: 41BB endodomain fused to amino-terminus of
      full-length ZAP

<400> SEQUENCE: 41

Met Lys Arg Gly Arg Lys Lys Leu Leu Tyr Ile Phe Lys Gln Pro Phe
1               5                   10                  15

Met Arg Pro Val Gln Thr Thr Gln Glu Glu Asp Gly Cys Ser Cys Arg
            20                  25                  30

Phe Pro Glu Glu Glu Glu Gly Gly Cys Glu Leu Ser Gly Gly Gly Gly
                35                  40                  45

Ser Gly Gly Gly Gly Ser Gly Gly Gly Gly Ser Gly Gly Gly Gly Ser
50                  55                  60

Met Pro Asp Pro Ala Ala His Leu Pro Phe Phe Tyr Gly Ser Ile Ser
65                  70                  75                  80

Arg Ala Glu Ala Glu Glu His Leu Lys Leu Ala Gly Met Ala Asp Gly
                85                  90                  95

Leu Phe Leu Leu Arg Gln Cys Leu Arg Ser Leu Gly Gly Tyr Val Leu
            100                 105                 110

Ser Leu Val His Asp Val Arg Phe His His Phe Pro Ile Glu Arg Gln
            115                 120                 125

Leu Asn Gly Thr Tyr Ala Ile Ala Gly Gly Lys Ala His Cys Gly Pro
130                 135                 140

Ala Glu Leu Cys Glu Phe Tyr Ser Arg Asp Pro Asp Gly Leu Pro Cys
145                 150                 155                 160

Asn Leu Arg Lys Pro Cys Asn Arg Pro Ser Gly Leu Glu Pro Gln Pro
                165                 170                 175

Gly Val Phe Asp Cys Leu Arg Asp Ala Met Val Arg Asp Tyr Val Arg
            180                 185                 190

Gln Thr Trp Lys Leu Glu Gly Glu Ala Leu Glu Gln Ala Ile Ile Ser
            195                 200                 205

Gln Ala Pro Gln Val Glu Lys Leu Ile Ala Thr Thr Ala His Glu Arg
        210                 215                 220

Met Pro Trp Tyr His Ser Ser Leu Thr Arg Glu Glu Ala Glu Arg Lys
225                 230                 235                 240

Leu Tyr Ser Gly Ala Gln Thr Asp Gly Lys Phe Leu Leu Arg Pro Arg
                245                 250                 255
```

```
Lys Glu Gln Gly Thr Tyr Ala Leu Ser Leu Ile Tyr Gly Lys Thr Val
                260                 265                 270

Tyr His Tyr Leu Ile Ser Gln Asp Lys Ala Gly Lys Tyr Cys Ile Pro
            275                 280                 285

Glu Gly Thr Lys Phe Asp Thr Leu Trp Gln Leu Val Glu Tyr Leu Lys
        290                 295                 300

Leu Lys Ala Asp Gly Leu Ile Tyr Cys Leu Lys Glu Ala Cys Pro Asn
305                 310                 315                 320

Ser Ser Ala Ser Asn Ala Ser Gly Ala Ala Pro Thr Leu Pro Ala
                325                 330                 335

His Pro Ser Thr Leu Thr His Pro Gln Arg Arg Ile Asp Thr Leu Asn
            340                 345                 350

Ser Asp Gly Tyr Thr Pro Glu Pro Ala Arg Ile Thr Ser Pro Asp Lys
        355                 360                 365

Pro Arg Pro Met Pro Met Asp Thr Ser Val Tyr Glu Ser Pro Tyr Ser
    370                 375                 380

Asp Pro Glu Glu Leu Lys Asp Lys Lys Leu Phe Leu Lys Arg Asp Asn
385                 390                 395                 400

Leu Leu Ile Ala Asp Ile Glu Leu Gly Cys Gly Asn Phe Gly Ser Val
                405                 410                 415

Arg Gln Gly Val Tyr Arg Met Arg Lys Lys Gln Ile Asp Val Ala Ile
            420                 425                 430

Lys Val Leu Lys Gln Gly Thr Glu Lys Ala Asp Thr Glu Glu Met Met
        435                 440                 445

Arg Glu Ala Gln Ile Met His Gln Leu Asp Asn Pro Tyr Ile Val Arg
    450                 455                 460

Leu Ile Gly Val Cys Gln Ala Glu Ala Leu Met Leu Val Met Glu Met
465                 470                 475                 480

Ala Gly Gly Gly Pro Leu His Lys Phe Leu Val Gly Lys Arg Glu Glu
                485                 490                 495

Ile Pro Val Ser Asn Val Ala Glu Leu Leu His Gln Val Ser Met Gly
            500                 505                 510

Met Lys Tyr Leu Glu Glu Lys Asn Phe Val His Arg Asp Leu Ala Ala
        515                 520                 525

Arg Asn Val Leu Leu Val Asn Arg His Tyr Ala Lys Ile Ser Asp Phe
    530                 535                 540

Gly Leu Ser Lys Ala Leu Gly Ala Asp Asp Ser Tyr Tyr Thr Ala Arg
545                 550                 555                 560

Ser Ala Gly Lys Trp Pro Leu Lys Trp Tyr Ala Pro Glu Cys Ile Asn
                565                 570                 575

Phe Arg Lys Phe Ser Ser Arg Ser Asp Val Trp Ser Tyr Gly Val Thr
            580                 585                 590

Met Trp Glu Ala Leu Ser Tyr Gly Gln Lys Pro Tyr Lys Lys Met Lys
        595                 600                 605

Gly Pro Glu Val Met Ala Phe Ile Glu Gln Gly Lys Arg Met Glu Cys
    610                 615                 620

Pro Pro Glu Cys Pro Pro Glu Leu Tyr Ala Leu Met Ser Asp Cys Trp
625                 630                 635                 640

Ile Tyr Lys Trp Glu Asp Arg Pro Asp Phe Leu Thr Val Glu Gln Arg
                645                 650                 655

Met Arg Ala Cys Tyr Tyr Ser Leu Ala Ser Lys Val Glu Gly Pro Pro
            660                 665                 670

Gly Ser Thr Gln Lys Ala Glu Ala Ala Cys Ala
```

<210> SEQ ID NO 42
<211> LENGTH: 677
<212> TYPE: PRT
<213> ORGANISM: Artificial Sequence
<220> FEATURE:
<223> OTHER INFORMATION: OX40 endodomain fused to amino-terminus of full-length ZAP

<400> SEQUENCE: 42

Met Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile Ser Gly Gly Gly Ser Gly Gly Gly Gly Ser
        35                  40                  45

Gly Gly Gly Gly Ser Gly Gly Gly Ser Met Pro Asp Pro Ala Ala
    50                  55                  60

His Leu Pro Phe Phe Tyr Gly Ser Ile Ser Arg Ala Glu Ala Glu Glu
65                  70                  75                  80

His Leu Lys Leu Ala Gly Met Ala Asp Gly Leu Phe Leu Leu Arg Gln
                85                  90                  95

Cys Leu Arg Ser Leu Gly Gly Tyr Val Leu Ser Leu Val His Asp Val
            100                 105                 110

Arg Phe His His Phe Pro Ile Glu Arg Gln Leu Asn Gly Thr Tyr Ala
        115                 120                 125

Ile Ala Gly Gly Lys Ala His Cys Gly Pro Ala Glu Leu Cys Glu Phe
130                 135                 140

Tyr Ser Arg Asp Pro Asp Gly Leu Pro Cys Asn Leu Arg Lys Pro Cys
145                 150                 155                 160

Asn Arg Pro Ser Gly Leu Glu Pro Gln Pro Gly Val Phe Asp Cys Leu
                165                 170                 175

Arg Asp Ala Met Val Arg Asp Tyr Val Arg Gln Thr Trp Lys Leu Glu
            180                 185                 190

Gly Glu Ala Leu Glu Gln Ala Ile Ile Ser Gln Ala Pro Gln Val Glu
        195                 200                 205

Lys Leu Ile Ala Thr Thr Ala His Glu Arg Met Pro Trp Tyr His Ser
210                 215                 220

Ser Leu Thr Arg Glu Glu Ala Glu Arg Lys Leu Tyr Ser Gly Ala Gln
225                 230                 235                 240

Thr Asp Gly Lys Phe Leu Leu Arg Pro Arg Lys Glu Gln Gly Thr Tyr
                245                 250                 255

Ala Leu Ser Leu Ile Tyr Gly Lys Thr Val Tyr His Tyr Leu Ile Ser
            260                 265                 270

Gln Asp Lys Ala Gly Lys Tyr Cys Ile Pro Glu Gly Thr Lys Phe Asp
        275                 280                 285

Thr Leu Trp Gln Leu Val Glu Tyr Leu Lys Leu Lys Ala Asp Gly Leu
290                 295                 300

Ile Tyr Cys Leu Lys Glu Ala Cys Pro Asn Ser Ser Ala Ser Asn Ala
305                 310                 315                 320

Ser Gly Ala Ala Ala Pro Thr Leu Pro Ala His Pro Ser Thr Leu Thr
                325                 330                 335

His Pro Gln Arg Arg Ile Asp Thr Leu Asn Ser Asp Gly Tyr Thr Pro
            340                 345                 350

-continued

```
Glu Pro Ala Arg Ile Thr Ser Pro Asp Lys Pro Arg Pro Met Pro Met
            355                 360                 365

Asp Thr Ser Val Tyr Glu Ser Pro Tyr Ser Pro Glu Glu Leu Lys
370                 375                 380

Asp Lys Lys Leu Phe Leu Lys Arg Asp Asn Leu Leu Ile Ala Asp Ile
385                 390                 395                 400

Glu Leu Gly Cys Gly Asn Phe Gly Ser Val Arg Gln Gly Val Tyr Arg
                405                 410                 415

Met Arg Lys Lys Gln Ile Asp Val Ala Ile Lys Val Leu Lys Gln Gly
            420                 425                 430

Thr Glu Lys Ala Asp Thr Glu Glu Met Met Arg Glu Ala Gln Ile Met
        435                 440                 445

His Gln Leu Asp Asn Pro Tyr Ile Val Arg Leu Ile Gly Val Cys Gln
    450                 455                 460

Ala Glu Ala Leu Met Leu Val Met Glu Met Ala Gly Gly Pro Leu
465                 470                 475                 480

His Lys Phe Leu Val Gly Lys Arg Glu Glu Ile Pro Val Ser Asn Val
                485                 490                 495

Ala Glu Leu Leu His Gln Val Ser Met Gly Met Lys Tyr Leu Glu Glu
            500                 505                 510

Lys Asn Phe Val His Arg Asp Leu Ala Ala Arg Asn Val Leu Leu Val
        515                 520                 525

Asn Arg His Tyr Ala Lys Ile Ser Asp Phe Gly Leu Ser Lys Ala Leu
    530                 535                 540

Gly Ala Asp Asp Ser Tyr Tyr Thr Ala Arg Ser Ala Gly Lys Trp Pro
545                 550                 555                 560

Leu Lys Trp Tyr Ala Pro Glu Cys Ile Asn Phe Arg Lys Phe Ser Ser
                565                 570                 575

Arg Ser Asp Val Trp Ser Tyr Gly Val Thr Met Trp Glu Ala Leu Ser
            580                 585                 590

Tyr Gly Gln Lys Pro Tyr Lys Lys Met Lys Gly Pro Glu Val Met Ala
        595                 600                 605

Phe Ile Glu Gln Gly Lys Arg Met Glu Cys Pro Pro Glu Cys Pro Pro
    610                 615                 620

Glu Leu Tyr Ala Leu Met Ser Asp Cys Trp Ile Tyr Lys Trp Glu Asp
625                 630                 635                 640

Arg Pro Asp Phe Leu Thr Val Glu Gln Arg Met Arg Ala Cys Tyr Tyr
                645                 650                 655

Ser Leu Ala Ser Lys Val Glu Gly Pro Pro Gly Ser Thr Gln Lys Ala
            660                 665                 670

Glu Ala Ala Cys Ala
        675

<210> SEQ ID NO 43
<211> LENGTH: 276
<212> TYPE: PRT
<213> ORGANISM: Artificial Sequence
<220> FEATURE:
<223> OTHER INFORMATION: CD28 endodomain fused to the amino-terminus of
      PTPN6 SH2 domain

<400> SEQUENCE: 43

Met Arg Ser Lys Arg Ser Arg Leu Leu His Ser Asp Tyr Met Asn Met
1               5                   10                  15

Thr Pro Arg Arg Pro Gly Pro Thr Arg Lys His Tyr Gln Pro Tyr Ala
            20                  25                  30
```

```
Pro Pro Arg Asp Phe Ala Ala Tyr Arg Ser Ser Gly Gly Gly Ser
        35                  40                  45

Gly Gly Gly Ser Gly Gly Gly Ser Gly Gly Gly Ser Met
    50                  55                  60

Val Arg Trp Phe His Arg Asp Leu Ser Gly Leu Asp Ala Glu Thr Leu
65                  70                  75                  80

Leu Lys Gly Arg Gly Val His Gly Ser Phe Leu Ala Arg Pro Ser Arg
                85                  90                  95

Lys Asn Gln Gly Asp Phe Ser Leu Ser Val Arg Val Gly Asp Gln Val
                100                 105                 110

Thr His Ile Arg Ile Gln Asn Ser Gly Asp Phe Tyr Asp Leu Tyr Gly
                115                 120                 125

Gly Glu Lys Phe Ala Thr Leu Thr Glu Leu Val Glu Tyr Tyr Thr Gln
        130                 135                 140

Gln Gln Gly Val Leu Gln Asp Arg Asp Gly Thr Ile Ile His Leu Lys
145                 150                 155                 160

Tyr Pro Leu Asn Cys Ser Asp Pro Thr Ser Glu Arg Trp Tyr His Gly
                165                 170                 175

His Met Ser Gly Gly Gln Ala Glu Thr Leu Leu Gln Ala Lys Gly Glu
                180                 185                 190

Pro Trp Thr Phe Leu Val Arg Glu Ser Leu Ser Gln Pro Gly Asp Phe
                195                 200                 205

Val Leu Ser Val Leu Ser Asp Gln Pro Lys Ala Gly Pro Gly Ser Pro
        210                 215                 220

Leu Arg Val Thr His Ile Lys Val Met Cys Glu Gly Gly Arg Tyr Thr
225                 230                 235                 240

Val Gly Gly Leu Glu Thr Phe Asp Ser Leu Thr Asp Leu Val Glu His
                245                 250                 255

Phe Lys Lys Thr Gly Ile Glu Glu Ala Ser Gly Ala Phe Val Tyr Leu
                260                 265                 270

Arg Gln Pro Tyr
        275

<210> SEQ ID NO 44
<211> LENGTH: 277
<212> TYPE: PRT
<213> ORGANISM: Artificial Sequence
<220> FEATURE:
<223> OTHER INFORMATION: 41BB endodomain fused to the amino-terminus of
      PTPN6 SH2 domain

<400> SEQUENCE: 44

Met Lys Arg Gly Arg Lys Lys Leu Leu Tyr Ile Phe Lys Gln Pro Phe
1               5                   10                  15

Met Arg Pro Val Gln Thr Thr Gln Glu Glu Asp Gly Cys Ser Cys Arg
                20                  25                  30

Phe Pro Glu Glu Glu Glu Gly Gly Cys Glu Leu Ser Gly Gly Gly Gly
        35                  40                  45

Ser Gly Gly Gly Gly Ser Gly Gly Gly Gly Ser Gly Gly Gly Gly Ser
    50                  55                  60

Met Val Arg Trp Phe His Arg Asp Leu Ser Gly Leu Asp Ala Glu Thr
65                  70                  75                  80

Leu Leu Lys Gly Arg Gly Val His Gly Ser Phe Leu Ala Arg Pro Ser
                85                  90                  95

Arg Lys Asn Gln Gly Asp Phe Ser Leu Ser Val Arg Val Gly Asp Gln
```

```
                  100                 105                 110
Val Thr His Ile Arg Ile Gln Asn Ser Gly Asp Phe Tyr Asp Leu Tyr
            115                 120                 125

Gly Gly Glu Lys Phe Ala Thr Leu Thr Glu Leu Val Glu Tyr Tyr Thr
130                 135                 140

Gln Gln Gln Gly Val Leu Gln Asp Arg Asp Gly Thr Ile Ile His Leu
145                 150                 155                 160

Lys Tyr Pro Leu Asn Cys Ser Asp Pro Thr Ser Glu Arg Trp Tyr His
            165                 170                 175

Gly His Met Ser Gly Gln Ala Glu Thr Leu Leu Gln Ala Lys Gly
            180                 185                 190

Glu Pro Trp Thr Phe Leu Val Arg Glu Ser Leu Ser Gln Pro Gly Asp
            195                 200                 205

Phe Val Leu Ser Val Leu Ser Asp Gln Pro Lys Ala Gly Pro Gly Ser
210                 215                 220

Pro Leu Arg Val Thr His Ile Lys Val Met Cys Glu Gly Gly Arg Tyr
225                 230                 235                 240

Thr Val Gly Gly Leu Glu Thr Phe Asp Ser Leu Thr Asp Leu Val Glu
            245                 250                 255

His Phe Lys Lys Thr Gly Ile Glu Glu Ala Ser Gly Ala Phe Val Tyr
            260                 265                 270

Leu Arg Gln Pro Tyr
            275

<210> SEQ ID NO 45
<211> LENGTH: 271
<212> TYPE: PRT
<213> ORGANISM: Artificial Sequence
<220> FEATURE:
<223> OTHER INFORMATION: OX40 endodomain fused to the amino-terminus of
      PTPN6 SH2 domain

<400> SEQUENCE: 45

Met Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile Ser Gly Gly Gly Ser Gly Gly Gly Gly Ser
            35                  40                  45

Gly Gly Gly Gly Ser Gly Gly Gly Ser Met Val Arg Trp Phe His
50                  55                  60

Arg Asp Leu Ser Gly Leu Asp Ala Glu Thr Leu Leu Lys Gly Arg Gly
65                  70                  75                  80

Val His Gly Ser Phe Leu Ala Arg Pro Ser Arg Lys Asn Gln Gly Asp
            85                  90                  95

Phe Ser Leu Ser Val Arg Val Gly Asp Gln Val Thr His Ile Arg Ile
            100                 105                 110

Gln Asn Ser Gly Asp Phe Tyr Asp Leu Tyr Gly Gly Glu Lys Phe Ala
            115                 120                 125

Thr Leu Thr Glu Leu Val Glu Tyr Tyr Thr Gln Gln Gln Gly Val Leu
            130                 135                 140

Gln Asp Arg Asp Gly Thr Ile Ile His Leu Lys Tyr Pro Leu Asn Cys
145                 150                 155                 160

Ser Asp Pro Thr Ser Glu Arg Trp Tyr His Gly His Met Ser Gly Gly
            165                 170                 175
```

Gln Ala Glu Thr Leu Leu Gln Ala Lys Gly Glu Pro Trp Thr Phe Leu
            180                 185                 190

Val Arg Glu Ser Leu Ser Gln Pro Gly Asp Phe Val Leu Ser Val Leu
        195                 200                 205

Ser Asp Gln Pro Lys Ala Gly Pro Gly Ser Pro Leu Arg Val Thr His
    210                 215                 220

Ile Lys Val Met Cys Glu Gly Gly Arg Tyr Thr Val Gly Gly Leu Glu
225                 230                 235                 240

Thr Phe Asp Ser Leu Thr Asp Leu Val Glu His Phe Lys Lys Thr Gly
            245                 250                 255

Ile Glu Glu Ala Ser Gly Ala Phe Val Tyr Leu Arg Gln Pro Tyr
            260                 265                 270

<210> SEQ ID NO 46
<211> LENGTH: 350
<212> TYPE: PRT
<213> ORGANISM: Artificial Sequence
<220> FEATURE:
<223> OTHER INFORMATION: Akt kinase domain

<400> SEQUENCE: 46

Ala Glu Glu Met Glu Val Ser Leu Ala Lys Pro Lys His Arg Val Thr
1               5                   10                  15

Met Asn Glu Phe Glu Tyr Leu Lys Leu Leu Gly Lys Gly Thr Phe Gly
            20                  25                  30

Lys Val Ile Leu Val Lys Glu Lys Ala Thr Gly Arg Tyr Tyr Ala Met
        35                  40                  45

Lys Ile Leu Lys Lys Glu Val Ile Val Ala Lys Asp Glu Val Ala His
    50                  55                  60

Thr Leu Thr Glu Asn Arg Val Leu Gln Asn Ser Arg His Pro Phe Leu
65                  70                  75                  80

Thr Ala Leu Lys Tyr Ser Phe Gln Thr His Asp Arg Leu Cys Phe Val
            85                  90                  95

Met Glu Tyr Ala Asn Gly Gly Glu Leu Phe Phe His Leu Ser Arg Glu
            100                 105                 110

Arg Val Phe Ser Glu Asp Arg Ala Arg Phe Tyr Gly Ala Glu Ile Val
        115                 120                 125

Ser Ala Leu Asp Tyr Leu His Ser Glu Lys Asn Val Val Tyr Arg Asp
    130                 135                 140

Leu Lys Leu Glu Asn Leu Met Leu Asp Lys Asp Gly His Ile Lys Ile
145                 150                 155                 160

Thr Asp Phe Gly Leu Cys Lys Glu Gly Ile Lys Asp Gly Ala Thr Met
            165                 170                 175

Lys Thr Phe Cys Gly Thr Pro Glu Tyr Leu Ala Pro Glu Val Leu Glu
        180                 185                 190

Asp Asn Asp Tyr Gly Arg Ala Val Asp Trp Trp Gly Leu Gly Val Val
    195                 200                 205

Met Tyr Glu Met Met Cys Gly Arg Leu Pro Phe Tyr Asn Gln Asp His
    210                 215                 220

Glu Lys Leu Phe Glu Leu Ile Leu Met Glu Glu Ile Arg Phe Pro Arg
225                 230                 235                 240

Thr Leu Gly Pro Glu Ala Lys Ser Leu Leu Ser Gly Leu Leu Lys Lys
            245                 250                 255

Asp Pro Lys Gln Arg Leu Gly Gly Gly Ser Glu Asp Ala Lys Glu Ile
            260                 265                 270

```
Met Gln His Arg Phe Phe Ala Gly Ile Val Trp Gln His Val Tyr Glu
            275                 280                 285

Lys Lys Leu Ser Pro Pro Phe Lys Pro Gln Val Thr Ser Glu Thr Asp
    290                 295                 300

Thr Arg Tyr Phe Asp Glu Glu Phe Thr Ala Gln Met Ile Thr Ile Thr
305                 310                 315                 320

Pro Pro Asp Gln Asp Asp Ser Met Glu Cys Val Asp Ser Glu Arg Arg
                325                 330                 335

Pro His Phe Pro Gln Phe Ser Tyr Ser Ala Ser Gly Thr Ala
            340                 345                 350

<210> SEQ ID NO 47
<211> LENGTH: 630
<212> TYPE: PRT
<213> ORGANISM: Artificial Sequence
<220> FEATURE:
<223> OTHER INFORMATION: ZAP70-SH2 domain fused directly to an Akt
      kinase domain

<400> SEQUENCE: 47

Met Pro Asp Pro Ala Ala His Leu Pro Phe Phe Tyr Gly Ser Ile Ser
1               5                   10                  15

Arg Ala Glu Ala Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
    130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
    210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Ala Pro Thr Leu Pro Ala
            260                 265                 270

His Pro Ser Thr Leu Thr His Pro Ala Glu Glu Met Glu Val Ser Leu
        275                 280                 285
```

Ala Lys Pro Lys His Arg Val Thr Met Asn Glu Phe Glu Tyr Leu Lys
    290                 295                 300

Leu Leu Gly Lys Gly Thr Phe Gly Lys Val Ile Leu Val Lys Glu Lys
305                 310                 315                 320

Ala Thr Gly Arg Tyr Tyr Ala Met Lys Ile Leu Lys Lys Glu Val Ile
                325                 330                 335

Val Ala Lys Asp Glu Val Ala His Thr Leu Thr Glu Asn Arg Val Leu
            340                 345                 350

Gln Asn Ser Arg His Pro Phe Leu Thr Ala Leu Lys Tyr Ser Phe Gln
        355                 360                 365

Thr His Asp Arg Leu Cys Phe Val Met Glu Tyr Ala Asn Gly Gly Glu
    370                 375                 380

Leu Phe Phe His Leu Ser Arg Glu Arg Val Phe Ser Glu Asp Arg Ala
385                 390                 395                 400

Arg Phe Tyr Gly Ala Glu Ile Val Ser Ala Leu Asp Tyr Leu His Ser
                405                 410                 415

Glu Lys Asn Val Val Tyr Arg Asp Leu Lys Leu Glu Asn Leu Met Leu
            420                 425                 430

Asp Lys Asp Gly His Ile Lys Ile Thr Asp Phe Gly Leu Cys Lys Glu
        435                 440                 445

Gly Ile Lys Asp Gly Ala Thr Met Lys Thr Phe Cys Gly Thr Pro Glu
    450                 455                 460

Tyr Leu Ala Pro Glu Val Leu Glu Asp Asn Asp Tyr Gly Arg Ala Val
465                 470                 475                 480

Asp Trp Trp Gly Leu Gly Val Val Met Tyr Glu Met Met Cys Gly Arg
                485                 490                 495

Leu Pro Phe Tyr Asn Gln Asp His Glu Lys Leu Phe Glu Leu Ile Leu
            500                 505                 510

Met Glu Glu Ile Arg Phe Pro Arg Thr Leu Gly Pro Glu Ala Lys Ser
        515                 520                 525

Leu Leu Ser Gly Leu Leu Lys Lys Asp Pro Lys Gln Arg Leu Gly Gly
    530                 535                 540

Gly Ser Glu Asp Ala Lys Glu Ile Met Gln His Arg Phe Phe Ala Gly
545                 550                 555                 560

Ile Val Trp Gln His Val Tyr Glu Lys Lys Leu Ser Pro Pro Phe Lys
                565                 570                 575

Pro Gln Val Thr Ser Glu Thr Asp Thr Arg Tyr Phe Asp Glu Glu Phe
            580                 585                 590

Thr Ala Gln Met Ile Thr Ile Thr Pro Pro Asp Gln Asp Asp Ser Met
        595                 600                 605

Glu Cys Val Asp Ser Glu Arg Arg Pro His Phe Pro Gln Phe Ser Tyr
    610                 615                 620

Ser Ala Ser Gly Thr Ala
625                 630

<210> SEQ ID NO 48
<211> LENGTH: 651
<212> TYPE: PRT
<213> ORGANISM: Artificial Sequence
<220> FEATURE:
<223> OTHER INFORMATION: ZAP70-SH2 domain fused to an Akt kinase domain
      via a linker

<400> SEQUENCE: 48

Met Pro Asp Pro Ala Ala His Leu Pro Phe Phe Tyr Gly Ser Ile Ser

-continued

```
1               5                   10                  15
Arg Ala Glu Ala Glu His Leu Lys Leu Ala Gly Met Ala Asp Gly
                20                  25                  30

Leu Phe Leu Leu Arg Gln Cys Leu Arg Ser Leu Gly Gly Tyr Val Leu
            35                  40                  45

Ser Leu Val His Asp Val Arg Phe His Phe Pro Ile Glu Arg Gln
        50                  55                  60

Leu Asn Gly Thr Tyr Ala Ile Ala Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
                100                 105                 110

Gly Val Phe Asp Cys Leu Arg Asp Ala Met Val Arg Asp Tyr Val Arg
                115                 120                 125

Gln Thr Trp Lys Leu Glu Gly Glu Ala Leu Glu Gln Ala Ile Ile Ser
            130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Ala Glu Arg Lys
                165                 170                 175

Leu Tyr Ser Gly Ala Gln Thr Asp Gly Lys Phe Leu Leu Arg Pro Arg
                180                 185                 190

Lys Glu Gln Gly Thr Tyr Ala Leu Ser Leu Ile Tyr Gly Lys Thr Val
                195                 200                 205

Tyr His Tyr Leu Ile Ser Gln Asp Lys Ala Gly Lys Tyr Cys Ile Pro
210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Ala Pro Thr Leu Pro Ala
                260                 265                 270

His Pro Ser Thr Leu Thr His Pro Ser Gly Gly Gly Ser Gly Gly
            275                 280                 285

Gly Gly Ser Gly Gly Gly Ser Gly Gly Gly Ser Ala Glu Glu
            290                 295                 300

Met Glu Val Ser Leu Ala Lys Pro Lys His Arg Val Thr Met Asn Glu
305                 310                 315                 320

Phe Glu Tyr Leu Lys Leu Leu Gly Lys Gly Thr Phe Gly Lys Val Ile
                325                 330                 335

Leu Val Lys Glu Lys Ala Thr Gly Arg Tyr Tyr Ala Met Lys Ile Leu
                340                 345                 350

Lys Lys Glu Val Ile Val Ala Lys Asp Glu Val Ala His Thr Leu Thr
                355                 360                 365

Glu Asn Arg Val Leu Gln Asn Ser Arg His Pro Phe Leu Thr Ala Leu
                370                 375                 380

Lys Tyr Ser Phe Gln Thr His Asp Arg Leu Cys Phe Val Met Glu Tyr
385                 390                 395                 400

Ala Asn Gly Gly Glu Leu Phe Phe His Leu Ser Arg Glu Arg Val Phe
                405                 410                 415

Ser Glu Asp Arg Ala Arg Phe Tyr Gly Ala Glu Ile Val Ser Ala Leu
                420                 425                 430
```

```
Asp Tyr Leu His Ser Glu Lys Asn Val Val Tyr Arg Asp Leu Lys Leu
        435                 440                 445
Glu Asn Leu Met Leu Asp Lys Asp Gly His Ile Lys Ile Thr Asp Phe
    450                 455                 460
Gly Leu Cys Lys Glu Gly Ile Lys Asp Gly Ala Thr Met Lys Thr Phe
465                 470                 475                 480
Cys Gly Thr Pro Glu Tyr Leu Ala Pro Glu Val Leu Glu Asp Asn Asp
                485                 490                 495
Tyr Gly Arg Ala Val Asp Trp Trp Gly Leu Gly Val Val Met Tyr Glu
            500                 505                 510
Met Met Cys Gly Arg Leu Pro Phe Tyr Asn Gln Asp His Glu Lys Leu
        515                 520                 525
Phe Glu Leu Ile Leu Met Glu Glu Ile Arg Phe Pro Arg Thr Leu Gly
    530                 535                 540
Pro Glu Ala Lys Ser Leu Leu Ser Gly Leu Leu Lys Lys Asp Pro Lys
545                 550                 555                 560
Gln Arg Leu Gly Gly Gly Ser Glu Asp Ala Lys Glu Ile Met Gln His
                565                 570                 575
Arg Phe Phe Ala Gly Ile Val Trp Gln His Val Tyr Glu Lys Lys Leu
            580                 585                 590
Ser Pro Pro Phe Lys Pro Gln Val Thr Ser Glu Thr Asp Thr Arg Tyr
        595                 600                 605
Phe Asp Glu Glu Phe Thr Ala Gln Met Ile Thr Ile Thr Pro Pro Asp
    610                 615                 620
Gln Asp Asp Ser Met Glu Cys Val Asp Ser Glu Arg Arg Pro His Phe
625                 630                 635                 640
Pro Gln Phe Ser Tyr Ser Ala Ser Gly Thr Ala
                645                 650

<210> SEQ ID NO 49
<211> LENGTH: 630
<212> TYPE: PRT
<213> ORGANISM: Artificial Sequence
<220> FEATURE:
<223> OTHER INFORMATION: ZAP70 mutated to be non-functional and fused to
      an Akt kinase domain

<400> SEQUENCE: 49

Met Pro Asp Pro Ala Ala His Leu Pro Phe Phe Tyr Gly Ser Ile Ser
1               5                   10                  15
Arg Ala Glu Ala Glu Glu His Leu Lys Leu Ala Gly Met Ala Asp Gly
                20                  25                  30
Leu Phe Leu Leu Arg Gln Cys Leu Arg Ser Leu Gly Gly Tyr Val Leu
            35                  40                  45
Ser Leu Val His Asp Val Arg Phe His His Phe Pro Ile Glu Arg Gln
        50                  55                  60
Leu Asn Gly Thr Tyr Ala Ile Ala Gly Gly Lys Ala His Cys Gly Pro
65                  70                  75                  80
Ala Glu Leu Cys Glu Phe Tyr Ser Arg Asp Pro Asp Gly Leu Pro Cys
                85                  90                  95
Asn Leu Arg Lys Pro Cys Asn Arg Pro Ser Gly Leu Glu Pro Gln Pro
                100                 105                 110
Gly Val Phe Asp Cys Leu Arg Asp Ala Met Val Arg Asp Tyr Val Arg
            115                 120                 125
Gln Thr Trp Lys Leu Glu Gly Glu Ala Leu Glu Gln Ala Ile Ile Ser
```

```
            130                 135                 140
Gln Ala Pro Gln Val Glu Lys Leu Ile Ala Thr Thr Ala His Glu Arg
145                 150                 155                 160
Met Pro Trp Tyr His Ser Ser Leu Thr Arg Glu Ala Glu Arg Lys
                165                 170                 175
Leu Tyr Ser Gly Ala Gln Thr Asp Gly Lys Phe Leu Leu Lys Pro Arg
                180                 185                 190
Lys Glu Gln Gly Thr Tyr Ala Leu Ser Leu Ile Tyr Gly Lys Thr Val
                195                 200                 205
Tyr His Tyr Leu Ile Ser Gln Asp Lys Ala Gly Lys Tyr Cys Ile Pro
210                 215                 220
Glu Gly Thr Lys Phe Asp Thr Leu Trp Gln Leu Val Glu Tyr Leu Lys
225                 230                 235                 240
Leu Lys Ala Asp Gly Leu Ile Tyr Cys Leu Lys Glu Ala Cys Pro Asn
                245                 250                 255
Ser Ser Ala Ser Asn Ala Ser Gly Ala Ala Ala Pro Thr Leu Pro Ala
                260                 265                 270
His Pro Ser Thr Leu Thr His Pro Ala Glu Glu Met Glu Val Ser Leu
                275                 280                 285
Ala Lys Pro Lys His Arg Val Thr Met Asn Glu Phe Glu Tyr Leu Lys
290                 295                 300
Leu Leu Gly Lys Gly Thr Phe Gly Lys Val Ile Leu Val Lys Glu Lys
305                 310                 315                 320
Ala Thr Gly Arg Tyr Tyr Ala Met Lys Ile Leu Lys Lys Glu Val Ile
                325                 330                 335
Val Ala Lys Asp Glu Val Ala His Thr Leu Thr Glu Asn Arg Val Leu
                340                 345                 350
Gln Asn Ser Arg His Pro Phe Leu Thr Ala Leu Lys Tyr Ser Phe Gln
                355                 360                 365
Thr His Asp Arg Leu Cys Phe Val Met Glu Tyr Ala Asn Gly Gly Glu
                370                 375                 380
Leu Phe Phe His Leu Ser Arg Glu Arg Val Phe Ser Glu Asp Arg Ala
385                 390                 395                 400
Arg Phe Tyr Gly Ala Glu Ile Val Ser Ala Leu Asp Tyr Leu His Ser
                405                 410                 415
Glu Lys Asn Val Val Tyr Arg Asp Leu Lys Leu Glu Asn Leu Met Leu
                420                 425                 430
Asp Lys Asp Gly His Ile Lys Ile Thr Asp Phe Gly Leu Cys Lys Glu
                435                 440                 445
Gly Ile Lys Asp Gly Ala Thr Met Lys Thr Phe Cys Gly Thr Pro Glu
450                 455                 460
Tyr Leu Ala Pro Glu Val Leu Glu Asp Asn Asp Tyr Gly Arg Ala Val
465                 470                 475                 480
Asp Trp Trp Gly Leu Gly Val Val Met Tyr Glu Met Met Cys Gly Arg
                485                 490                 495
Leu Pro Phe Tyr Asn Gln Asp His Glu Lys Leu Phe Glu Leu Ile Leu
                500                 505                 510
Met Glu Glu Ile Arg Phe Pro Arg Thr Leu Gly Pro Glu Ala Lys Ser
                515                 520                 525
Leu Leu Ser Gly Leu Leu Lys Lys Asp Pro Lys Gln Arg Leu Gly Gly
                530                 535                 540
Gly Ser Glu Asp Ala Lys Glu Ile Met Gln His Arg Phe Phe Ala Gly
545                 550                 555                 560
```

```
Ile Val Trp Gln His Val Tyr Glu Lys Lys Leu Ser Pro Pro Phe Lys
                565                 570                 575

Pro Gln Val Thr Ser Glu Thr Asp Thr Arg Tyr Phe Asp Glu Phe
            580                 585                 590

Thr Ala Gln Met Ile Thr Ile Thr Pro Pro Asp Gln Asp Ser Met
        595                 600                 605

Glu Cys Val Asp Ser Glu Arg Arg Pro His Phe Pro Gln Phe Ser Tyr
    610                 615                 620

Ser Ala Ser Gly Thr Ala
625                 630

<210> SEQ ID NO 50
<211> LENGTH: 590
<212> TYPE: PRT
<213> ORGANISM: Artificial Sequence
<220> FEATURE:
<223> OTHER INFORMATION: Kinase containing domain of JAK2

<400> SEQUENCE: 50

Arg Asn Glu Asp Leu Ile Phe Asn Glu Ser Leu Gly Gln Gly Thr Phe
1               5                   10                  15

Thr Lys Ile Phe Lys Gly Val Arg Arg Glu Val Gly Asp Tyr Gly Gln
            20                  25                  30

Leu His Glu Thr Glu Val Leu Leu Lys Val Leu Asp Lys Ala His Arg
        35                  40                  45

Asn Tyr Ser Glu Ser Phe Phe Glu Ala Ala Ser Met Met Ser Lys Leu
    50                  55                  60

Ser His Lys His Leu Val Leu Asn Tyr Gly Val Cys Val Cys Gly Asp
65                  70                  75                  80

Glu Asn Ile Leu Val Gln Glu Phe Val Lys Phe Gly Ser Leu Asp Thr
                85                  90                  95

Tyr Leu Lys Lys Asn Lys Asn Cys Ile Asn Ile Leu Trp Lys Leu Glu
            100                 105                 110

Val Ala Lys Gln Leu Ala Trp Ala Met His Phe Leu Glu Glu Asn Thr
        115                 120                 125

Leu Ile His Gly Asn Val Cys Ala Lys Asn Ile Leu Leu Ile Arg Glu
    130                 135                 140

Glu Asp Arg Lys Thr Gly Asn Pro Pro Phe Ile Lys Leu Ser Asp Pro
145                 150                 155                 160

Gly Ile Ser Ile Thr Val Leu Pro Lys Asp Ile Leu Gln Glu Arg Ile
                165                 170                 175

Pro Trp Val Pro Pro Glu Cys Ile Glu Asn Pro Lys Asn Leu Asn Leu
            180                 185                 190

Ala Thr Asp Lys Trp Ser Phe Gly Thr Thr Leu Trp Glu Ile Cys Ser
        195                 200                 205

Gly Gly Asp Lys Pro Leu Ser Ala Leu Asp Ser Gln Arg Lys Leu Gln
    210                 215                 220

Phe Tyr Glu Asp Arg His Gln Leu Pro Ala Pro Lys Trp Ala Glu Leu
225                 230                 235                 240

Ala Asn Leu Ile Asn Asn Cys Met Asp Tyr Glu Pro Asp Phe Arg Pro
                245                 250                 255

Ser Phe Arg Ala Ile Ile Arg Asp Leu Asn Ser Leu Phe Thr Pro Asp
            260                 265                 270

Tyr Glu Leu Leu Thr Glu Asn Asp Met Leu Pro Asn Met Arg Ile Gly
        275                 280                 285
```

Ala Leu Gly Phe Ser Gly Ala Phe Glu Asp Arg Asp Pro Thr Gln Phe
            290                 295                 300

Glu Glu Arg His Leu Lys Phe Leu Gln Gln Leu Gly Lys Gly Asn Phe
305                 310                 315                 320

Gly Ser Val Glu Met Cys Arg Tyr Asp Pro Leu Gln Asp Asn Thr Gly
                325                 330                 335

Glu Val Val Ala Val Lys Lys Leu Gln His Ser Thr Glu Glu His Leu
            340                 345                 350

Arg Asp Phe Glu Arg Glu Ile Glu Ile Leu Lys Ser Leu Gln His Asp
        355                 360                 365

Asn Ile Val Lys Tyr Lys Gly Val Cys Tyr Ser Ala Gly Arg Arg Asn
    370                 375                 380

Leu Lys Leu Ile Met Glu Tyr Leu Pro Tyr Gly Ser Leu Arg Asp Tyr
385                 390                 395                 400

Leu Gln Lys His Lys Glu Arg Ile Asp His Ile Lys Leu Leu Gln Tyr
                405                 410                 415

Thr Ser Gln Ile Cys Lys Gly Met Glu Tyr Leu Gly Thr Lys Arg Tyr
            420                 425                 430

Ile His Arg Asp Leu Ala Thr Arg Asn Ile Leu Val Glu Asn Glu Asn
        435                 440                 445

Arg Val Lys Ile Gly Asp Phe Gly Leu Thr Lys Val Leu Pro Gln Asp
    450                 455                 460

Lys Glu Tyr Tyr Lys Val Lys Glu Pro Gly Glu Ser Pro Ile Phe Trp
465                 470                 475                 480

Tyr Ala Pro Glu Ser Leu Thr Glu Ser Lys Phe Ser Val Ala Ser Asp
                485                 490                 495

Val Trp Ser Phe Gly Val Val Leu Tyr Glu Leu Phe Thr Tyr Ile Glu
            500                 505                 510

Lys Ser Lys Ser Pro Pro Ala Glu Phe Met Arg Met Ile Gly Asn Asp
        515                 520                 525

Lys Gln Gly Gln Met Ile Val Phe His Leu Ile Glu Leu Leu Lys Asn
    530                 535                 540

Asn Gly Arg Leu Pro Arg Pro Asp Gly Cys Pro Asp Glu Ile Tyr Met
545                 550                 555                 560

Ile Met Thr Glu Cys Trp Asn Asn Val Asn Gln Arg Pro Ser Phe
                565                 570                 575

Arg Asp Leu Ala Leu Arg Val Asp Gln Ile Arg Asp Asn Met
            580                 585                 590

```
<210> SEQ ID NO 51
<211> LENGTH: 7
<212> TYPE: PRT
<213> ORGANISM: Artificial Sequence
<220> FEATURE:
<223> OTHER INFORMATION: consensus Tobacco Etch Virus (TEV) cleavage
      site

<400> SEQUENCE: 51
```

Glu Asn Leu Tyr Phe Gln Ser
1               5

```
<210> SEQ ID NO 52
<211> LENGTH: 240
<212> TYPE: PRT
<213> ORGANISM: Artificial Sequence
<220> FEATURE:
<223> OTHER INFORMATION: TeV protease domain
```

<400> SEQUENCE: 52

```
Ser Leu Phe Lys Gly Pro Arg Asp Tyr Asn Pro Ile Ser Ser Thr Ile
1               5                   10                  15

Cys His Leu Thr Asn Glu Ser Asp Gly His Thr Thr Ser Leu Tyr Gly
            20                  25                  30

Ile Gly Phe Gly Pro Phe Ile Ile Thr Asn Lys His Leu Phe Arg Arg
        35                  40                  45

Asn Asn Gly Thr Leu Leu Val Gln Ser Leu His Gly Val Phe Lys Val
    50                  55                  60

Lys Asn Thr Thr Thr Leu Gln Gln His Leu Ile Asp Gly Arg Asp Met
65                  70                  75                  80

Ile Ile Ile Arg Met Pro Lys Asp Phe Pro Phe Pro Gln Lys Leu
                85                  90                  95

Lys Phe Arg Glu Pro Gln Arg Glu Arg Ile Cys Leu Val Thr Thr
                100                 105                 110

Asn Phe Gln Thr Lys Ser Met Ser Ser Met Val Ser Asp Thr Ser Cys
                115                 120                 125

Thr Phe Pro Ser Ser Asp Gly Ile Phe Trp Lys His Trp Ile Gln Thr
    130                 135                 140

Lys Asp Gly Gln Cys Gly Ser Pro Leu Val Ser Thr Arg Asp Gly Phe
145                 150                 155                 160

Ile Val Gly Ile His Ser Ala Ser Asn Phe Thr Asn Thr Asn Asn Tyr
                165                 170                 175

Phe Thr Ser Val Pro Lys Asn Phe Met Glu Leu Leu Thr Asn Gln Glu
            180                 185                 190

Ala Gln Gln Trp Val Ser Gly Trp Arg Leu Asn Ala Asp Ser Val Leu
        195                 200                 205

Trp Gly Gly His Lys Val Phe Met Ser Lys Pro Glu Glu Pro Phe Gln
    210                 215                 220

Pro Val Lys Glu Ala Thr Gln Leu Met Asn Glu Leu Val Tyr Ser Gln
225                 230                 235                 240
```

<210> SEQ ID NO 53
<211> LENGTH: 541
<212> TYPE: PRT
<213> ORGANISM: Artificial Sequence
<220> FEATURE:
<223> OTHER INFORMATION: ZAP70-SH2 domain fused to a TEV protease sequence

<400> SEQUENCE: 53

```
Met Pro Asp Pro Ala Ala His Leu Pro Phe Phe Tyr Gly Ser Ile Ser
1               5                   10                  15

Arg Ala Glu Ala Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
                100                 105                 110
```

```
Gly Val Phe Asp Cys Leu Arg Asp Ala Met Val Arg Asp Tyr Val Arg
            115                 120                 125

Gln Thr Trp Lys Leu Glu Gly Glu Ala Leu Glu Gln Ala Ile Ile Ser
        130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
    210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Pro Thr Leu Pro Ala
            260                 265                 270

His Pro Ser Thr Leu Thr His Pro Ser Gly Gly Gly Ser Gly Gly
        275                 280                 285

Gly Gly Ser Gly Gly Gly Ser Gly Gly Gly Ser Ser Leu Phe
    290                 295                 300

Lys Gly Pro Arg Asp Tyr Asn Pro Ile Ser Ser Thr Ile Cys His Leu
305                 310                 315                 320

Thr Asn Glu Ser Asp Gly His Thr Thr Ser Leu Tyr Gly Ile Gly Phe
                325                 330                 335

Gly Pro Phe Ile Ile Thr Asn Lys His Leu Phe Arg Arg Asn Asn Gly
            340                 345                 350

Thr Leu Leu Val Gln Ser Leu His Gly Val Phe Lys Val Lys Asn Thr
        355                 360                 365

Thr Thr Leu Gln Gln His Leu Ile Asp Gly Arg Asp Met Ile Ile Ile
    370                 375                 380

Arg Met Pro Lys Asp Phe Pro Pro Phe Pro Gln Lys Leu Lys Phe Arg
385                 390                 395                 400

Glu Pro Gln Arg Glu Glu Arg Ile Cys Leu Val Thr Thr Asn Phe Gln
                405                 410                 415

Thr Lys Ser Met Ser Ser Met Val Ser Asp Thr Ser Cys Thr Phe Pro
            420                 425                 430

Ser Ser Asp Gly Ile Phe Trp Lys His Trp Ile Gln Thr Lys Asp Gly
        435                 440                 445

Gln Cys Gly Ser Pro Leu Val Ser Thr Arg Asp Gly Phe Ile Val Gly
    450                 455                 460

Ile His Ser Ala Ser Asn Phe Thr Asn Thr Asn Tyr Phe Thr Ser
465                 470                 475                 480

Val Pro Lys Asn Phe Met Glu Leu Leu Thr Asn Gln Glu Ala Gln Gln
                485                 490                 495

Trp Val Ser Gly Trp Arg Leu Asn Ala Asp Ser Val Leu Trp Gly Gly
            500                 505                 510

His Lys Val Phe Met Ser Lys Pro Glu Glu Pro Phe Gln Pro Val Lys
        515                 520                 525
```

```
Glu Ala Thr Gln Leu Met Asn Glu Leu Val Tyr Ser Gln
        530                 535                 540
```

<210> SEQ ID NO 54
<211> LENGTH: 460
<212> TYPE: PRT
<213> ORGANISM: Artificial Sequence
<220> FEATURE:
<223> OTHER INFORMATION: PTPN6-SH2 domain fused to a TEV protease
      sequence

<400> SEQUENCE: 54

```
Met Val Arg Trp Phe His Arg Asp Leu Ser Gly Leu Asp Ala Glu Thr
1               5                   10                  15

Leu Leu Lys Gly Arg Gly Val His Gly Ser Phe Leu Ala Arg Pro Ser
            20                  25                  30

Arg Lys Asn Gln Gly Asp Phe Ser Leu Ser Val Arg Val Gly Asp Gln
        35                  40                  45

Val Thr His Ile Arg Ile Gln Asn Ser Gly Asp Phe Tyr Asp Leu Tyr
    50                  55                  60

Gly Gly Glu Lys Phe Ala Thr Leu Thr Glu Leu Val Glu Tyr Tyr Thr
65                  70                  75                  80

Gln Gln Gln Gly Val Leu Gln Asp Arg Asp Gly Thr Ile Ile His Leu
                85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125

Glu Pro Trp Thr Phe Leu Val Arg Glu Ser Leu Ser Gln Pro Gly Asp
    130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr Ser Gly Gly Gly Ser Ser Leu Phe Lys
    210                 215                 220

Gly Pro Arg Asp Tyr Asn Pro Ile Ser Ser Thr Ile Cys His Leu Thr
225                 230                 235                 240

Asn Glu Ser Asp Gly His Thr Thr Ser Leu Tyr Gly Ile Gly Phe Gly
                245                 250                 255

Pro Phe Ile Ile Thr Asn Lys His Leu Phe Arg Arg Asn Asn Gly Thr
            260                 265                 270

Leu Leu Val Gln Ser Leu His Gly Val Phe Lys Val Lys Asn Thr Thr
        275                 280                 285

Thr Leu Gln Gln His Leu Ile Asp Gly Arg Asp Met Ile Ile Ile Arg
    290                 295                 300

Met Pro Lys Asp Phe Pro Pro Phe Pro Gln Lys Leu Lys Phe Arg Glu
305                 310                 315                 320

Pro Gln Arg Glu Glu Arg Ile Cys Leu Val Thr Thr Asn Phe Gln Thr
                325                 330                 335

Lys Ser Met Ser Ser Met Val Ser Asp Thr Ser Cys Thr Phe Pro Ser
            340                 345                 350
```

```
Ser Asp Gly Ile Phe Trp Lys His Trp Ile Gln Thr Lys Asp Gly Gln
            355                 360                 365

Cys Gly Ser Pro Leu Val Ser Thr Arg Asp Gly Phe Ile Val Gly Ile
            370                 375                 380

His Ser Ala Ser Asn Phe Thr Asn Thr Asn Asn Tyr Phe Thr Ser Val
385                 390                 395                 400

Pro Lys Asn Phe Met Glu Leu Leu Thr Asn Gln Glu Ala Gln Gln Trp
            405                 410                 415

Val Ser Gly Trp Arg Leu Asn Ala Asp Ser Val Leu Trp Gly Gly His
            420                 425                 430

Lys Val Phe Met Ser Lys Pro Glu Pro Phe Gln Pro Val Lys Glu
            435                 440                 445

Ala Thr Gln Leu Met Asn Glu Leu Val Tyr Ser Gln
            450                 455                 460

<210> SEQ ID NO 55
<211> LENGTH: 438
<212> TYPE: PRT
<213> ORGANISM: Artificial Sequence
<220> FEATURE:
<223> OTHER INFORMATION: membrane tethered transcription factor

<400> SEQUENCE: 55

Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
            35                  40                  45

Thr Asn Val Ser Pro Ala Lys Pro Thr Thr Thr Ala Cys Pro Tyr Ser
50                  55                  60

Asn Pro Ser Leu Cys Ser Gly Gly Gly Ser Pro Ala Pro Arg Pro
65                  70                  75                  80

Pro Thr Pro Ala Pro Thr Ile Ala Ser Gln Pro Leu Ser Leu Arg Pro
            85                  90                  95

Glu Ala Cys Arg Pro Ala Ala Gly Gly Ala Val His Thr Arg Gly Leu
            100                 105                 110

Asp Phe Ala Cys Asp Met Ala Leu Ile Val Leu Gly Gly Val Ala Gly
            115                 120                 125

Leu Leu Leu Phe Ile Gly Leu Gly Ile Phe Phe Cys Val Arg Cys Arg
            130                 135                 140

His Arg Arg Arg Gln Ala Glu Arg Met Ala Gln Ile Lys Arg Val Val
145                 150                 155                 160

Ser Glu Lys Lys Thr Ala Gln Ala Pro His Arg Phe Gln Lys Thr Cys
            165                 170                 175

Ser Pro Ile Ser Gly Gly Gly Ser Glu Asn Leu Tyr Phe Gln Met
            180                 185                 190

Pro Lys Lys Lys Arg Lys Val Ala Pro Pro Thr Asp Val Ser Leu Gly
            195                 200                 205

Asp Glu Leu His Leu Asp Gly Glu Asp Val Ala Met Ala His Ala Asp
            210                 215                 220

Ala Leu Asp Asp Phe Asp Leu Asp Met Leu Gly Asp Gly Asp Ser Pro
225                 230                 235                 240

Gly Pro Gly Phe Thr Pro His Asp Ser Ala Pro Tyr Gly Ala Leu Asp
            245                 250                 255
```

```
Met Ala Asp Phe Glu Phe Glu Gln Met Phe Thr Asp Ala Leu Gly Ile
            260                 265                 270

Asp Glu Tyr Gly Gly Ser Gly Gly Ser Met Gln Ile Leu Val Ala
        275                 280                 285

Ser Asp Ala Thr Met Lys Leu Leu Ser Ser Ile Glu Gln Ala Cys Asp
290                 295                 300

Ile Cys Arg Leu Lys Lys Leu Lys Cys Ser Lys Glu Lys Pro Lys Cys
305                 310                 315                 320

Ala Lys Cys Leu Lys Asn Asn Trp Glu Cys Arg Tyr Ser Pro Lys Thr
                325                 330                 335

Lys Arg Ser Pro Leu Thr Arg Ala His Leu Thr Glu Val Glu Ser Arg
            340                 345                 350

Leu Glu Arg Leu Glu Gln Leu Phe Leu Leu Ile Phe Pro Arg Glu Asp
        355                 360                 365

Leu Asp Met Ile Leu Lys Met Asp Ser Leu Gln Asp Ile Lys Ala Leu
    370                 375                 380

Leu Thr Gly Leu Phe Val Gln Asp Asn Val Asn Lys Asp Ala Val Thr
385                 390                 395                 400

Asp Arg Leu Ala Ser Val Glu Thr Asp Met Pro Leu Thr Leu Arg Gln
                405                 410                 415

His Arg Ile Ser Ala Thr Ser Ser Ser Glu Glu Ser Ser Asn Lys Gly
            420                 425                 430

Gln Arg Gln Leu Thr Val
        435

<210> SEQ ID NO 56
<211> LENGTH: 438
<212> TYPE: PRT
<213> ORGANISM: Artificial Sequence
<220> FEATURE:
<223> OTHER INFORMATION: target receptor

<400> SEQUENCE: 56

Met Ala Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Glu Asp
        35                  40                  45

Ile Tyr Phe Asn Leu Val Trp Tyr Gln Gln Lys Pro Gly Lys Ala Pro
    50                  55                  60

Lys Leu Leu Ile Tyr Asp Thr Asn Arg Leu Ala Asp Gly Val Pro Ser
65                  70                  75                  80

Arg Phe Ser Gly Ser Gly Ser Gly Thr Gln Tyr Thr Leu Thr Ile Ser
                85                  90                  95

Ser Leu Gln Pro Glu Asp Phe Ala Thr Tyr Tyr Cys Gln His Tyr Lys
            100                 105                 110

Asn Tyr Pro Leu Thr Phe Gly Gln Gly Thr Lys Leu Glu Ile Lys Arg
        115                 120                 125

Ser Gly Gly Gly Gly Ser Gly Gly Gly Ser Gly Gly Gly Gly Ser
    130                 135                 140

Gly Gly Gly Gly Ser Arg Ser Glu Val Gln Leu Val Glu Ser Gly Gly
145                 150                 155                 160

Gly Leu Val Gln Pro Gly Gly Ser Leu Arg Leu Ser Cys Ala Ala Ser
                165                 170                 175
```

Gly Phe Thr Leu Ser Asn Tyr Gly Met His Trp Ile Arg Gln Ala Pro
            180                 185                 190

Gly Lys Gly Leu Glu Trp Val Ser Ile Ser Leu Asn Gly Gly Ser
        195                 200                 205

Thr Tyr Tyr Arg Asp Ser Val Lys Gly Arg Phe Thr Ile Ser Arg Asp
210                 215                 220

Asn Ala Lys Ser Thr Leu Tyr Leu Gln Met Asn Ser Leu Arg Ala Glu
225                 230                 235                 240

Asp Thr Ala Val Tyr Tyr Cys Ala Ala Gln Asp Ala Tyr Thr Gly Gly
                245                 250                 255

Tyr Phe Asp Tyr Trp Gly Gln Gly Thr Leu Val Thr Val Ser Ser Met
            260                 265                 270

Asp Pro Ala Thr Thr Thr Lys Pro Val Leu Arg Thr Pro Ser Pro Val
        275                 280                 285

His Pro Thr Gly Thr Ser Gln Pro Gln Arg Pro Glu Asp Cys Arg Pro
    290                 295                 300

Arg Gly Ser Val Lys Gly Thr Gly Leu Asp Phe Ala Cys Asp Ile Tyr
305                 310                 315                 320

Val Gly Val Val Gly Leu Leu Gly Ser Leu Val Leu Leu Val Trp
                325                 330                 335

Val Leu Ala Val Ile Cys Ser Arg Ala Ala Arg Gly Thr Ile Gly Ala
            340                 345                 350

Arg Arg Thr Gly Gln Pro Leu Lys Glu Asp Pro Ser Ala Val Pro Val
        355                 360                 365

Phe Ser Val Asp Tyr Gly Glu Leu Asp Phe Gln Trp Arg Glu Lys Thr
370                 375                 380

Pro Glu Pro Pro Val Pro Cys Val Pro Glu Gln Thr Glu Tyr Ala Thr
385                 390                 395                 400

Ile Val Phe Pro Ser Gly Met Gly Thr Ser Ser Pro Ala Arg Arg Gly
                405                 410                 415

Ser Ala Asp Gly Pro Arg Ser Ala Gln Pro Leu Arg Pro Glu Asp Gly
            420                 425                 430

His Cys Ser Trp Pro Leu
            435

<210> SEQ ID NO 57
<211> LENGTH: 509
<212> TYPE: PRT
<213> ORGANISM: Artificial Sequence
<220> FEATURE:
<223> OTHER INFORMATION: receptor containing a CAR against CD19 with a
      cleavable CD3-zeta endodomain

<400> SEQUENCE: 57

Met Ser Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile

```
                  85                  90                  95
Ser Asn Leu Glu Gln Glu Asp Ile Ala Thr Tyr Phe Cys Gln Gln Gly
            100                 105                 110
Asn Thr Leu Pro Tyr Thr Phe Gly Gly Gly Thr Lys Leu Glu Ile Thr
            115                 120                 125
Lys Ala Gly Gly Gly Ser Gly Gly Gly Ser Gly Gly Gly Gly
            130                 135                 140
Ser Gly Gly Gly Ser Glu Val Lys Leu Gln Glu Ser Gly Pro Gly
145                 150                 155                 160
Leu Val Ala Pro Ser Gln Ser Leu Ser Val Thr Cys Thr Val Ser Gly
                165                 170                 175
Val Ser Leu Pro Asp Tyr Gly Val Ser Trp Ile Arg Gln Pro Pro Arg
                180                 185                 190
Lys Gly Leu Glu Trp Leu Gly Val Ile Trp Gly Ser Glu Thr Thr Tyr
                195                 200                 205
Tyr Asn Ser Ala Leu Lys Ser Arg Leu Thr Ile Ile Lys Asp Asn Ser
            210                 215                 220
Lys Ser Gln Val Phe Leu Lys Met Asn Ser Leu Gln Thr Asp Asp Thr
225                 230                 235                 240
Ala Ile Tyr Tyr Cys Ala Lys His Tyr Tyr Gly Gly Ser Tyr Ala
                245                 250                 255
Met Asp Tyr Trp Gly Gln Gly Thr Ser Val Thr Val Ser Ser Asp Pro
            260                 265                 270
Thr Thr Thr Pro Ala Pro Arg Pro Pro Thr Pro Ala Pro Thr Ile Ala
            275                 280                 285
Ser Gln Pro Leu Ser Leu Arg Pro Glu Ala Cys Arg Pro Ala Ala Gly
            290                 295                 300
Gly Ala Val His Thr Arg Gly Leu Asp Phe Ala Cys Asp Ile Phe Trp
305                 310                 315                 320
Val Leu Val Val Val Gly Gly Val Leu Ala Cys Tyr Ser Leu Leu Val
                325                 330                 335
Thr Val Ala Phe Ile Ile Phe Trp Val Arg Cys Arg His Arg Arg
                340                 345                 350
Gln Ala Glu Arg Met Ala Gln Ile Lys Arg Val Val Ser Glu Lys Lys
            355                 360                 365
Thr Ala Gln Ala Pro His Arg Phe Gln Lys Thr Cys Ser Pro Ile Ser
            370                 375                 380
Gly Gly Gly Gly Ser Glu Asn Leu Tyr Phe Gln Met Arg Arg Val Lys
385                 390                 395                 400
Phe Ser Arg Ser Ala Asp Ala Pro Ala Tyr Gln Gln Gly Gln Asn Gln
                405                 410                 415
Leu Tyr Asn Glu Leu Asn Leu Gly Arg Arg Glu Glu Tyr Asp Val Leu
            420                 425                 430
Asp Lys Arg Arg Gly Arg Asp Pro Glu Met Gly Gly Lys Pro Arg Arg
            435                 440                 445
Lys Asn Pro Gln Glu Gly Leu Tyr Asn Glu Leu Gln Lys Asp Lys Met
            450                 455                 460
Ala Glu Ala Tyr Ser Glu Ile Gly Met Lys Gly Glu Arg Arg Arg Gly
465                 470                 475                 480
Lys Gly His Asp Gly Leu Tyr Gln Gly Leu Ser Thr Ala Thr Lys Asp
                485                 490                 495
Thr Tyr Asp Ala Leu His Met Gln Ala Leu Pro Pro Arg
            500                 505
```

<210> SEQ ID NO 58
<211> LENGTH: 827
<212> TYPE: PRT
<213> ORGANISM: Artificial Sequence
<220> FEATURE:
<223> OTHER INFORMATION: receptor containing a CAR against CD19 with a
      CD3-zeta endodomain and a cleavable CD148 endodomain

<400> SEQUENCE: 58

```
Met Ser Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Lys Ala Gly Gly Gly Gly Ser Gly Gly Gly Gly Ser Gly Gly Gly Gly
    130                 135                 140

Ser Gly Gly Gly Gly Ser Glu Val Lys Leu Gln Glu Ser Gly Pro Gly
145                 150                 155                 160

Leu Val Ala Pro Ser Gln Ser Leu Ser Val Thr Cys Thr Val Ser Gly
                165                 170                 175

Val Ser Leu Pro Asp Tyr Gly Val Ser Trp Ile Arg Gln Pro Pro Arg
            180                 185                 190

Lys Gly Leu Glu Trp Leu Gly Val Ile Trp Gly Ser Glu Thr Thr Tyr
        195                 200                 205

Tyr Asn Ser Ala Leu Lys Ser Arg Leu Thr Ile Ile Lys Asp Asn Ser
    210                 215                 220

Lys Ser Gln Val Phe Leu Lys Met Asn Ser Leu Gln Thr Asp Asp Thr
225                 230                 235                 240

Ala Ile Tyr Tyr Cys Ala Lys His Tyr Tyr Gly Gly Ser Tyr Ala
                245                 250                 255

Met Asp Tyr Trp Gly Gln Gly Thr Ser Val Thr Val Ser Ser Asp Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Phe Trp
305                 310                 315                 320

Val Leu Val Val Val Gly Gly Val Leu Ala Cys Tyr Ser Leu Leu Val
                325                 330                 335

Thr Val Ala Phe Ile Ile Phe Trp Val Arg Arg Val Lys Phe Ser Arg
            340                 345                 350

Ser Ala Asp Ala Pro Ala Tyr Gln Gln Gly Gln Asn Gln Leu Tyr Asn
```

```
            355                 360                 365
Glu Leu Asn Leu Gly Arg Arg Glu Glu Tyr Asp Val Leu Asp Lys Arg
    370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
                420                 425                 430

Asp Gly Leu Tyr Gln Gly Leu Ser Thr Ala Thr Lys Asp Thr Tyr Asp
            435                 440                 445

Ala Leu His Met Gln Ala Leu Pro Pro Arg Glu Asn Leu Tyr Phe Gln
        450                 455                 460

Met Ala Val Phe Gly Cys Ile Phe Gly Ala Leu Val Ile Val Thr Val
465                 470                 475                 480

Gly Gly Phe Ile Phe Trp Arg Lys Lys Arg Lys Asp Ala Lys Asn Asn
                485                 490                 495

Glu Val Ser Phe Ser Gln Ile Lys Pro Lys Lys Ser Lys Leu Ile Arg
                500                 505                 510

Val Glu Asn Phe Glu Ala Tyr Phe Lys Lys Gln Gln Ala Asp Ser Asn
            515                 520                 525

Cys Gly Phe Ala Glu Glu Tyr Glu Asp Leu Lys Leu Val Gly Ile Ser
530                 535                 540

Gln Pro Lys Tyr Ala Ala Glu Leu Ala Glu Asn Arg Gly Lys Asn Arg
545                 550                 555                 560

Tyr Asn Asn Val Leu Pro Tyr Asp Ile Ser Arg Val Lys Leu Ser Val
                565                 570                 575

Gln Thr His Ser Thr Asp Asp Tyr Ile Asn Ala Asn Tyr Met Pro Gly
            580                 585                 590

Tyr His Ser Lys Lys Asp Phe Ile Ala Thr Gln Gly Pro Leu Pro Asn
        595                 600                 605

Thr Leu Lys Asp Phe Trp Arg Met Val Trp Glu Lys Asn Val Tyr Ala
    610                 615                 620

Ile Ile Met Leu Thr Lys Cys Val Glu Gln Gly Arg Thr Lys Cys Glu
625                 630                 635                 640

Glu Tyr Trp Pro Ser Lys Gln Ala Gln Asp Tyr Gly Asp Ile Thr Val
                645                 650                 655

Ala Met Thr Ser Glu Ile Val Leu Pro Glu Trp Thr Ile Arg Asp Phe
            660                 665                 670

Thr Val Lys Asn Ile Gln Thr Ser Glu Ser His Pro Leu Arg Gln Phe
        675                 680                 685

His Phe Thr Ser Trp Pro Asp His Gly Val Pro Asp Thr Thr Asp Leu
    690                 695                 700

Leu Ile Asn Phe Arg Tyr Leu Val Arg Asp Tyr Met Lys Gln Ser Pro
705                 710                 715                 720

Pro Glu Ser Pro Ile Leu Val His Cys Ser Ala Gly Val Gly Arg Thr
                725                 730                 735

Gly Thr Phe Ile Ala Ile Asp Arg Leu Ile Tyr Gln Ile Glu Asn Glu
            740                 745                 750

Asn Thr Val Asp Val Tyr Gly Ile Val Tyr Asp Leu Arg Met His Arg
        755                 760                 765

Pro Leu Met Val Gln Thr Glu Asp Gln Tyr Val Phe Leu Asn Gln Cys
    770                 775                 780
```

```
Val Leu Asp Ile Val Arg Ser Gln Lys Asp Ser Lys Val Asp Leu Ile
785                 790                 795                 800

Tyr Gln Asn Thr Thr Ala Met Thr Ile Tyr Glu Asn Leu Ala Pro Val
                805                 810                 815

Thr Thr Phe Gly Lys Thr Asn Gly Tyr Ile Ala
            820                 825
```

<210> SEQ ID NO 59
<211> LENGTH: 20
<212> TYPE: PRT
<213> ORGANISM: Artificial Sequence
<220> FEATURE:
<223> OTHER INFORMATION: 2a self-cleaving peptide

<400> SEQUENCE: 59

```
Arg Ala Glu Gly Arg Gly Ser Leu Leu Thr Cys Gly Asp Val Glu Glu
1               5                   10                  15

Asn Pro Gly Pro
            20
```

<210> SEQ ID NO 60
<211> LENGTH: 20
<212> TYPE: PRT
<213> ORGANISM: Artificial Sequence
<220> FEATURE:
<223> OTHER INFORMATION: 2a self-cleaving peptide

<400> SEQUENCE: 60

```
Gln Cys Thr Asn Tyr Ala Leu Leu Lys Leu Ala Gly Asp Val Glu Ser
1               5                   10                  15

Asn Pro Gly Pro
            20
```

<210> SEQ ID NO 61
<211> LENGTH: 563
<212> TYPE: PRT
<213> ORGANISM: Artificial Sequence
<220> FEATURE:
<223> OTHER INFORMATION: dual SH2 domains from SHP-2 fused to ZAP70
      kinase domain

<400> SEQUENCE: 61

```
Trp Phe His Pro Asn Ile Thr Gly Val Glu Ala Glu Asn Leu Leu Leu
1               5                   10                  15

Thr Arg Gly Val Asp Gly Ser Phe Leu Ala Arg Pro Ser Lys Ser Asn
                20                  25                  30

Pro Gly Asp Phe Thr Leu Ser Val Arg Arg Asn Gly Ala Val Thr His
            35                  40                  45

Ile Lys Ile Gln Asn Thr Gly Asp Tyr Tyr Asp Leu Tyr Gly Gly Glu
    50                  55                  60

Lys Phe Ala Thr Leu Ala Glu Leu Val Gln Tyr Tyr Met Glu His His
65                  70                  75                  80

Gly Gln Leu Lys Glu Lys Asn Gly Asp Val Ile Glu Leu Lys Tyr Pro
                85                  90                  95

Leu Asn Cys Ala Asp Pro Thr Ser Glu Arg Trp Phe His Gly His Leu
            100                 105                 110

Ser Gly Lys Glu Ala Glu Lys Leu Leu Thr Glu Lys Gly Lys His Gly
        115                 120                 125

Ser Phe Leu Val Arg Glu Ser Gln Ser His Pro Gly Asp Phe Val Leu
    130                 135                 140
```

```
Ser Val Arg Thr Gly Asp Asp Lys Gly Glu Ser Asn Asp Gly Lys Ser
145                 150                 155                 160

Lys Val Thr His Val Met Ile Arg Cys Gln Glu Leu Lys Tyr Asp Val
            165                 170                 175

Gly Gly Gly Glu Arg Phe Asp Ser Leu Thr Asp Leu Val Glu His Tyr
        180                 185                 190

Lys Lys Asn Pro Met Val Glu Thr Leu Gly Thr Val Leu Gln Leu Lys
            195                 200                 205

Gln Pro Leu Asn Thr Thr Arg Ile Asn Pro Asn Ser Ser Ala Ser Asn
        210                 215                 220

Ala Ser Gly Ala Ala Ala Pro Thr Leu Pro Ala His Pro Ser Thr Leu
225                 230                 235                 240

Thr His Pro Gln Arg Arg Ile Asp Thr Leu Asn Ser Asp Gly Tyr Thr
                245                 250                 255

Pro Glu Pro Ala Arg Ile Thr Ser Pro Asp Lys Pro Arg Pro Met Pro
            260                 265                 270

Met Asp Thr Ser Val Tyr Glu Ser Pro Tyr Ser Asp Pro Glu Glu Leu
            275                 280                 285

Lys Asp Lys Lys Leu Phe Leu Lys Arg Asp Asn Leu Leu Ile Ala Asp
290                 295                 300

Ile Glu Leu Gly Cys Gly Asn Phe Gly Ser Val Arg Gln Gly Val Tyr
305                 310                 315                 320

Arg Met Arg Lys Lys Gln Ile Asp Val Ala Ile Lys Val Leu Lys Gln
                325                 330                 335

Gly Thr Glu Lys Ala Asp Thr Glu Glu Met Met Arg Glu Ala Gln Ile
            340                 345                 350

Met His Gln Leu Asp Asn Pro Tyr Ile Val Arg Leu Ile Gly Val Cys
        355                 360                 365

Gln Ala Glu Ala Leu Met Leu Val Met Glu Met Ala Gly Gly Gly Pro
370                 375                 380

Leu His Lys Phe Leu Val Gly Lys Arg Glu Glu Ile Pro Val Ser Asn
385                 390                 395                 400

Val Ala Glu Leu Leu His Gln Val Ser Met Gly Met Lys Tyr Leu Glu
                405                 410                 415

Glu Lys Asn Phe Val His Arg Asp Leu Ala Ala Arg Asn Val Leu Leu
            420                 425                 430

Val Asn Arg His Tyr Ala Lys Ile Ser Asp Phe Gly Leu Ser Lys Ala
        435                 440                 445

Leu Gly Ala Asp Asp Ser Tyr Tyr Thr Ala Arg Ser Ala Gly Lys Trp
450                 455                 460

Pro Leu Lys Trp Tyr Ala Pro Glu Cys Ile Asn Phe Arg Lys Phe Ser
465                 470                 475                 480

Ser Arg Ser Asp Val Trp Ser Tyr Gly Val Thr Met Trp Glu Ala Leu
                485                 490                 495

Ser Tyr Gly Gln Lys Pro Tyr Lys Lys Met Lys Gly Pro Glu Val Met
            500                 505                 510

Ala Phe Ile Glu Gln Gly Lys Arg Met Glu Cys Pro Pro Glu Cys Pro
        515                 520                 525

Pro Glu Leu Tyr Ala Leu Met Ser Asp Cys Trp Ile Tyr Lys Trp Glu
            530                 535                 540

Asp Arg Pro Asp Phe Leu Thr Val Glu Gln Arg Met Arg Ala Cys Tyr
545                 550                 555                 560
```

Tyr Ser Leu

<210> SEQ ID NO 62
<211> LENGTH: 567
<212> TYPE: PRT
<213> ORGANISM: Artificial Sequence
<220> FEATURE:
<223> OTHER INFORMATION: dual SHP-2 SH2 domain fused to an Akt kinase
      domain

<400> SEQUENCE: 62

```
Trp Phe His Pro Asn Ile Thr Gly Val Glu Ala Glu Asn Leu Leu Leu
1               5                   10                  15

Thr Arg Gly Val Asp Gly Ser Phe Leu Ala Arg Pro Ser Lys Ser Asn
            20                  25                  30

Pro Gly Asp Phe Thr Leu Ser Val Arg Arg Asn Gly Ala Val Thr His
        35                  40                  45

Ile Lys Ile Gln Asn Thr Gly Asp Tyr Tyr Asp Leu Tyr Gly Gly Glu
    50                  55                  60

Lys Phe Ala Thr Leu Ala Glu Leu Val Gln Tyr Tyr Met Glu His His
65                  70                  75                  80

Gly Gln Leu Lys Glu Lys Asn Gly Asp Val Ile Glu Leu Lys Tyr Pro
                85                  90                  95

Leu Asn Cys Ala Asp Pro Thr Ser Glu Arg Trp Phe His Gly His Leu
            100                 105                 110

Ser Gly Lys Glu Ala Glu Lys Leu Leu Thr Glu Lys Gly Lys His Gly
        115                 120                 125

Ser Phe Leu Val Arg Glu Ser Gln Ser His Pro Gly Asp Phe Val Leu
    130                 135                 140

Ser Val Arg Thr Gly Asp Asp Lys Gly Glu Ser Asn Asp Gly Lys Ser
145                 150                 155                 160

Lys Val Thr His Val Met Ile Arg Cys Gln Glu Leu Lys Tyr Asp Val
                165                 170                 175

Gly Gly Gly Glu Arg Phe Asp Ser Leu Thr Asp Leu Val Glu His Tyr
            180                 185                 190

Lys Lys Asn Pro Met Val Glu Thr Leu Gly Thr Val Leu Gln Leu Lys
        195                 200                 205

Gln Pro Leu Asn Thr Thr Arg Ile Asn Ala Glu Glu Met Glu Val Ser
    210                 215                 220

Leu Ala Lys Pro Lys His Arg Val Thr Met Asn Glu Phe Glu Tyr Leu
225                 230                 235                 240

Lys Leu Leu Gly Lys Gly Thr Phe Gly Lys Val Ile Leu Val Lys Glu
                245                 250                 255

Lys Ala Thr Gly Arg Tyr Tyr Ala Met Lys Ile Leu Lys Lys Glu Val
            260                 265                 270

Ile Val Ala Lys Asp Glu Val Ala His Thr Leu Thr Glu Asn Arg Val
        275                 280                 285

Leu Gln Asn Ser Arg His Pro Phe Leu Thr Ala Leu Lys Tyr Ser Phe
    290                 295                 300

Gln Thr His Asp Arg Leu Cys Phe Val Met Glu Tyr Ala Asn Gly Gly
305                 310                 315                 320

Glu Leu Phe Phe His Leu Ser Arg Glu Arg Val Phe Ser Glu Asp Arg
                325                 330                 335

Ala Arg Phe Tyr Gly Ala Glu Ile Val Ser Ala Leu Asp Tyr Leu His
            340                 345                 350
```

```
Ser Glu Lys Asn Val Val Tyr Arg Asp Leu Lys Leu Glu Asn Leu Met
            355                 360                 365

Leu Asp Lys Asp Gly His Ile Lys Ile Thr Asp Phe Gly Leu Cys Lys
        370                 375                 380

Glu Gly Ile Lys Asp Gly Ala Thr Met Lys Thr Phe Cys Gly Thr Pro
385                 390                 395                 400

Glu Tyr Leu Ala Pro Glu Val Leu Glu Asp Asn Asp Tyr Gly Arg Ala
                405                 410                 415

Val Asp Trp Trp Gly Leu Gly Val Val Met Tyr Glu Met Met Cys Gly
            420                 425                 430

Arg Leu Pro Phe Tyr Asn Gln Asp His Glu Lys Leu Phe Glu Leu Ile
        435                 440                 445

Leu Met Glu Glu Ile Arg Phe Pro Arg Thr Leu Gly Pro Glu Ala Lys
    450                 455                 460

Ser Leu Leu Ser Gly Leu Leu Lys Lys Asp Pro Lys Gln Arg Leu Gly
465                 470                 475                 480

Gly Gly Ser Glu Asp Ala Lys Glu Ile Met Gln His Arg Phe Phe Ala
                485                 490                 495

Gly Ile Val Trp Gln His Val Tyr Glu Lys Lys Leu Ser Pro Pro Phe
            500                 505                 510

Lys Pro Gln Val Thr Ser Glu Thr Asp Thr Arg Tyr Phe Asp Glu Glu
        515                 520                 525

Phe Thr Ala Gln Met Ile Thr Ile Thr Pro Pro Asp Gln Asp Asp Ser
    530                 535                 540

Met Glu Cys Val Asp Ser Glu Arg Arg Pro His Phe Pro Gln Phe Ser
545                 550                 555                 560

Tyr Ser Ala Ser Gly Thr Ala
                565

<210> SEQ ID NO 63
<211> LENGTH: 6
<212> TYPE: PRT
<213> ORGANISM: Artificial Sequence
<220> FEATURE:
<223> OTHER INFORMATION: ITIM conserved sequence
<220> FEATURE:
<221> NAME/KEY: MISC_FEATURE
<222> LOCATION: (1)..(1)
<223> OTHER INFORMATION: Xaa may be Ser, Ile, Val or Leu
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa may be Ile, Val or Leu

<400> SEQUENCE: 63

Xaa Xaa Tyr Xaa Xaa Xaa
1               5
```

CHIMERIC T CELL

FIELD OF THE INVENTION

The present invention relates to fusion proteins and truncated proteins which enable the signalling pathways which are propagated following immune cell activation to be manipulated or modulated.

BACKGROUND TO THE INVENTION

Adoptive immunotherapy with autologous T cells involves the isolation of T cells from the patient followed by their stimulation, modification and/or expansion ex vivo in order to generate a population of T cells which display anti-tumour specificities. Once re-infused into the patient these cells are capable of recognizing tumour-expressed antigens and mediating tumour rejection.

This approach has already been shown in a number of trials in different settings to have the potential to be a powerful, effective and long-lasting treatment for cancer. For instance, EBV-driven tumours, such as lymphoproliferative disease following solid organ transplant can be effectively treated by ex vivo expanded EBV specific T-cells.

A similar therapy for non-viral malignancies involves tumour infiltrating lymphocytes (TILs) which are isolated from resected fragments of tumour and then subjected to stimulation and expansion with autologous tumour samples. Expanded T cell cultures which show tumour reactivity can then be re-infused into the patient.

Rather than selecting and refining T cell specificities with repeated exposure to antigens, the desired anti-tumour specificity can be conferred onto the T cells through gene modification and the introduction of either a tumour-specific T cell receptor (TCR) or a chimeric antigen receptor (CAR). These cells are expanded ex vivo in order to produce sufficient numbers of cells to achieve meaningful clinical responses within the patient.

However, the approaches detailed above have limitations. For instance, adoptively transferred T-cells may show limited persistence and expansion in vivo due to insufficient signalling, lack of IL2 or differentiation. By way of further example, adoptively transferred T-cells may succumb to inhibitory stimuli within the tumour microenvironment. For example they may become exhausted, undergo activation induced cell death consequent to over activation, or may cause on-target off-tumour effects.

Another promising approach to activating therapeutic anti-tumour immunity is the blockade of immune checkpoints. Immune checkpoints refer to the various inhibitory pathways of the immune system that are important for maintaining self-tolerance and modulating the duration and amplitude of physiological immune responses in peripheral tissues.

It is known that tumours exploit certain immune-checkpoint pathways as a major mechanism of immune resistance, particularly against T cells that are specific for tumour antigens. Many of the immune checkpoints are initiated by ligand-receptor interactions, meaning that they can be blocked by antibodies or modulated by recombinant forms of ligands or receptors. Cytotoxic T-lymphocyte-associated antigen 4 (CTLA4) antibodies were the first of this class of immunotherapeutics to achieve US Food and Drug Administration (FDA) approval. More recently, blockers of additional immune-checkpoint proteins, such as programmed cell death protein 1 (PD1), have been developed and shown to enhance anti-tumour immunity.

One problem with the use of immune checkpoint inhibitors is that there are a multitude of inhibitory pathways triggered by a multitude of ligand:receptor interactions. The use of an antibody or a recombinant form of the ligand/receptor will only block one such inhibitory pathway, leaving the possibility open that the tumour can compensate for the specific immune checkpoint block using other molecules.

SUMMARY OF ASPECTS OF THE INVENTION

The present inventors have developed a system for modulating and/or manipulating signal transduction pathways in immune cells, such as T cells and natural killer (NK) cells.

Intracellular signalling pathways are initiated and controlled by the reversible post-translational modification of proteins. The present inventors have determined that activating and inhibitory signalling pathways in T cells can be modulated and/or manipulated by fusion proteins or truncated proteins comprising SH2 domains from immediate T-cell signal transduction proteins. In other words, activating and inhibitory signalling pathways in T cells can be modulated and/or manipulated by fusion proteins or truncated proteins comprising SH2 domains from proteins which are capable of binding phosphorylated immunoreceptor tyrosine-based activation motifs (ITAM) or phosphorylated immunoreceptor tyrosine-based inhibition motifs (ITIM).

Thus in a first aspect, the present invention provides a cell which comprises a chimeric antigen receptor (CAR) and a signal transduction modifying protein, selected from one of the following:

(i) a truncated protein which comprises an SH2 domain from a protein which binds a phosphorylated immunoreceptor tyrosine-based activation motif (ITAM), but lacks a kinase domain;

(ii) a truncated protein which comprises an SH2 domain from a protein which binds a phosphorylated immunoreceptor tyrosine-based inhibition motif (ITIM) but lacks a phosphatase domain;

(iii) a fusion protein which comprises (a) an SH2 domain from a protein which binds a phosphorylated immunoreceptor tyrosine-based activation motif (ITAM) or from a protein which binds a phosphorylated immunoreceptor tyrosine-based inhibition motif (ITIM); and (ii) a heterologous domain.

The signal transduction modifying protein may be a truncated protein which comprises a ZAP70 SH2 domain but lacks a ZAP70 kinase domain.

The signal transduction modifying protein may be a truncated protein which comprises an PTPN6 SH2 but lacks a PTPN6 phosphatase domain.

The signal transduction modifying protein may be a truncated protein which comprises a SHP-2 SH2 domain but lacks a SHP-2 phosphatase domain.

The signal transduction modifying protein may be a fusion protein which comprises (i) an SH2 domain from a protein which binds a phosphorylated immunoreceptor tyrosine-based activation motif (ITAM); and (ii) a phosphatase domain.

The fusion protein may, for example, comprise a ZAP70 SH2 domain, a PTPN6 or an SHP-2 phosphatase domain.

The signal transduction modifying protein may be a fusion protein which comprises (i) an SH2 domain from a protein which binds a phosphorylated immunoreceptor tyrosine-based inhibition motif (ITIM); and (ii) a kinase domain.

The fusion protein may comprise an SH2 domain from PTPN6 or SHP-2.

The fusion protein may comprise a Zap70 kinase domain

The fusion protein may comprise an AKT or JAK kinase domain.

The signal transduction modifying protein may be a fusion protein which comprises (i) an SH2 domain from a protein which binds a phosphorylated immunoreceptor tyrosine-based activation motif (ITAM) or from a protein which binds a phosphorylated immunoreceptor tyrosine-based inhibition motif (ITIM); and (ii) a heterologous signalling domain.

The fusion protein may comprise an SH2 domain from ZAP70, PTPN6 or SHP-2.

The heterologous signalling domain may be from a signalling molecule which is not usually activated by an ITAM or ITIM containing receptor.

The heterologous signalling domain may be a co-stimulatory domain. In this respect, the fusion protein may comprise a CD28, OX40 or 41BB co-stimulatory domain.

The heterologous signalling domain may be an inhibitory domain. In this respect, the inhibitory domain may be or comprise the endodomain of CD148 or CD45. Alternatively, the heterologous signalling domain is or comprises the endodomain of ICOS, CD27, BTLA, CD30, GITR or HVEM.

The signal transduction modifying protein may be a fusion protein which comprises (i) an SH2 domain from a protein which binds a phosphorylated immunoreceptor tyrosine-based activation motif (ITAM); and (ii) an ITAM-containing domain.

The fusion protein may comprises a ZAP70 SH2 domain.

The ITAM-containing domain may be or comprise the endodomain of CD3-Zeta.

The signal transduction modifying protein may be a fusion protein which comprises (i) an SH2 domain from a protein which binds a phosphorylated immunoreceptor tyrosine-based inhibition motif (ITIM); and (ii) an ITIM-containing domain.

The fusion protein may comprise an SH2 domain from PTPN6 or SHP-2.

The ITIM-containing domain may be or comprise the endodomain from PD1, PDCD1, BTLA4, LILRB1, LAIR1, CTLA4, KIR2DL1, KIR2DL4, KIR2DL5, KIR3DL1 or KIR3DL3.

The signal transduction modifying protein may be a fusion protein which comprises (i) an SH2 domain from a protein which binds a phosphorylated immunoreceptor tyrosine-based activation motif (ITAM) or from a protein which binds a phosphorylated immunoreceptor tyrosine-based inhibition motif (ITIM); and (ii) a protease domain.

The fusion protein may comprise an SH2 domain from ZAP70, PTPN6 or SHP-2.

The protease domain may be or comprise Tobacco Etch Virus Protease (TeV).

The cell may also comprises a membrane-tethered transcription factor having a protease cleavage site. Cleavage at the protease cleavage site may release the transcription factor leading to increased expression of a target gene.

The target gene encodes a cytokine, for example a cytokine selected from the following group: IL-2, IL-7, IL-15 and IL-12.

In this embodiment, the chimeric antigen receptor (CAR) may be a target CAR which comprises an intracellular protease cleavage site.

The target CAR may comprise an activatory or co-stimulatory endodomain and cleavage at the protease cleavage site removes the endodomain from the target CAR.

Alternatively, the target CAR may comprise an inhibitory endodomain and cleavage at the protease cleavage site removes the inhibitory endodomain from the target CAR. The inhibitory endodomain may comprise a CD148 or CD45 endodomain.

The cell of the present invention may comprise two CARs: an activating CAR comprising an ITAM-containing endodomain; and a target CAR as defined above.

Alternatively, the cell of the present invention may comprise two CARs: an inhibitory CAR comprising an ITIM-containing endodomain; and a target CAR as defined above.

In a second aspect, the present invention provides a nucleic acid construct, which comprises:
 a first nucleic acid sequence encoding a chimeric antigen receptor; and
 a second nucleic acid sequence encoding a truncated protein or a fusion protein as defined in connection with the first aspect of the invention.

The nucleic acid construct may also comprise a third nucleic acid sequence encoding a membrane-tethered transcription factor as defined above.

The nucleic acid construct may also comprise a third nucleic acid sequence encoding a target CAR as defined above.

The nucleic acid construct may also comprise a fourth nucleic acid sequence encoding an activating CAR or an inhibitory CAR as defined above.

In a third aspect, the vector which comprises a nucleic acid construct according to the second aspect of the invention or first and second, and optionally third and/or fourth, nucleic acid sequences as defined above.

There is also provided a set of vectors which comprises first and second, and optionally third and/or fourth, nucleic acid sequences as defined above.

The vector or set of vectors may be retroviral or lentiviral vector(s).

In a fourth aspect, there is provided a pharmaceutical composition comprising a plurality of cells according to the first aspect of the invention.

In a fifth aspect, there is provided a pharmaceutical composition according to the fourth aspect of the invention for use in treating and/or preventing a disease.

In a sixth aspect, there is provided method for treating and/or preventing a disease, which comprises the step of administering a pharmaceutical composition according to the fourth aspect of the invention to a subject.

The method may comprise the following steps:
 (i) isolation of a cell containing sample from a subject;
 (ii) transduction or transfection of the cells with a nucleic acid construct according to the second aspect of the invention, a vector or set of vectors according to the third aspect of the invention; and
 (iii) administering the cells from (ii) to the subject.

In a seventh aspect there is provided the use of a pharmaceutical composition according to the fourth aspect of the invention in the manufacture of a medicament for the treatment and/or prevention of a disease.

The disease may be cancer.

In an eighth aspect, there is provided a method for making a cell according to the first aspect of the invention, which comprises the step of introducing: a nucleic acid construct according to the second aspect of the invention, a vector or set of vectors according to the third aspect of the invention, into the cell.

The cell may be from a sample isolated from a subject.

In a first further aspect, the present invention also provides a fusion protein which comprises: (i) a ZAP70 or PTPN6 SH2 domain; and (ii) a heterologous domain.

The fusion protein may comprise a ZAP70 SH2 domain and an ITAM-containing domain. The ITAM-containing domain may be or comprise the endodomain of CD3-Zeta.

The fusion protein may comprise a PTPN6 SH2 domain and an ITIM-containing domain. The ITIM-containing domain may be or comprise the endodomain from PDCD1, BTLA4, LILRB1, LAIR1, CTLA4, KIR2DL1, KIR2DL4, KIR2DL5, KIR3DL1 or KIR3DL3.

The fusion protein may comprise a PTPN6 SH2 domain and fused to a ZAP70 kinase domain.

The fusion protein may comprise a ZAP70 SH2 domain fused to a PTPN6 kinase domain.

The fusion protein may comprise: (i) a ZAP70 or PTPN6 SH2 domain; and (ii) a heterologous signalling domain.

The heterologous signalling domain may be from a signalling molecule which is not usually activated by an ITAM containing receptor. The heterologous signalling domain may be or comprise the endodomain of CD28, 41BB or OX40. The heterologous signalling domain may be or comprise the endodomain of ICOS, CD27, BTLA, CD30, GITR or HVEM.

The fusion protein may comprise: (i) a ZAP70 or PTPN6 SH2 domain; and (ii) a kinase domain.

The kinase domain may be or comprise an AKT or JAK kinase domain.

The fusion protein may comprise: (i) a ZAP70 or PTPN6 SH2 domain; and (ii) a protease domain.

The protease domain may be or comprise Tobacco Etch Virus Protease (TeV).

In a second further aspect the present invention provides a truncated protein which comprises the ZAP70 SH2 domain but lacks the ZAP70 kinase domain.

In a third further aspect the present invention provides a truncated protein which comprises the PTPN6 SH2 domain but lacks the PTPN6 kinase domain.

The present invention also provides a signalling system comprising:
(i) a receptor comprising an antigen-binding domain, a transmembrane domain and an intracellular signalling domain which comprises a CD3 zeta endodomain; and
(ii) a fusion protein according to the first further aspect of the invention which comprises a ZAP70 SH2 domain; or a truncated protein according to the second further aspect of the invention;
wherein binding of antigen to the antigen-binding domain results in binding between the CD3 zeta endodomain and the fusion/truncated protein.

The present invention also provides a signalling system comprising:
(i) a receptor comprising an antigen-binding domain, a transmembrane domain and an intracellular signalling domain which comprises a PTPN6 binding domain; and
(ii) a fusion protein according to the first further aspect of the invention which comprises a PTPN6 SH2 domain; or a truncated protein according to the third further aspect of the invention
wherein binding of antigen to the antigen-binding domain results in binding between the PTPN6 binding domain and the fusion/truncated protein.

The receptor may be a T-cell receptor (TCR) or a chimeric antigen receptor (CAR).

In a fourth further aspect the present invention provides a nucleic acid which encodes a fusion protein according to the first further aspect of the present invention or a truncated protein according to the second or third further aspects of the present invention.

In a fifth further aspect the present invention provides a nucleic acid construct which comprises a nucleic acid sequence encoding a fusion protein which comprises (i) a ZAP70 or PTPN6 SH2 domain; and (ii) a protease domain (e.g. a TeV domain) and a nucleic acid sequence encoding a membrane tethered transcription factor which comprises:
(i) a membrane tether;
(ii) a protease recognition site; and
(iii) a transcription factor.

In a sixth further aspect the present invention provides a nucleic acid construct which comprises
(a) a nucleic acid sequence encoding a fusion protein according to the first further aspect of the present invention which comprises a PTPN6 SH2 domain, or a truncated protein according to the third further aspect of the present invention; and
(b) a nucleic acid sequence encoding a receptor comprising an ITIM containing endodomain.

In a seventh further aspect the present invention provides a nucleic acid construct which comprises a nucleic acid sequence encoding a fusion protein which comprises (i) a ZAP70 or PTPN6 SH2 domain; and (ii) a protease domain (e.g. a TeV domain) and a nucleic acid sequence encoding a receptor which comprises a protease cleavage site.

In an eighth further aspect the present invention provides a nucleic acid construct which comprises:
(a) a nucleic acid sequence encoding a fusion protein which comprises (i) a PTPN6 SH2 domain; and (ii) a protease domain (e.g. a TeV domain);
(b) a nucleic acid sequence encoding a receptor which comprises a protease cleavage site; and
(c) a nucleic acid sequence encoding a receptor comprising an ITIM containing endodomain.

The receptor may be a T-cell receptor (TCR) or a chimeric antigen receptor (CAR).

Suitably, in the nucleic acid construct according to the eighth aspect of the present invention, the nucleic acid sequence (b) may be a T-cell receptor (TCR) or a chimeric antigen receptor (CAR) which comprises:
(i) a protease cleavage site between a transmembrane domain and an activating endodomain; or
(ii) an activating endodomain fused to an inhibitory endodomain via a protease cleavage site.

In a ninth further aspect the present invention provides a vector comprising a nucleic acid according to the fourth further aspect of the present invention or a nucleic acid construct according to any of fifth to the ninth further aspects of the present invention.

The vector may be a retroviral vector or a lentiviral vector.

In a tenth further aspect the present invention provides a cell comprising a fusion protein according to the first further aspect of the present invention or a truncated protein according to the second or third further aspects of the present invention.

In an eleventh further aspect the present invention provides a cell which comprises (a) a fusion protein according to the first further aspect of the present invention which comprises a PTPN6 SH2 domain, or a truncated protein according to the third further aspect of the present invention; and (b) a receptor comprising an ITIM containing endodomain.

The cell may be an immune cell, such as a T cell or a natural killer (NK) cell.

In a twelfth further aspect the present invention provides a cell which comprises a fusion protein which comprises (i) a ZAP70 or PTPN6 SH2 domain; and (ii) a protease domain (e.g. a TeV domain) and a receptor which comprises a protease cleavage site.

In a thirteenth further aspect the present invention provides a cell which comprises:
(a) a fusion protein which comprises (i) a PTPN6 SH2 domain; and (ii) a protease domain (e.g. a TeV domain);
(b) a receptor which comprises a protease cleavage site; and
(c) a receptor comprising an ITIM containing endodomain.

The receptor may be a T-cell receptor (TCR) or a chimeric antigen receptor (CAR).

The receptor (b) may be a T-cell receptor (TCR) or a chimeric antigen receptor (CAR) which comprises:
 (i) a protease cleavage site between a transmembrane domain and an activating endodomain; or
 (ii) an activating endodomain fused to an inhibitory endodomain via a protease cleavage site.

In a fourteenth further aspect the present invention provides a cell which comprises a nucleic acid according to the fourth further aspect of the present invention or a nucleic acid construct according to any of the fifth to the ninth further aspects of the present invention.

In a fifteenth further aspect the present invention provides a pharmaceutical composition comprising a plurality of cells according to any of the tenth to the fourteenth further aspects of the present invention.

In a sixteenth further aspect the present invention provides a pharmaceutical composition according to the fifteenth further aspect of the present invention for use in treating and/or preventing a disease.

In a seventeenth further aspect the present invention relates to a method for treating and/or preventing a disease, which comprises the step of administering a pharmaceutical composition according the fifteenth further aspect to a subject.

The method may comprise the following steps:
 (i) isolation of a T cell or NK cell containing sample from a subject;
 (ii) transduction or transfection of the T cells or NK cells with a nucleic acid according to any of the fourth to the ninth further aspects of the present invention or a vector according to the tenth further aspect of the present invention; and
 (iii) administering the T cells or NK cells from (ii) to the subject.

In an eighteenth further aspect the present invention relates to the use of a pharmaceutical composition according to the fifteenth further aspect of the present invention in the manufacture of a medicament for the treatment and/or prevention of a disease.

The disease may be cancer.

In a nineteenth further aspect the present invention provides a kit which comprises a nucleic acid according to the fourth further aspect of the present invention or a nucleic acid construct according to any of the fifth to the eighth further aspects of the present invention or a vector according to the ninth further aspect of the present invention.

In a twentieth further aspect the present invention relates to a kit which comprises a cell according to any of the tenth to the fourteenth further aspects of the present invention.

In a twenty-first further aspect the present invention relates to a method for making a cell according to any of the tenth to the fourteenth further aspects of the present invention, which comprises the step of introducing: a nucleic acid sequence according to any of the fourth to the eighth further aspects of the present invention or the vector according to the ninth further aspect of the present invention, into the cell.

The cell may be from a sample isolated from a subject.

Yet further aspect of the invention are summarised in the following paragraphs:

A1. A truncated protein which comprises an SH2 domain from a protein which binds a phosphorylated immunoreceptor tyrosine-based activation motif (ITAM) but lacks a kinase domain.

A2. A truncated protein according to paragraph A1, which comprises the ZAP70 SH2 domain but lacks the ZAP70 kinase domain.

B1. A truncated protein which comprises an SH2 domain from a protein which binds a phosphorylated immunoreceptor tyrosine-based inhibition motif (ITIM) but lacks a phosphatase domain.

B2. A truncated protein according to paragraph 131, which comprises the PTPN6 SH2 domain but lacks the PTPN6 phosphatase domain.

B3. A truncated protein according to paragraph 131, which comprises the SHP-2 SH2 domain but lacks the SHP-2 phosphatase domain.

C1. A fusion protein which comprises (i) an SH2 domain from a protein which binds a phosphorylated immunoreceptor tyrosine-based activation motif (ITAM); and (ii) a phosphatase domain.

C2. A fusion protein according to paragraph C1, which comprises a ZAP70 SH2 domain.

C3. A fusion protein according to paragraph C1 or C2, which comprises a PTPN6 or SHP-2 phosphatase domain.

D1. A fusion protein which comprises (i) an SH2 domain from a protein which binds a phosphorylated immunoreceptor tyrosine-based inhibition motif (ITIM); and (ii) a kinase domain.

D2. A fusion protein according to paragraph D1, which comprises an SH2 domain from PTPN6 or SHP-2.

D3. A fusion protein according to paragraph D1 or D2, which comprises a Zap70 kinase domain D4. A fusion protein according to paragraph D1 or D2, which comprises an AKT or JAK kinase domain.

E1. A fusion protein which comprises (i) an SH2 domain from a protein which binds a phosphorylated immunoreceptor tyrosine-based activation motif (ITAM) or from a protein which binds a phosphorylated immunoreceptor tyrosine-based inhibition motif (ITIM); and (ii) a heterologous signalling domain.

E2. A fusion protein according to paragraph E1, which comprises an SH2 domain from ZAP70, PTPN6 or SHP-2.

E3. A fusion protein according to paragraph E1 or E2, wherein the heterologous signalling domain is from a signalling molecule which is not usually activated by an ITAM or ITIM containing receptor.

E4. A fusion protein according to paragraph E1, E2 or E3, wherein the heterologous signalling domain is a co-stimulatory domain.

E5. A fusion protein according to paragraph E4 which comprises a CD28, OX40 or 41 BB co-stimulatory domain.

E6. A fusion protein according to paragraph E1, E2 or E3, wherein the co-stimulatory domain is an inhibitory domain.

E7. A fusion protein according to paragraph E6, wherein the inhibitory domain comprises the endodomain of CD148 or CD45.

E8. A fusion protein according to paragraph E6, wherein the heterologous signalling domain is or comprises the endodomain of ICOS, CD27, BTLA, CD30, GITR or HVEM.

F1. A fusion protein which comprises (i) an SH2 domain from a protein which binds a phosphorylated immunoreceptor tyrosine-based activation motif (ITAM); and (ii) an ITAM-containing domain.

F2. A fusion protein according to paragraph F1, which comprises a ZAP70 SH2 domain.

F3. A fusion protein according to paragraph F1 or F2, wherein the ITAM-containing domain is or comprises the endodomain of CD3-Zeta.

G1. A fusion protein which comprises (i) an SH2 domain from a protein which binds a phosphorylated immunoreceptor tyrosine-based inhibition motif (ITIM); and (ii) an ITIM-containing domain.

G2. A fusion protein according to paragraph G1, which comprises an SH2 domain from PTPN6 or SHP-2.

G3. A fusion protein according to paragraph G1 or G2, wherein the ITIM-containing domain is or comprises the endodomain from PD1, PDCD1, BTLA4, LILRB1, LAIR1, CTLA4, KIR2DL1, KIR2DL4, KIR2DL5, KIR3DL1 or KIR3DL3.

H1. A fusion protein which comprises (i) an SH2 domain from a protein which binds a phosphorylated immunoreceptor tyrosine-based inhibition motif (ITIM) or from a protein which binds a phosphorylated immunoreceptor tyrosine-based inhibition motif (ITIM); and (ii) a protease domain.

H2. A fusion protein according to paragraph H1, which comprises an SH2 domain from ZAP70, PTPN6 or SHP-2.

H3. A fusion protein according to paragraph H1 or H2, wherein the protease domain is or comprises Tobacco Etch Virus Protease (TeV).

I1. A nucleic acid sequence which encodes a truncated protein according to any of paragraphs A or B, or a fusion protein according to any of paragraphs C, D, E, F, G or H.

J1. A nucleic acid construct which comprises a nucleic acid sequence according to paragraph I and a nucleic acid sequence encoding a chimeric antigen receptor J2. A nucleic acid construct which comprises a nucleic acid sequence according to paragraph I and a nucleic acid sequence encoding a membrane-tethered transcription factor having a protease cleavage site.

J3. A nucleic acid construct which comprises a nucleic acid sequence according to paragraph I and a nucleic acid sequence encoding a target CAR which comprises an intracellular protease cleavage site.

K1. A vector comprising a nucleic acid sequence according to paragraph I or a nucleic acid construct according to paragraphs J.

L1. A cell which comprises a truncated protein according to any of paragraphs A or B, or a fusion protein according to any of paragraphs C, D, E, F, G or H.

M1. A cell which comprises a fusion protein according to any of paragraphs H and a membrane-tethered transcription factor with a protease cleavage site.

M2. A cell according to paragraph M1, wherein cleavage at the protease cleavage site releases the transcription factor leading to increased expression of a target gene.

M3. A cell according to paragraph M2, wherein the target gene encodes a cytokine.

M4. A cell according to paragraph M3, wherein the cytokine is selected from the following group: IL-2, IL-7, IL-15 and IL-12.

M5. A cell which comprises a fusion protein according to any of paragraphs H and a target receptor (CAR) which comprises an intracellular protease cleavage site.

M6. A cell according to claim M5, wherein the target CAR comprises an activatory or co-stimulatory endodomain and cleavage at the protease cleavage site removes the endodomain from the target CAR.

M7. A cell according to claim M5, wherein the target CAR comprises an inhibitory endodomain and cleavage at the protease cleavage site removes the inhibitory endodomain from the target CAR.

M8. A cell according to paragraph M7, wherein the inhibitory endodomain comprises a CD148 or CD45 endodomain.

M9. A cell which comprises a fusion protein according to any of paragraphs H and two CARs: an activating CAR comprising an ITAM-containing endodomain; and a target CAR as defined in any of paragraphs M5 to M8.

M10. A cell which comprises a fusion protein according to any of paragraphs H and two CARs: an inhibitory CAR comprising an ITIM-containing endodomain; and a target CAR as defined in any of paragraphs M5 to M8.

The aspects of the present invention described above enable T cell signalling pathways to be modulated and altered by, for example, the mechanisms described in Table 1.

TABLE 1

| Application of signal modulation | | |
| --- | --- | --- |
| Type | Mechanism | Application |
| Blocking signal | ZAP70, SHP-2 or PTPN6 are truncated - keeping SH2 domain alone | Truncated ZAP70, SHP-2 or PTPN6 competes with wild-type full-length ZAP70, SHP-2 or PTPN6. Since this does not signal, it will inhibit activation. Applications include, for example, with ZAP70 when a very strong activation signal is deleterious, or with PTPN6 or SHP-2 when the effect of an inhibitory signal e.g. PD1/PDL1 needs to be reduced. |
| Crosswire signal | ZAP70 SH2 fused to PTPN6/SHP-2 phosphatase, or PTPN6/SHP-2 SH2 fused to ZAP70 kinase for instance. | In this embodiment, a ZAP70 SH2 is fused to the phosphatase from PTPN6/SHP-2, or the other way round, i.e. the PTPN6/SHP-2 SH2 domain is fused with the ZAP70 kinase domain. When the T-cell receives an inhibitory signal, it interprets it as an excitatory signal or vice versa. |

TABLE 1-continued

Application of signal modulation

| Type | Mechanism | Application |
| --- | --- | --- |
| Amplified signal | ZAP70 fused to further ITAM domains or PTPN6/SHP-2 fused to further ITIM domains. | A single phospho-ITAM or ITIM leads to a concatenation of ITAMs or ITIMs leading to augmented signal or increased sensitivity to antigen. |
| Bypass signal | ZAP70 SH2 or PTPN6/SHP-2 SH2 fused with e.g. CD28, 41BB endodomains or AKT kinase domain, a JAK kinase domain etc. | In this embodiment, a "non-physiological" signal can be attached to the ITAM/ITM pathway. In this way an ITAM/ITIM signal can lead to a co-stimulatory signal, or a signal such as AKT or a cytokine type signal |
| Transcriptional signal | ZAP70 SH2 or PTPN6/SHP-2 SH2 fused to protease domain along with co-expression of a membrane tethered transcription factor with a liberating protease cleavage site | In this embodiment, a transcriptional signal is transmitted upon immune receptor activation or inhibition. Such a signal can, for example, result in the expression of a particular cytokine upon T-cell activation or inhibition. |
| Castration signal | ZAP70 SH2 domain or PTPN6/SHP-2 SH2 domain fused to a protease domain; a reciprocal receptor has a protease cleavage site | In this embodiment, activation or inhibition of a receptor results in inhibition or activation of another receptor |

DESCRIPTION OF THE FIGURES

FIG. 2—Diagram of a blocking signal system—a) A truncated ZAP70 which does not comprise a kinase domain is over-expressed. Consequently, it competes with full-length ZAP70 for ITAMs and reduces ITAM signalling. (b) A truncated PTPN6 which does not comprise a phosphatase domain is over-expressed, competing for full-length PTPN6 reducing ITIM signalling.

FIG. 4—Diagram of an amplified signal system: (a) full-length ZAP70 has a CD3 Zeta endodomain attached to its amino terminus so a cascade of ITAMs assembles. (b) full-length PTPN6 has PD1 endodomain attached to its amino terminus so a cascade of ITIMs assembles.

FIG. 5—Diagram of examples of a bypass signal system: (a) ZAP70 fused with CD28 endodomain; (b) ZAP70 fused with 41BB endodomain; (c) ZAP70 fused with AKT kinase; (d) PTPN6 SH2 domain is fused with 41 BB endodomain FIG. 6—Diagram of an illustrative transcriptional signal system: a) A ZAP-TeV fusion is co-expressed with a membrane-tethered transcription factor which can be released from the membrane by cleavage of its TeV recognition motif. This is shown co-expressed with a CD19 CAR. Hence, upon recognition of CD19 on a target cell, the T-cell becomes activated and in addition, the transcription factor becomes active. (b) An alternative system using a PTPN6-TeV fusion instead. Here the CAR consists of an ITIM-bearing endodomain. Hence, upon recognition of CD19 by the CAR, the transcription factor becomes active but this is independent of T-cell activation.

FIG. 7—Diagram of a castration signal system: two CARs are shown—one which recognizes CD19 and is activating and one which recognizes CD33 and is inhibiting—these specificities are for illustration only (a) AND NOT signal castration; here an SH2-Tev fusion protein is recruited to activated ITIM CAR upon its activation. This results in cleavage of ITAMs from an activating CAR which is constructed such that a TeV cleavage site connects the transmembrane-domain to the ITAM domain. Hence, the activating CAR is inhibited. (b) AND signal castration: Here, an SH2-Tev fusion protein is recruited to an ITIM CAR upon its activation. This results in release of a phosphatase domain from an activating CAR which is constructed so that a phosphatase is connected to its carboxy-terminus via a TeV cleavage domain. This results in release of constitutive inhibition, allowing the CAR to activate in the presence of cognate antigen.

FIG. 10—(a) Phospho-AKT blot of T-cells activated with increasing amounts of OKT3. (b) Microscopy of ZAP-AKT or control T-cells unstimulated, stimulated with just OKT3 or stimulated with both OKT3 and IL-2. ZAP-AKT T-cells stimulated with just OKT3 resemble non-transduced T-cells stimulated with both OKT3 and IL2.

FIG. 11—(a) Implementation of direct TeV transcriptional switch. A CD19 CAR's endodomain is replaced with the TeV protease. A membrane tethered VP16/GAL4 transcription factor is also co-expressed. A Luciferase reporter detects VP16/GAL5 activity. (b) Implementation with ZAP-TeV. A standard CD19 CAR is co-expressed with ZAP-TeV fusion along with the membrane tethered transcription factor.

FIG. 14—Illustrative protein sequences of the present invention

FIG. 15—PD-1 signal blockade using truncated SHP-1 (PTPN6) or truncated SHP-2 PBMC cells were cotransduced with PD1 and either CAR alone (FMC63); or a bicistronic construct containing CAR and truncated SHP-1, or CAR and truncated SHP-2. These cells were co-cultured for 48 hours with SupT1 cells transduced with CD19, PDL1 or both and IFNγ release measured by ELISA.

DETAILED DESCRIPTION

Protein

The present invention provides a truncated protein which comprises an SH2 domain.

The present invention also provides a fusion protein comprising (i) an SH2 domain; and (ii) a heterologous domain.

The SH2 domain may be from a protein which binds a phosphorylated immunoreceptor tyrosine-based activation motif (ITAM) or from a protein which binds a phosphorylated immunoreceptor tyrosine-based inhibition motif (ITIM).

An example of a protein which binds an ITAM is ZAP70. Examples of proteins which bind ITIMs include PTPN6 and SHP-2

The fusion protein of the invention therefore comprises an SH2 domain and at least one further domain which is not present in a wild-type protein from which the SH2 domain was derived.

SRC Homology 2 (SH2) Domain

Intracellular signalling pathways are initiated and controlled by the reversible post-translational modification of proteins including phosphorylation, ubiquitinylation and acetylation.

SH2 domains are modular protein domains that serve as adaptors and mediate protein-protein interactions by binding to phosphorylated peptides in their respective protein binding partners, often cell surface receptors. SH2 domains typically bind a phosphorylated tyrosine residue in the context of a longer peptide motif within a target protein, and SH2 domains represent the largest class of known pTyr-recognition domains Although SH2 domains lack any intrinsic catalytic activity they are frequently coupled to independent catalytic domains and thus, in response to a specific input signal, serve to localize these catalytic domains so particular subcellular locations or to the vicinity of appropriate substrates, activators or inhibitors. In addition SH2 domains can also be found linked to adaptor protein domains and so can serve in the formation of large multi-protein complexes.

Zeta-Chain-Associated Protein Kinase 70 (ZAP70)

ZAP70 is a protein normally expressed near the surface membrane of T cells and natural killer cells. It is part of the T cell receptor (TCR), and plays a critical role in T-cell signalling. Its molecular weight is 70 kDa, and is composed of 2 N-terminal SH2 domains and a C-terminal kinase domain. It is a member of the protein-tyrosine kinase family.

Figure 1:
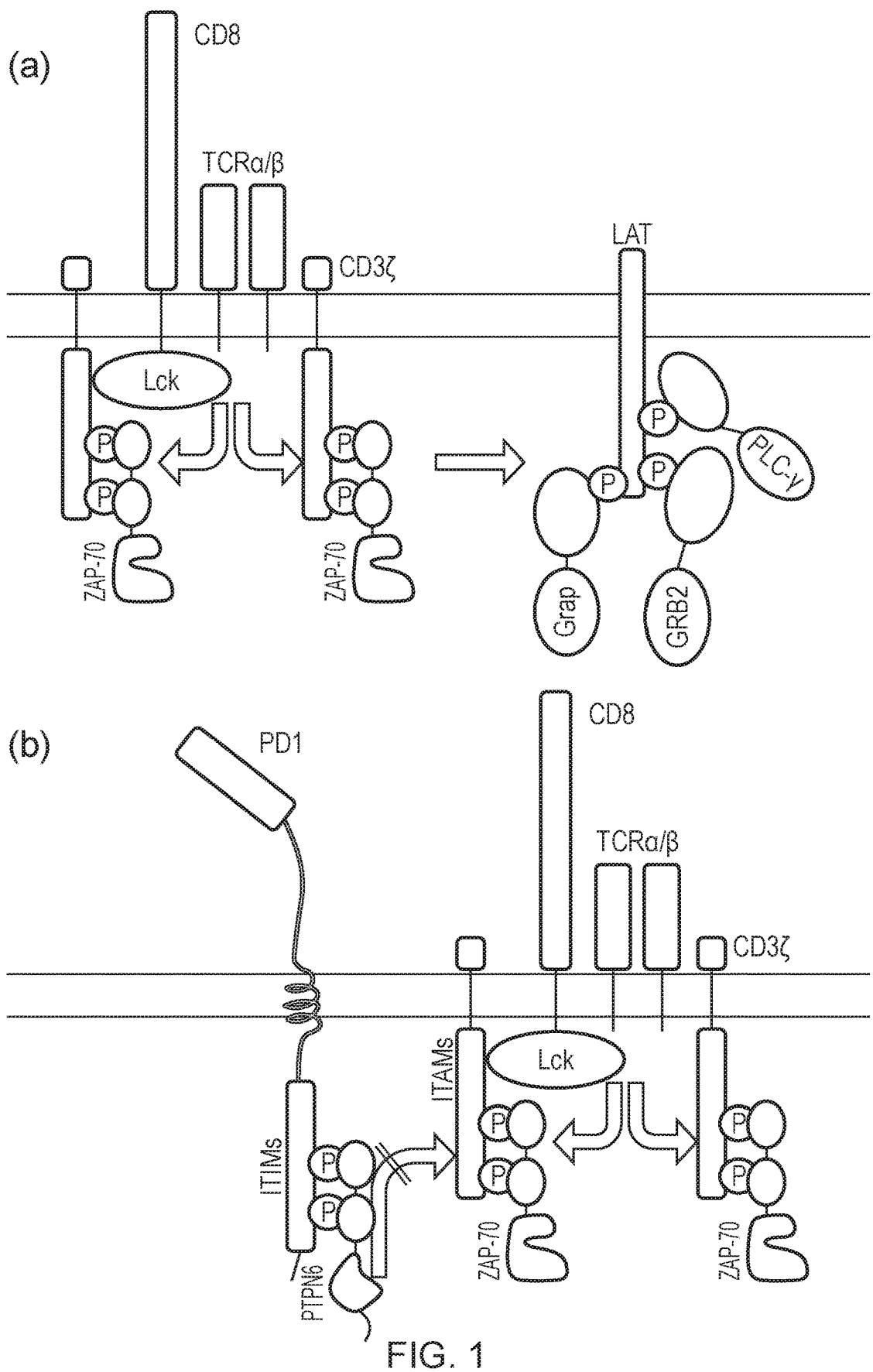
FIG. 1 (a)—Diagram of immediate T-cell activation pathways. T-cell receptor activation results in phosphorylation of ITAMs. Phosphorylated ITAMs are recognized by the ZAP70 SH2 domains. Upon recognition, ZAP70 is recruited to the juxta-membrane region and its kinase domain subsequently phosphorylates LAT. Phosphorylated LAT is subsequently recognized by the SH2 domains of GRAP, GRB2 and PLC-γ. (b)—Diagram of immediate T-cell inhibition pathways. Activation of an inhibitory immune-receptor such as PD1 results in phosphorylation of ITIM domains. These are recognized by the SH2 domains of PTPN6. Upon recognition, PTPN6 is recruited to the juxta-membrane region and its phosphatase domain subsequently de-phosphorylates ITAM domains inhibiting immune activation.
Figure 3:
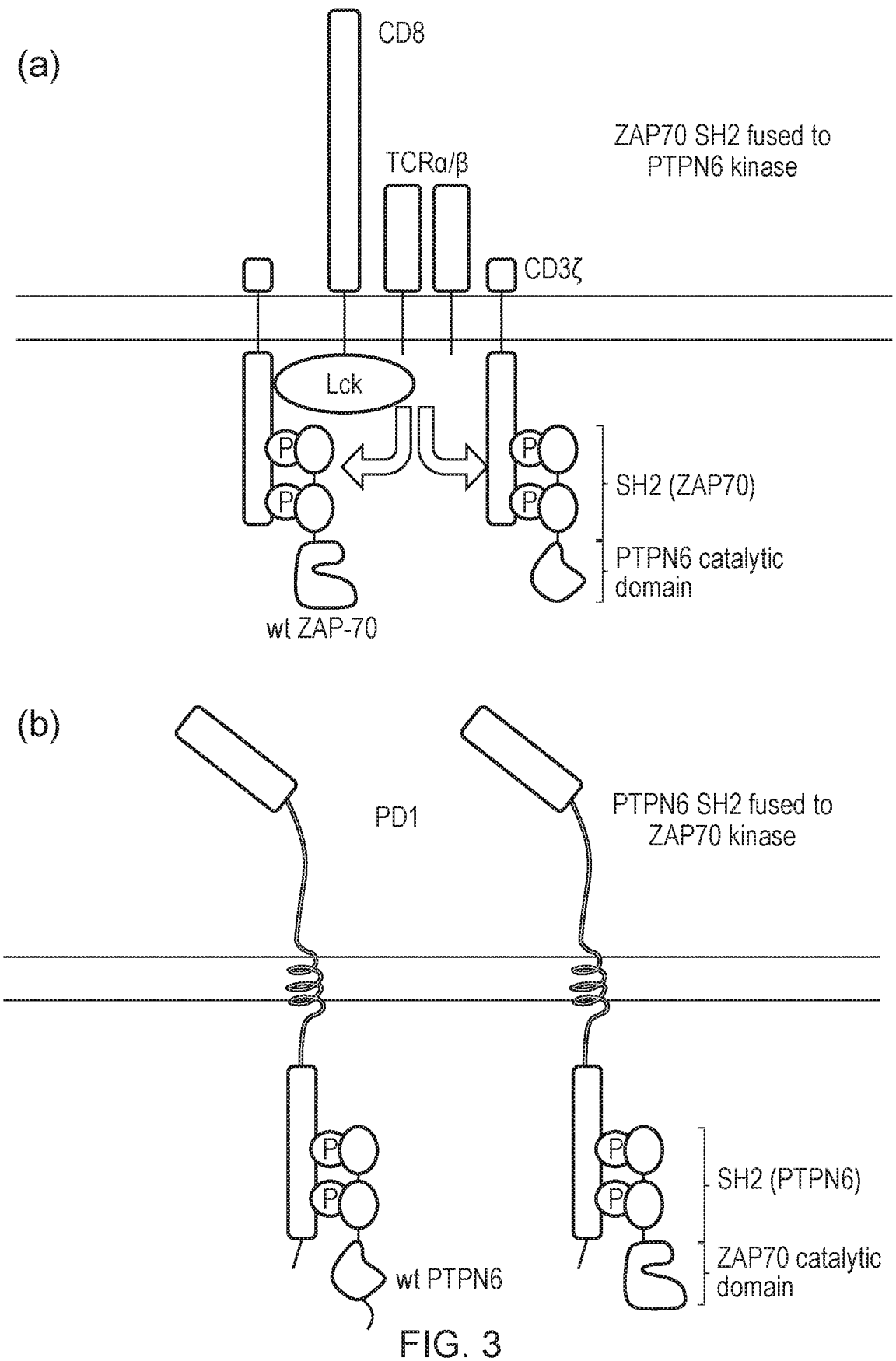
FIG. 3—Diagram of a crosswire signal system: (a) ZAP70 SH2 is fused to PTPN6 phosphatase, hence acts to dampen ITAM phosphorylation; (b) PTPN6 SH2 is fused to ZAP70 kinase resulting in paradoxical activation in response to an inhibitory signal.
Figure 6:
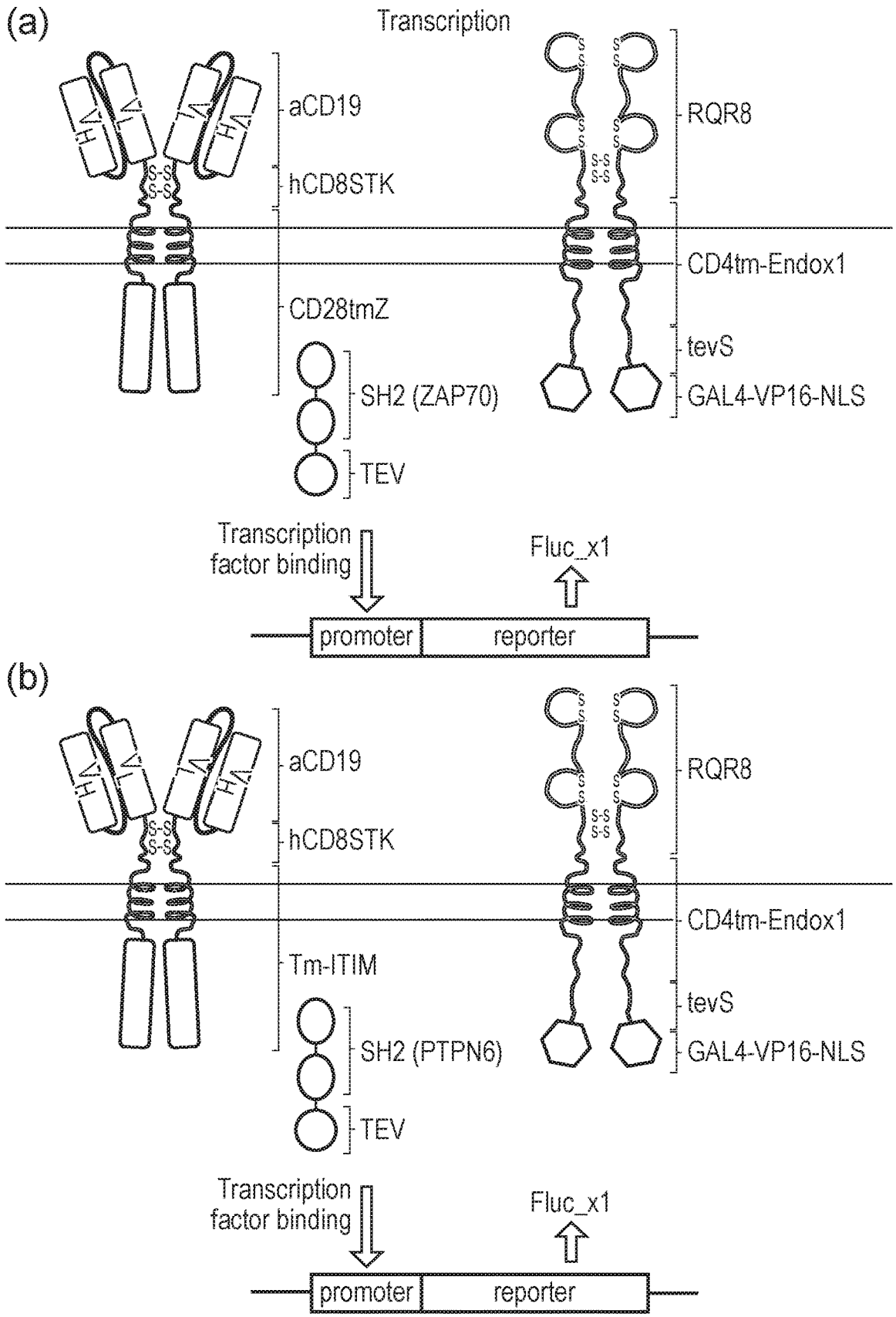

The earliest step in T cell activation is the recognition of a peptide MHC-complex on the target cell by the TCR. This initial event causes the close association of Lck kinase with the cytoplasmic tail of CD3-zeta in the TCR complex. Lck then phosphorylates tyrosine residues in the cytoplasmic tail of CD3-zeta which allows the recruitment of ZAP70. ZAP70 is an SH2 containing kinase that plays a pivotal role in T cell activation following engagement of the TCR. Tandem SH2 domains in ZAP70 bind to the phosphorylated CD3 resulting in ZAP70 being phosphorylated and activated by Lck or by other ZAP70 molecules in trans. Active ZAP70 is then able to phosphorylate downstream membrane proteins, key among them the linker of activated T cells (LAT) protein. LAT is a scaffold protein and its phosphorylation on multiple residues allows it to interact with several other SH2 domain-containing proteins including Grb2, PLC-g and Grap which recognize the phosphorylated peptides in LAT and transmit the T cell activation signal downstream ultimately resulting in a range of T cell responses. This process is summarized in FIG. 1.

Human ZAP70 protein has the UniProtKB accession number P43403. This sequence is 619 amino acids in length and is shown as SEQ ID NO: 1.

```
ZAP70 amino acid sequence
                                              (SEQ ID NO: 1)
MPDPAAHLPFFYGSISRAEAEEHLKLAGMADGLFLLRQCLRSLGGYVLSL

VHDVRFHHFPIERQLNGTYAIAGGKAHCGPAELCEFYSRDPDGLPCNLRK

PCNRPSGLEPQPGVFDCLRDAMVRDYVRQTWKLEGEALEQAIISQAPQVE

KLIATTAHERMPWYHSSLTREEAERKLYSGAQTDGKFLLRPRKEQGTYAL

SLIYGKTVYHYLISQDKAGKYCIPEGTKFDTLWQLVEYLKLKADGLIYCL
```

-continued

KEACPNSSASNASGAAAPTLPAHPSTLTHPQRRIDTLNSDGYTPEPARIT

SPDKPRPMPMDTSVYESPYSDPEELKDKKLFLKRDNLLIADIELGCGNFG

SVRQGVYRMRKKQIDVAIKVLKQGTEKADTEEMMREAQIMHQLDNPYIVR

LIGVCQAEALMLVMEMAGGGPLHKFLVGKREEIPVSNVAELLHQVSMGMK

YLEEKNFVHRDLAARNVLLVNRHYAKISDFGLSKALGADDSYYTARSAGK

WPLKWYAPECINFRKFSSRSDVWSYGVTMWEALSYGQKPYKKMKGPEVMA

FIEQGKRMECPPECPPELYALMSDCWIYKWEDRPDFLTVEQRMRACYYSL

ASKVEGPPGSTQKAEAACA

The fusion protein of the invention may comprise a ZAP70 SH2 domain. The truncated protein of the invention may comprise or consist of a ZAP70 SH2 domain. In this respect, the fusion or truncated protein may comprise or consist of the sequence shown as SEQ ID NO: 2.

ZAP70 complete SH2 domain
(SEQ ID NO: 2)
MPDPAAHLPFFYGSISRAEAEEHLKLAGMADGLFLLRQCLRSLGGYVLSL

VHDVRFHHFPIERQLNGTYAIAGGKAHCGPAELCEFYSRDPDGLPCNLRK

PCNRPSGLEPQPGVFDCLRDAMVRDYVRQTWKLEGEALEQAIISQAPQVE

KLIATTAHERMPWYHSSLTREEAERKLYSGAQTDGKFLLRPRKEQGTYAL

SLIYGKTVYHYLISQDKAGKYCIPEGTKFDTLWQLVEYLKLKADGLIYCL

KEACPNSSASNASGAAAPTLPAHPSTLTHP

ZAP70 has two SH2 domains at the N-terminal end of the sequence, at residues 10-102 and 163-254 of the sequence shown as SEQ ID No. 1. The truncated protein or fusion protein of the invention may therefor comprise one or both of the sequences shown as SEQ ID No. 3 and 4.

ZAP70 SH2 1
(SEQ ID NO: 3)
FFYGSISRAEAEEHLKLAGMADGLFLLRQCLRSLGGYVLSLVHDVRFHHF

PIERQLNGTYAIAGGKAHCGPAELCEFYSRDPDGLPCNLRKPC

ZAP70 SH2 2
(SEQ ID NO: 4)
WYHSSLTREEAERKLYSGAQTDGKFLLRPRKEQGTYALSLIYGKTVYHYL

ISQDKAGKYCIPEGTKFDTLWQLVEYLKLKADGLIYCLKEAC

The fusion protein may comprise a variant of SEQ ID NO: 2, 3 or 4 having at least 80, 85, 90, 95, 98 or 99% sequence identity, provided that the variant sequence is a SH2 domain sequence has the required properties. In other words, the variant sequence should be capable of binding to the phosphorylated tyrosine residues in the cytoplasmic tail of CD3-zeta which allow the recruitment of ZAP70.

Methods of sequence alignment are well known in the art and are accomplished using suitable alignment programs. The % sequence identity refers to the percentage of amino acid or nucleotide residues that are identical in the two sequences when they are optimally aligned. Nucleotide and protein sequence homology or identity may be determined using standard algorithms such as a BLAST program (Basic Local Alignment Search Tool at the National Center for Biotechnology Information) using default parameters, which is publicly available at http://blast.ncbi.nlm.nih.gov. Other algorithms for determining sequence identity or homology include: LALIGN (http://www.ebi.ac.ukfTools/psadalign/and http://www.ebi.ac.uk/Tools/psadalign/nucleotide.html), AMAS (Analysis of Multiply Aligned Sequences, at http://www.compbio.dundee.ac.uk/Software/Amas/amas.html), FASTA (http://www.ebi.ac.ukfTools/sss/fasta/), Clustal Omega (http://www.ebi.ac.ukfTools/msa/clustalo/), SIM (http://web.expasy.org/sim/), and EMBOSS Needle (http://www.ebi.ac.uk/Tools/psa/emboss needle/nucleotide-.html).

In certain embodiments, the fusion protein may comprise the ZAP70 SH2 domain and the ZAP70 kinase domain. For example, the fusion protein may comprise the sequence shown as SEQ ID NO: 1 or a variant thereof having at least 80, 85, 90, 95, 98 or 99% sequence identity.

Tyrosine-Protein Phosphatase Non-Receptor Type 6 (PTPN6)

PTPN6 is also known as Src homology region 2 domain-containing phosphatase-1 (SHP-1). It is a member of the protein tyrosine phosphatase family.

The N-terminal region of PTPN6 contains two tandem SH2 domains which mediate the interaction of PTPN6 and its substrates. The C-terminal region contains a tyrosine-protein phosphatase domain.

PTPN6 is capable of binding to, and propagating signals from, a number of inhibitory immune receptors or ITIM containing receptors. Examples of such receptors include, but are not limited to, PD1, PDCD1, BTLA4, LILRB1, LAIR1, CTLA4, KIR2DL1, KIR2DL4, KIR2DL5, KIR3DL1 and KIR3DL3.

Human PTPN6 protein has the UniProtKB accession number P29350. This sequence is 595 amino acids in length and is shown as SEQ ID NO: 5.

PTPN6 amino acid sequence
(SEQ ID NO: 5)
MVRWFHRDLSGLDAETLLKGRGVHGSFLARPSRKNQGDFSLSVRVGDQVT

HIRIQNSGDFYDLYGGEKFATLTELVEYYTQQQGVLQDRDGTIIHLKYPL

NCSDPTSERWYHGHMSGGQAETLLQAKGEPWTFLVRESLSQPGDFVLSVL

SDQPKAGPGSPLRVTHIKVMCEGGRYTVGGLETFDSLTDLVEHFKKTGIE

EASGAFVYLRQPYYATRVNAADIENRVLELNKKQESEDTAKAGFWEEFES

LQKQEVKNLHQRLEGQRPENKGKNRYKNILPFDHSRVILQGRDSNIPGSD

YINANYIKNQLLGPDENAKTYIASQGCLEATVNDFWQMAWQENSRVIVMT

TREVEKGRNKCVPYWPEVGMQRAYGPYSVTNCGEHDTTEYKLRTLQVSPL

DNGDLIREIWHYQYLSWPDHGVPSEPGGVLSFLDQINQRQESLPHAGPII

VHCSAGIGRTGTIIVIDMLMENISTKGLDCDIDIQKTIQMVRAQRSGMVQ

TEAQYKFIYVAIAQFIETTKKKLEVLQSQKGQESEYGNITYPPAMKNAHA

KASRTSSKHKEDVYENLHTKNKREEKVKKQRSADKEKSKGSLKRK

The fusion protein of the invention may comprise a PTPN6 SH2 domain. The truncated protein of the invention may comprise or consist of a PTPN6 SH2 domain. In this respect, the fusion or truncated protein may comprise or consist of the sequence shown as SEQ ID NO: 6.

PTPN6 SH2 complete domain
(SEQ ID NO: 6)
MVRWFHRDLSGLDAETLLKGRGVHGSFLARPSRKNQGDFSLSVRVGDQVT

HIRIQNSGDFYDLYGGEKFATLTELVEYYTQQQGVLQDRDGTIIHLKYPL

NCSDPTSERWYHGHMSGGQAETLLQAKGEPWTFLVRESLSQPGDFVLSVL

SDQPKAGPGSPLRVTHIKVMCEGGRYTVGGLETFDSLTDLVEHFKKTGIE

EASGAFVYLRQPYY

PTPN6 has two SH2 domains at the N-terminal end of the sequence, at residues 4-100 and 110-213 of the sequence shown as SEQ ID No. 5. The truncated protein or fusion protein of the invention may therefor comprise one or both of the sequences shown as SEQ ID No. 3 and 4.

PTPN6 SH2 1
(SEQ ID NO: 7)
WFHRDLSGLDAETLLKGRGVHGSFLARPSRKNQGDFSLSVRVGDQVTHIR

IQNSGDFYDLYGGEKFATLTELVEYYTQQQGVLQDRDGTIIHLKYPL

PTPN6 SH2 2
(SEQ ID No. 8)
WYHGHMSGGQAETLLQAKGEPWTFLVRESLSQPGDFVLSVLSDQPKAGPG

SPLRVTHIKVMCEGGRYTVGGLETFDSLTDLVEHFKKTGIEEASGAFVYL

RQPY

The fusion protein may comprise a variant of SEQ ID NO: 6, 7 or 8 having at least 80, 85, 90, 95, 98 or 99% sequence identity, provided that the variant sequence is a SH2 domain sequence has the required properties. In other words, the variant sequence should be capable of binding to the phosphorylated tyrosine residues in the cytoplasmic tail of at least one of PD1, PDCD1, BTLA4, LILRB1, LAIR1, CTLA4, KIR2DL1, KIR2DL4, KIR2DL5, KIR3DL1 or KIR3DL3 which allow the recruitment of PTPN6.

In certain embodiments, the fusion protein may comprise the PTPN6 SH2 domain and the PTPN6 phosphatase domain. For example, the fusion protein may comprise the sequence shown as SEQ ID NO: 5 or a variant thereof having at least 80, 85, 90, 95, 98 or 99% sequence identity.

SHP-2

SHP-2, also known as PTPN11, PTP-1D and PTP-2C is is a member of the protein tyrosine phosphatase (PTP) family. Like PTPN6, SHP-2 has a domain structure that consists of two tandem SH2 domains in its N-terminus followed by a protein tyrosine phosphatase (PTP) domain. In the inactive state, the N-terminal SH2 domain binds the PTP domain and blocks access of potential substrates to the active site. Thus, SHP-2 is auto-inhibited. Upon binding to target phospho-tyrosyl residues, the N-terminal SH2 domain is released from the PTP domain, catalytically activating the enzyme by relieving the auto-inhibition.

Human SHP-2 has the UniProtKB accession number P35235-1. This sequence is 597 amino acids in length and is shown as SEQ ID NO: 9.

SHP-2 amino acid sequence
(SEQ ID NO: 9)
MTSRRWFHPNITGVEAENLLLTRGVDGSFLARPSKSNPGDFTLSVRRNGA

VTHIKIQNTGDYYDLYGGEKFATLAELVQYYMEHHGQLKEKNGDVIELKY

PLNCADPTSERWFHGHLSGKEAEKLLTEKGKHGSFLVRESQSHPGDFVLS

VRTGDDKGESNDGKSKVTHVMIRCQELKYDVGGGERFDSLTDLVEHYKKN

PMVETLGTVLQLKQPLNTTRINAAEIESRVRELSKLAETTDKVKQGFWEE

FETLQQQECKLLYSRKEGQRQENKNKNRYKNILPFDHTRVVLHDGDPNEP

VSDYINANIIMPEFETKCNNSKPKKSYIATQGCLQNTVNDFWRMVFQENS

RVIVMTTKEVERGKSKCVKYWPDEYALKEYGVMRVRNVKESAAHDYTLRE

LKLSKVGQALLQGNTERTVWQYHFRTWPDHGVPSDPGGVLDFLEEVHHKQ

ESIVDAGPVVVHCSAGIGRTGTFIVIDILIDIIREKGVDCDIDVPKTIQM

VRSQRSGMVQTEAQYRFIYMAVQHYIETLQRRIEEEQKSKRKGHEYTNIK

YSLVDQTSGDQSPLPPCTPTPPCAEMREDSARVYENVGLMQQQRSFR

The fusion protein of the invention may comprise a SHP-2 SH2 domain. The truncated protein of the invention may comprise or consist of a SHP-2 SH2 domain. In this respect, the fusion or truncated protein may comprise or consist of the first SH2 domain of SHP-2, for example comprising amino acids 6-102 of SEQ ID NO. 9 or the second SH2 domain of SHP-2, for example comprising amino acids 112-216 of SHP-2. The fusion or truncated protein may comprise or consist of the sequence shown as SEQ ID NO: 10, 11 or 12.

SHP-2 first SH2 domain
(SEQ ID NO: 10)
WFHPNITGVEAENLLLTRGVDGSFLARPSKSNPGDFTLSVRRNGAVTHIK

IQNTGDYYDLYGGEKFATLAELVQYYMEHHGQLKEKNGDVIELKYPL

SHP-2 second SH2 domain
(SEQ ID No. 11)
WFHGHLSGKEAEKLLTEKGKHGSFLVRESQSHPGDFVLSVRTGDDKGESN

DGKSKVTHVMIRCQELKYDVGGGERFDSLTDLVEHYKKNPMVETLGTVLQ

LKQPL

SHP-2 both SH2 domains
(SEQ ID No. 12)
WFHPNITGVEAENLLLTRGVDGSFLARPSKSNPGDFTLSVRRNGAVTHIK

IQNTGDYYDLYGGEKFATLAELVQYYMEHHGQLKEKNGDVIELKYPLNCA

DPTSERWFHGHLSGKEAEKLLTEKGKHGSFLVRESQSHPGDFVLSVRTGD

DKGESNDGKSKVTHVMIRCQELKYDVGGGERFDSLTDLVEHYKKNPMVET

LGTVLQLKQPL

The fusion protein may comprise a variant of SEQ ID NO: 10, 11 or 12 having at least 80, 85, 90, 95, 98 or 99% sequence identity, provided that the variant sequence is a SH2 domain sequence capable of binding an ITIM-containing domain. For example, the variant sequence may be capable of binding to the phosphorylated tyrosine residues in the cytoplasmic tail of PD1, PDCD1, BTLA4, LILRB1, LAIR1, CTLA4, KIR2DL1, KIR2DL4, KIR2DL5, KIR3DL1 or KIR3DL3.

Heterologous Domain

As used herein, the term 'heterologous domain' refers to any protein domain which is not present in:
i) wild type ZAP70 (see SEQ ID NO: 1) for fusion proteins comprising a ZAP70 SH2 domain;
ii) wild type PTPN6 (see SEQ ID NO: 5) for fusion proteins comprising a PTPN6 SH2 domain; or
iii) wild-type SHP-2 (see SEQ ID No. 9) for fusion proteins comprising a SHP-2 SH2 domain.

The heterologous domain may be or be derivable from (e.g. part of) a different protein from ZAP70, SHP-2 or PTPN6.

Alternatively the fusion protein may comprise a fusion of ZAP70 SH2 domain and a domain from PTPN6, such as the PTPN6 kinase domain. By the same token the fusion protein may comprise a fusion of PTPN6 SH2 domain and a domain from ZAP70, such as the ZAP70 kinase domain.

Amplified Signal

The present invention provides a fusion protein which comprises: an SH2 domain from an ITAM-binding protein; and an ITAM-containing domain.

The present invention also provide a fusion protein which comprises: an SH2 domain from an ITIM-binding protein; and an ITIM-containing domain.

These "amplified" signalling molecules will amplify an excitatory or inhibitory signal inside an immune cell such as a T cell.

As shown in FIG. 4, the presence of such molecules will lead to a concatenation of either ITAMs or ITIMs leading to an augmented activatory or inhibitory signal, respectively.

Amplification of an activatory signal is useful in situations where it is desirable to increase the sensitivity of the immune cell (such as a CAR-T cell) to antigen. This may be the case when, for example, the target antigen is expressed at low levels on the target cells.

Amplification of an inhibitory systems in situations where it is desirable to reduce or prevent T cell activation. WO2015/075469 describes a panel of "logic gate" chimeric antigen receptor pairs which, when expressed by a cell, such as a T cell, are capable of detecting a particular pattern of expression of at least two target antigens A and B). The "AND NOT gate" described in this application comprises a pair of CARs such that the T cell triggers only when antigen A but not antigen B is present on the target cell. In this AND NOT gate, one CAR (recognising antigen A) has an activating endodomain comprising and ITAM, whereas the other CAR (recognising antigen B) has an inhibitory endodomain which may comprise an ITIM. In the presence of antigen A alone, the presence of unligated inhibitory CAR is insufficient to prevent T cell activation, so activation occurs. However, in the presence of both antigens, areas of membrane form with high concentrations of both activatory and inhibitory CARs. Since both endodomains are concentrated, T-cell activation is prevented or reduced.

Amplification of the inhibitory signal using an amplified signalling molecule of the present invention could be used in an AND gate to reduce or remove any residual signalling which occurs in the presence of both antigens i.e. from incomplete inhibition of the activatory CAR by the inhibitory CAR.

ITAM-Containing Domain

In one embodiment, the fusion protein comprises a ZAP70 SH2 domain and an immunoreceptor tyrosine-based activation motif (ITAM)-containing domain.

A fusion of full-length ZAP70 with an ITAM containing domain results in a structure which amplifies an activating immune signal. Here, the fusion protein is recruited to a phospho-ITAM immune-receptor endodomain. ZAP70 functions normally to propagate the signal but also provides another set of ITAMs which become phosphorylated and recruit more ZAP70. This may be useful to increase signal strength and may increase sensitivity to low-density antigens, for example. In some embodiments, the fusion may include only the ZAP70 SH2 domain with an ITAM containing endodomain (e.g. the fusion does not contain a ZAP70 kinase domain). In other embodiments, the ratio of ZAP70 catalytic domains (kinase domains) with ITAMs may be varied to affect the kinetics of activation in response to dynamics of the activating receptor interactions with cognate target.

An ITAM is a conserved sequence of four amino acids that is repeated twice in the cytoplasmic tails of certain cell surface proteins of the immune system. The motif contains a tyrosine separated from a leucine or isoleucine by any two other amino acids, giving the signature YxxL/I. Two of these signatures are typically separated by between 6 and 8 amino acids in the tail of the molecule (YxxL/Ix(6-8)YxxL/I).

ITAMs are important for signal transduction in immune cells. Hence, they are found in the tails of important cell signalling molecules such as the CD3 and ζ-chains of the T cell receptor complex, the CD79-alpha and -beta chains of the B cell receptor complex, and certain Fc receptors. The tyrosine residues within these motifs become phosphorylated following interaction of the receptor molecules with their ligands and form docking sites for other proteins involved in the signalling pathways of the cell.

Several proteins are known to contain endodomains with one or more ITAM motifs. Examples of such proteins include the CD3 epsilon chain, the CD3 gamma chain and the CD3 delta chain to name a few. The ITAM motif can be easily recognized as a tyrosine separated from a leucine or isoleucine by any two other amino acids, giving the signature YxxL/I. Typically, but not always, two of these motifs are separated by between 6 and 8 amino acids in the tail of the molecule (YxxL/Ix(6-8)YxxL/1). Hence, one skilled in the art can readily find existing proteins which contain one or more ITAM to transmit an activation signal. Further, given the motif is simple and a complex secondary structure is not required, one skilled in the art can design polypeptides containing artificial ITAMs to transmit an activation signal (see WO 2000063372, which relates to synthetic signalling molecules).

The ITAM-containing domain may be or comprise a CD3-zeta endodomain. Suitably, the ITAM-containing domain may comprise the sequence shown as SEQ ID NO: 13 or a variant thereof having at least 80, 85, 90, 95, 98 or 99% sequence identity which retains the capacity to be phosphorylated and recruit ZAP70.

(CD3-zeta endodomain)

SEQ ID NO: 13

RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

By way of example, the fusion protein may be or comprise the sequence shown as SEQ ID NO: 14, which contains a ZAP70-SH2 domain fused to a CD3-zeta endodomain.

SEQ ID NO: 14

MRRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATK

DTYDALHMQALPPRSGGGGSGGGGSGGGGSGGGGSMPDPAAHLPFFYGSI

SRAEAEEHLKLAGMADGLFLLRQCLRSLGGYVLSLVHDVRFHHFPIERQL

NGTYAIAGGKAHCGPAELCEFYSRDPDGLPCNLRKPCNRPSGLEPQPGVF

DCLRDAMVRDYVRQTWKLEGEALEQAIISQAPQVEKLIATTAHERMPWYH

SSLTREEAERKLYSGAQTDGKFLLRPRKEQGTYALSLIYGKTVYHYLISQ

DKAGKYCIPEGTKFDTLWQLVEYLKLKADGLIYCLKEACPNSSASNASGA

AAPTLPAHPSTLTHPQRRIDTLNSDGYTPEPARITSPDKPRPMPMDTSVY

-continued

ESPYSDPEELKDKKLFLKRDNLLIADIELGCGNFGSVRQGVYRMRKKQID

VAIKVLKQGTEKADTEEMMREAQIMHQLDNPYIVRLIGVCQAEALMLVME

MAGGGPLHKFLVGKREEIPVSNVAELLHQVSMGMKYLEEKNFVHRDLAAR

NVLLVNRHYAKISDFGLSKALGADDSYYTARSAGKWPLKWYAPECINFRK

FSSRSDVWSYGVTMWEALSYGQKPYKKMKGPEVMAFIEQGKRMECPPECP

PELYALMSDCWIYKWEDRPDFLTVEQRMRACYYSLASKVEGPPGSTQKAE

AACA

Suitably, the fusion protein may comprise the sequence shown as SEQ ID NO: 14 or a variant thereof having at least 80, 85, 90, 95, 98 or 99% sequence identity.

ITIM-Containing Domain

In one embodiment, the fusion protein comprises a PTPN6 SH2 domain and an immunoreceptor tyrosine-based inhibition motif (ITIM)-containing domain A fusion of full-length PTPN6 with an ITIM containing domain results in a structure which amplifies an inhibitory immune signal. Here, the fusion protein is recruited to a phospho-ITIM immune-receptor endodomain. PTPN6 functions normally to propagate the signal but also provides another set of ITIMs which become phosphorylated and recruit more PTPN6. In some embodiments, the fusion may include only the PTPN6 SH2 domain with an ITIM containing endodomain (e.g. the fusion does not contain a PTPN6 phosphatase domain). In other embodiments, the ratio of PTPN6 catalytic domains (phosphatase domains) with ITIMs may be varied to affect the kinetics of activation in response to dynamics of the inhibitory receptor interactions with cognate target.

An ITIM, is a conserved sequence of amino acids (S/I/V/LxYxxI/V/L) that is found in the cytoplasmic tails of many inhibitory receptors of the immune system. After ITIM-possessing inhibitory receptors interact with their ligand, their ITIM motif becomes phosphorylated by enzymes of the Src kinases, allowing them to recruit PTPN6 via interactions between the PTPN6 SH2 domain and the phosphorylated ITIM domains.

ITIM containing endodomains include those from CD22, LAIR-1, the Killer inhibitory receptor family (KIR), LILRB1, CTLA4, PD-1, BTLA, for example.

ITIM endodomains from PDCD1, BTLA4, LILRB1, LAIR1, CTLA4, KIR2DL1, KIR2DL4, KIR2DL5, KIR3DL1 and KIR3DL3 are shown in SEQ ID NO: 15 to 24 respectively PDCD1 endodomain
SEQ ID NO: 15
CSRAARGTIGARRTGQPLKEDPSAVPVFSVDYGELDFQWREKTPEPPVPC

VPEQTEYATIVFPSGMGTSSPARRGSADGPRSAQPLRPEDGHCSWPL

BTLA4
SEQ ID NO: 16
KLQRRWKRTQSQQGLQENSSGQSFFVRNKKVRRAPLSEGPHSLGCYNPMM

EDGISYTTLRFPEMNIPRTGDAESSEMQRPPPDCDDTVTYSALHKRQVGD

YENVIPDFPEDEGIHYSELIQFGVGERPQAQENVDYVILKH

LILRB1
SEQ ID NO: 17
LRHRRQGKHWTSTQRKADFQHPAGAVGPEPTDRGLQWRSSPAADAQEENL

YAAVKHTQPEDGVEMDTRSPHDEDPQAVTYAEVKHSRPRREMASPPSPLS

GEFLDTKDRQAEEDRQMDTEAAASEAPQDVTYAQLHSLTLRREATEPPPS

QEGPSPAVPSIYATLAIH

LAIR1
SEQ ID NO: 18
HRQNQIKQGPPRSKDEEQKPQQRPDLAVDVLERTADKATVNGLPEKDRET

DTSALAAGSSQEVTYAQLDHWALTQRTARAVSPQSTKPMAESITYAAVAR

H

CTLA4
SEQ ID NO: 19
FLLWILAAVSSGLFFYSFLLTAVSLSKMLKKRSPLTTGVYVKMPPTEPEC

EKQFQPYFIPIN

KIR2DL1
SEQ ID NO: 20
GNSRHLHVLIGTSVVIIPFAILLFFLLHRWCANKKNAVVMDQEPAGNRTV

NREDSDEQDPQEVTYTQLNHCVFTQRKITRPSQRPKTPPTDIIVYTELPN

AESRSKVVSCP

KIR2DL4
SEQ ID NO: 21
GIARHLHAVIRYSVAIILFTILPFFLLHRWCSKKKENAAVMNQEPAGHRT

VNREDSDEQDPQEVTYAQLDHCIFTQRKITGPSQRSKRPSTDTSVCIELP

NAEPRALSPAHEHHSQALMGSSRETTALSQTQLASSNVPAAGI

KIR2DL5
SEQ ID NO: 22
TGIRRHLHILIGTSVAIILFIILFFFLLHCCCSNKKNAAVMDQEPAGDRT

VNREDSDDQDPQEVTYAQLDHCVFTQTKITSPSQRPKTPPTDTTMYMELP

NAKPRSLSPAHKHHSQALRGSSRETTALSQNRVASSHVPAAGI

KIR3DL1
SEQ ID NO: 23
KDPRHLHILIGTSVVIILFILLLFFLLHLWCSNKKNAAVMDQEPAGNRTA

NSEDSDEQDPEEVTYAQLDHCVFTQRKITRPSQRPKTPPTDTILYTELPN

AKPRSKVVSCP

KIR3DL3
SEQ ID NO: 24
KDPGNSRHLHVLIGTSVVIIPFAILLFFLLHRWCANKKNAVVMDQEPAGN

RTVNREDSDEQDPQEVTYAQLNHCVFTQRKITRPSQRPKTPPTDTSV

The ITIM-containing domain may be or comprise a PDCD1, BTLA4, LILRB1, LAIR1, CTLA4, KIR2DL1, KIR2DL4, KIR2DL5, KIR3DL1 or KIR3DL3 endodomain. Suitably, the ITIM-containing domain may comprise the sequence shown any of SEQ ID NO: 15 to 24 or a variant thereof having at least 80, 85, 90, 95, 98 or 99% sequence identity which retains the capacity to be phosphorylated by Src kinases and amplify an inhibitory immune signal.

By way of example, the fusion protein may be or comprise the sequence shown as SEQ ID NO: 25, which contains a PTPN6-SH2 domain fused to a PD1 endodomain.

SEQ ID NO: 25
MTGQPLKEDPSAVPVFSVDYGELDFQWREKTPEPPVPCVPEQTEYATIVF

PSGMGTSSPARRGSADGPRSAQPLRPEDGHCSWPLSGGGGSGGGGSGGGG

-continued

```
SGGGGGSMVRWFHRDLSGLDAETLLKGRGVHGSFLARPSRKNQGDFSLSVR

VGDQVTHIRIQNSGDFYDLYGGEKFATLTELVEYYTQQQGVLQDRDGTII

HLKYPLNCSDPTSERWYHGHMSGGQAETLLQAKGEPWTFLVRESLSQPGD

FVLSVLSDQPKAGPGSPLRVTHIKVMCEGGRYTVGGLETFDSLTDLVEHF

KKTGIEEASGAFVYLRQPYYATRVNAADIENRVLELNKKQESEDTAKAGF

WEEFESLQKQEVKNLHQRLEGQRPENKGKNRYKNILPFDHSRVILQGRDS

NIPGSDYINANYIKNQLLGPDENAKTYIASQGCLEATVNDFWQMAWQENS

RVIVMTTREVEKGRNKCVPYWPEVGMQRAYGPYSVTNCGEHDTTEYKLRT

LQVSPLDNGDLIREIWHYQYLSWPDHGVPSEPGGVLSFLDQINQRQESLP

HAGPIIVHCSAGIGRTGTIIVIDMLMENISTKGLDCDIDIQKTIQMVRAQ

RSGMVQTEAQYKFIYVAIAQFIETTKKKLEVLQSQKGQESEYGNITYPPA

MKNAHAKASRTSSKHKEDVYENLHTKNKREEKVKKQRSADKEKSKGSLKR

K
```

Suitably, the fusion protein may comprise the sequence shown as SEQ ID NO: 25 or a variant thereof having at least 80, 85, 90, 95, 98 or 99% sequence identity Crosswire Signal The present invention provides a fusion protein which comprises: an SH2 domain from an ITAM-binding protein; and a phosphatase domain.

The present invention also provide a fusion protein which comprises: an SH2 domain from an ITIM-binding protein; and a kinase domain.

These "crosswire" signalling molecules will reverse an excitatory or inhibitory signal inside an immune cell such as a T cell. When a T-cell receives an excitatory signal, for example following recognition of a target antigen by a CAR, or MHC:peptide by a TCR, the presence of the first type of crosswire molecule will result in the cell interpreting the excitatory signal as an inhibitory signal.

Dampening down or revising T-cell activation may be useful in a variety of situations, for example, it may be used for CAR-expressing T cells where there is a high level of expression of the target antigen on the target cell. It may be used to prevent T-cell over-activation which may lead to T cell exhaustion and/or activation-induced cell death. Preventing a T-cell becoming activated too much or too quickly may also prevent or reduce pathological side effects of CAR-T cell treatment such as cytokine release syndrome (CRS).

The reverse situation is when a T-cell receives an inhibitory signal, for example following ligation of PD1, and the presence of the second type of crosswire molecule results in the cell interpreting the inhibitory signal as an excitatory signal.

Reducing or reversing T-cell inhibition will help the cell overcome the inhibitory stimuli within the hostile tumour microenvironment and should therefore increase T-cell persistence and expansion in vivo.

In one embodiment, the fusion protein comprises a PTPN6 SH2 domain and a ZAP70 kinase domain. In another embodiment the present fusion protein comprises a ZAP70 SH2 domain fused to a PTPN6 kinase domain.

In embodiments relating to a ZAP70 SH2 domain fused to the phosphatase domain from PTPN6, when the T cell receives an excitatory signal it interprets it as an inhibitory signal because the PTPN6 phosphatase domain is recruited to the activated ITAM via the ZAP70 SH2 domain.

In embodiments relating to a PTPN6 SH2 domain fused to the kinase domain from ZAP70, when the T cell receives an inhibitory signal it interprets it as an excitatory signal because the ZAP70 kinase domain is recruited to the activated ITIM via the PTPN6 domain. A fusion between PTPN6 SH2 domain and ZAP70 kinase domain will result in competition for phosphorylated ITIMs by wild-type PTPN6 blocking inhibitory signals, but in addition will transmit a paradoxical activation signal. This may have application in over-coming checkpoint blockade signals in a tumour microenvironment.

The sequence of human ZAP70 kinase, PTPN6 phosphatase and SHP-2 phosphatase domains domains are shown as SEQ ID NO: 26, 27 and 28 respectively.

```
ZAP70 kinase domain
                                        SEQ ID NO: 26
DPEELKDKKLFLKRDNLLIADIELGCGNFGSVRQGVYRMRKKQIDVAIKV

LKQGTEKADTEEMMREAQIMHQLDNPYIVRLIGVCQAEALMLVMEMAGGG

PLHKFLVGKREEIPVSNVAELLHQVSMGMKYLEEKNFVHRDLAARNVLLV

NRHYAKISDFGLSKALGADDSYYTARSAGKWPLKWYAPECINFRKFSSRS

DVWSYGVTMWEALSYGQKPYKKMKGPEVMAFIEQGKRMECPPECPPELYA

LMSDCWIYKWEDRPDFLTVEQRMRACYYSLASKVEGPPGSTQKAEAACA

PTPN6 phosphatase domain
                                        SEQ ID NO: 27
FWEEFESLQKQEVKNLHQRLEGQRPENKGKNRYKNILPFDHSRVILQGRD

SNIPGSDYINANYIKNQLLGPDENAKTYIASQGCLEATVNDFWQMAWQEN

SRVIVMTTREVEKGRNKCVPYWPEVGMQRAYGPYSVTNCGEHDTTEYKLR

TLQVSPLDNGDLIREIWHYQYLSWPDHGVPSEPGGVLSFLDQINQRQESL

PHAGPIIVHCSAGIGRTGTIIVIDMLMENISTKGLDCDIDIQKTIQMVRA

QRSGMVQTEAQYKFIYVAIAQFIETTKKKL

SHP-2 phosphatase domain
                                        SEQ ID NO: 28
WEEFETLQQQECKLLYSRKEGQRQENKNKNRYKNILPFDHTRVVLHDGDP

NEPVSDYINANIIMPEFETKCNNSKPKKSYIATQGCLQNTVNDFWRMVFQ

ENSRVIVMTTKEVERGKSKCVKYWPDEYALKEYGVMRVRNVKESAAHDYT

LRELKLSKVGQALLQGNTERTVWQYHFRTWPDHGVPSDPGGVLDFLEEVH

HKQESIMDAGPVVVHCSAGIGRTGTFIVIDILIDIIREKGVDCDIDVPKT

IQMVRSQRSGMVQTEAQYRFIYMA
```

The ZAP70 kinase domain, PTPN6 phosphatase domain or SHP-2 phosphatase domain may be or comprise the sequence shown as SEQ ID NO: 26, SEQ ID NO: 27 or SEQ ID NO: 28, respectively; or a variant thereof having at least 80, 85, 90, 95, 98 or 99% sequence identity which retains the capacity to phosphorylate or dephosphorylate downstream proteins in the same manner as the wild-type kinase/phosphatase domains.

Examples of fusion protein comprising a PTPN6 SH2 domain fused to a ZAP70 kinase domain; a ZAP70 SH2 domain fused to a PTPN6 kinase domain; and a SHP-2 SH2 domain fused to a ZAP70 kinase domain are shown as SEQ ID NO: 29, SEQ ID NO: 30 and SEQ ID No. 61, respectively.

PTPN6 SH2 domain fusion: ZAP70 kinase domain
SEQ ID NO: 29
MVRWFHRDLSGLDAETLLKGRGVHGSFLARPSRKNQGDFSLSVRVGDQVT

HIRIQNSGDFYDLYGGEKFATLTELVEYYTQQQGVLQDRDGTIIHLKYPL

NCSDPTSERWYHGHMSGGQAETLLQAKGEPWTFLVRESLSQPGDFVLSVL

SDQPKAGPGSPLRVTHIKVMCEGGRYTVGGLETFDSLTDLVEHFKKTGIE

EASGAFVYLRQPYYSGGGGSDPEELKDKKLFLKRDNLLIADIELGCGNFG

SVRQGVYRMRKKQIDVAIKVLKQGTEKADTEEMMREAQIMHQLDNPYIVR

LIGVCQAEALMLVMEMAGGGPLHKFLVGKREEIPVSNVAELLHQVSMGMK

YLEEKNFVHRDLAARNVLLVNRHYAKISDFGLSKALGADDSYYTARSAGK

WPLKWYAPECINFRKFSSRSDVWSYGVTMWEALSYGQKPYKKMKGPEVMA

FIEQGKRMECPPECPPELYALMSDCWIYKWEDRPDFLTVEQRMRACYYSL

ASKVEGPPGSTQKAEAACA

ZAP70 SH2 domain fusion: PTPN6 phosphatase domain
SEQ ID NO: 30
MPDPAAHLPFFYGSISRAEAEEHLKLAGMADGLFLLRQCLRSLGGYVLSL

VHDVRFHHFPIERQLNGTYAIAGGKAHCGPAELCEFYSRDPDGLPCNLRK

PCNRPSGLEPQPGVFDCLRDAMVRDYVRQTWKLEGEALEQAIISQAPQVE

KLIATTAHERMPWYHSSLTREEAERKLYSGAQTDGKFLLRPRKEQGTYAL

SLIYGKTVYHYLISQDKAGKYCIPEGTKFDTLWQLVEYLKLKADGLIYCL

KEACPNSSASNASGAAAPTLPAHPSTLTHPSGGGGSGGGGSGGGGSGGGG

SFWEEFESLQKQEVKNLHQRLEGQRPENKGKNRYKNILPFDHSRVILQGR

DSNIPGSDYINANYIKNQLLGPDENAKTYIASQGCLEATVNDFWQMAWQE

NSRVIVMTTREVEKGRNKCVPYWPEVGMQRAYGPYSVTNCGEHDTTEYKL

RTLQVSPLDNGDLIREIWHYQYLSWPDHGVPSEPGGVLSFLDQINQRQES

LPHAGPIIVHCSAGIGRTGTIIVIDMLMENISTKGLDCDIDIQKTIQMVR

AQRSGMVQTEAQYKFIYVAIAQFIETTKKKL dual SH2 domains from SHP-2 fused to ZAP70
kinase domain
SEQ ID NO. 61
WFHPNITGVEAENLLLTRGVDGSFLARPSKSNPGDFTLSVRRNGAVTHIK

IQNTGDYYDLYGGEKFATLAELVQYYMEHHGQLKEKNGDVIELKYPLNCA

DPTSERWFHGHLSGKEAEKLLTEKGKHGSFLVRESQSHPGDFVLSVRTGD

DKGESNDGKSKVTHVMIRCQELKYDVGGGERFDSLTDLVEHYKKNPMVET

LGTVLQLKQPLNTTRINPNSSASNASGAAAPTLPAHPSTLTHPQRRIDTL

NSDGYTPEPARITSPDKPRPMPMDTSVYESPYSDPEELKDKKLFLKRDNL

LIADIELGCGNFGSVRQGVYRMRKKQIDVAIKVLKQGTEKADTEEMMREA

QIMHQLDNPYIVRLIGVCQAEALMLVMEMAGGGPLHKFLVGKREEIPVSN

VAELLHQVSMGMKYLEEKNFVHRDLAARNVLLVNRHYAKISDFGLSKALG

ADDSYYTARSAGKWPLKWYAPECINFRKFSSRSDVWSYGVTMWEALSYGQ

KPYKKMKGPEVMAFIEQGKRMECPPECPPELYALMSDCWIYKWEDRPDFL

TVEQRMRACYYSL

The fusion protein may be or comprise the sequence shown as SEQ ID NO: 29, SEQ ID NO: 30 or SEQ ID No. 61 or a variant thereof having at least 80, 85, 90, 95, 98 or 99% sequence identity.

Heterologous Signalling Domain

The present fusion protein may comprise (i) a ZAP70, PTPN6 or SHP-2 SH2 domain; and (ii) a heterologous signalling domain.

As used herein, the term "heterologous signalling domain" refers to a signalling domain which is not present in the wild type ZAP70, PTPN6 or SHP-2 protein. As such, where the fusion protein comprises a ZAP70 SH2 domain, it comprises a signalling domain which is not the ZAP70 kinase domain. Alternatively, where the fusion protein comprises a PTPN6 SH2 domain, it comprises a signalling domain which is not the PTPN6 phosphatase domain.

Bypass Signal

The heterologous signalling domain may be from a signalling molecule which is not usually activated by an ITAM containing receptor. In other words, the heterologous signalling domain may be from a signalling molecule which is not involved in the propagation of immunological signal 1 following the binding of antigen to the TCR. Immunological signal 1 is sufficient to trigger T-cell killing of cognate target cells but does not fully activate the T-cell to proliferate and survive.

In one embodiment of this aspect of the invention, the present invention provides a fusion protein which comprises (i) an SH2 domain from a protein which binds an ITAM; and (ii) a heterologous signalling domain.

A fusion between, for example, ZAP70 and another signaling molecule not typically activated with an ITAM containing receptor may act to bypass signal from one pathway into another. One example is co-stimulation. A fusion between ZAP70 and the endodomain of CD28 may transmit a CD28 co-stimulatory signal as well as an ITAM activatory signal. Similarly, a fusion between ZAP70 and the endodomain of 41 BB or OX40 may transmit a 41 BB or OX40 co-stimulatory signal. Other pathways may also be recruited, for instance a fusion between ZAP70 and AKT kinase domain may result in transmission of an AKT signal upon ITAM phosphorylation. Other examples might include Kinase domain from JAK. In this way, a T-cell may interpret a simple antigen recognition signal as transmitting a co-stimulatory or even a cytokine type signal.

Such fusion proteins may be useful, for example, in approaches where repeated ex vivo stimulations of T cells can result in populations which lack costimulatory surface antigens and which have limited proliferative capacity in vivo resulting in limited persistence and efficacy. The loss of costimulatory surface antigens leading to activation of T cells solely through the TCR has been linked to a greater degree of activation induced cell death which would negatively impact in vivo efficacy and persistence. The effect can be reversed by the activation of surface-expressed 4-1 BB and OX40 demonstrating that costimulation can prevent activation induced cell death and can support greater expansion of tumour specific T cells.

In another embodiment of this aspect of the invention, the present invention provides a fusion protein which comprises (i) an SH2 domain from a protein which binds an ITIM; and (ii) a heterologous signalling domain.

For example, a PTPN6 SH2 domain or SHP-2 SH2 domain may be fused to a co-stimulatory endodomain so a T-cell interprets an inhibitory signal as a co-stimulatory one.

The heterologous signalling domain may be from, for example, CD28, 41 BB or OX40.

CD28 provides a potent co-stimulatory signal—namely immunological signal 2, which triggers T-cell proliferation. CD28 is the receptor for CD80 (B7.1) and CD86 (B7.2) proteins.

41BB (CD137) is a type 2 transmembrane glycoprotein belonging to the TNF superfamily, expressed on activated T cells. Crosslinking of 41BB enhances T cell proliferation, IL-2 secretion survival and cytolytic activity.

OX40 (CD134) is a secondary co-stimulatory molecule, expressed after 24 to 72 hours following activation; its ligand, OX40L, is also not expressed on resting antigen presenting cells, but is following their activation. Expression of OX40 is dependent on full activation of the T cell; without CD28, expression of OX40 is delayed and of fourfold lower levels. Signalling through OX40 is required for prolonged T cell survival following initial activation and proliferation.

The CD28, 41BB and OX40 signalling domains (endodomains) are shown as SEQ ID NO: 31, 32 and 33, respectively.

```
CD28 endodomain
                                    SEQ ID NO: 31
MRSKRSRLLHSDYMNMTPRRPGPTRKHYQPYAPPRDFAAYRS 41BB endodomain
                                    SEQ ID NO: 32
MKRGRKKLLYIFKQPFMRPVQTTQEEDGCSCRFPEEEEGGCEL OX40 endodomain
                                    SEQ ID NO: 33
MRDQRLPPDAHKPPGGGSFRTPIQEEQADAHSTLAKI
```

The heterologous signalling domain may be or comprise the sequence shown as SEQ ID NO: 31; SEQ ID NO: 32 or SEQ ID NO: 33, respectively, or a variant thereof having at least 80, 85, 90, 95, 98 or 99% sequence identity.

The heterologous signalling domain may be or comprise an inhibitory signalling domain.

For example, the inhibitory signalling domain may comprise the endodomain of CD148 or CD45. CD148 and CD45 have been shown to act naturally on the phosphorylated tyrosines up-stream of TCR signalling.

CD148 is a receptor-like protein tyrosine phosphatase which negatively regulates TCR signaling by interfering with the phosphorylation and function of PLCγ1 and LAT.

CD45 present on all hematopoetic cells, is a protein tyrosine phosphatase which is capable of regulating signal transduction and functional responses, again by phosphorylating PLC γ1.

An inhibitory signalling domain may comprise all of part of a receptor-like tyrosine phosphatase. The phospatase may interfere with the phosphorylation and/or function of elements involved in T-cell signalling, such as PLCγ1 and/or LAT.

The inhibitory signalling domain may be or comprise the endodomain of ICOS, CD27, BTLA, CD30, GITR or HVEM.

The inhibitory signalling domain may comprise the sequence shown as SEQ ID NO: 34 to 39 or a variant thereof having at least 80% sequence identity.

```
ICOS endodomain
                                    SEQ ID NO: 34
CWLTKKKYSSSVHDPNGEYMFMRAVNTAKKSRLTDVTL CD27 endodomain
                                    SEQ ID NO: 35
QRRKYRSNKGESPVEPAEPCHYSCPREEEGSTIPIQEDYRKPEPACSP BTLA endodomain
                                    SEQ ID NO: 36
RRHQGKQNELSDTAGREINLVDAHLKSEQTEASTRQNSQVLLSETGIYDN
DPDLCFRMQEGSEVYSNPCLEENKPGIVYASLNHSVIGPNSRLARNVKEA
PTEYASICVRS CD30 endodomain
                                    SEQ ID NO: 37
HRRACRKRIRQKLHLCYPVQTSQPKLELVDSRPRRSSTQLRSGASVTEPV
AEERGLMSQPLMETCHSVGAAYLESLPLQDASPAGGPSSPRDLPEPRVST
EHTNNKIEKIYIMKADTVIVGTVKAELPEGRGLAGPAEPELEEELEADHT
PHYPEQETEPPLGSCSDVMLSVEEEGKEDPLPTAASGK GITR endodomain
                                    SEQ ID NO: 38
QLGLHIWQLRSQCMWPRETQLLLEVPPSTEDARSCQFPEEERGERSAEEK
GRLGDLWV HVEM endodomain
                                    SEQ ID NO: 39
CVKRRKPRGDVVKVIVSVQRKRQEAEGEATVIEALQAPPDVTTVAVEETI
PSFTGRSPNH
```

A variant sequence may have at least 80%, 85%, 90%, 95%, 98% or 99% sequence identity to SEQ ID NO: 34 to 39 provided that the sequence provides an effective intracellular signalling domain.

Suitably, the fusion protein may be or comprise any of the sequences shown as SEQ ID NOs: 40 to 45.

```
CD28 endodomain fused to amino-terminus of
full-length ZAP
                                    (SEQ ID NO: 40)
MRSKRSRLLHSDYMNMTPRRPGPTRKHYQPYAPPRDFAAYRSSGGGSGG
GGSGGGGSGGGGSMPDPAAHLPFFYGSISRAEAEEHLKLAGMADGLFLLR
QCLRSLGGYVLSLVHDVRFHHFPIERQLNGTYAIAGGKAHCGPAELCEFY
SRDPDGLPCNLRKPCNRPSGLEPQPGVFDCLRDAMVRDYVRQTWKLEGEA
LEQAIISQAPQVEKLIATTAHERMPWYHSSLTREEAERKLYSGAQTDGKF
LLRPRKEQGTYALSLIYGKTVYHYLISQDKAGKYCIPEGTKFDTLWQLVE
YLKLKADGLIYCLKEACPNSSASNASGAAAPTLPAHPSTLTHPQRRIDTL
NSDGYTPEPARITSPDKPRPMPMDTSVYESPYSDPEELKDKKLFLKRDNL
LIADIELGCGNFGSVRQGVYRMRKKQIDVAIKVLKQGTEKADTEEMMREA
QIMHQLDNPYIVRLIGVCQAEALMLVMEMAGGGPLHKFLVGKREEIPVSN
VAELLHQVSMGMKYLEEKNFVHRDLAARNVLLVNRHYAKISDFGLSKALG
ADDSYYTARSAGKWPLKWYAPECINFRKFSSRSDVWSYGVTMWEALSYGQ
KPYKKMKGPEVMAFIEQGKRMECPPECPPELYALMSDCWIYKWEDRPDFL
TVEQRMRACYYSLASKVEGPPGSTQKAEAACA 41BB endodomain fused to amino-terminus of
full-length ZAP
                                    (SEQ ID NO: 41)
MKRGRKKLLYIFKQPFMRPVQTTQEEDGCSCRFPEEEEGGCELSGGGGSG
GGGSGGGGSGGGGSMPDPAAHLPFFYGSISRAEAEEHLKLAGMADGLFLL
RQCLRSLGGYVLSLVHDVRFHHFPIERQLNGTYAIAGGKAHCGPAELCEF
```

```
YSRDPDGLPCNLRKPCNRPSGLEPQPGVFDCLRDAMVRDYVRQTWKLEGE

ALEQAIISQAPQVEKLIATTAHERMPWYHSSLTREEAERKLYSGAQTDGK

FLLRPRKEQGTYALSLIYGKTVYHYLISQDKAGKYCIPEGTKFDTLWQLV

EYLKLKADGLIYCLKEACPNSSASNASGAAAPTLPAHPSTLTHPQRRIDT

LNSDGYTPEPARITSPDKPRPMPMDTSVYESPYSDPEELKDKKLFLKRDN

LLIADIELGCGNFGSVRQGVYRMRKKQIDVAIKVLKQGTEKADTEEMMRE

AQIMHQLDNPYIVRLIGVCQAEALMLVMEMAGGGPLHKFLVGKREEIPVS

NVAELLHQVSMGMKYLEEKNFVHRDLAARNVLLVNRHYAKISDFGLSKAL

GADDSYYTARSAGKWPLKWYAPECINFRKFSSRSDVWSYGVTMWEALSYG

QKPYKKMKGPEVMAFIEQGKRMECPPECPPELYALMSDCWIYKWEDRPDF

LTVEQRMRACYYSLASKVEGPPGSTQKAEAACA

OX40 endodomain fused to amino-terminus of
full-length ZAP
                                    (SEQ ID NO: 42)
MRDQRLPPDAHKPPGGGSFRTPIQEEQADAHSTLAKISGGGGSGGGGSGG

GGSGGGGSMPDPAAHLPFFYGSISRAEAEEHLKLAGMADGLFLLRQCLRS

LGGYVLSLVHDVRFHHFPIERQLNGTYAIAGGKAHCGPAELCEFYSRDPD

GLPCNLRKPCNRPSGLEPQPGVFDCLRDAMVRDYVRQTWKLEGEALEQAI

ISQAPQVEKLIATTAHERMPWYHSSLTREEAERKLYSGAQTDGKFLLRPR

KEQGTYALSLIYGKTVYHYLISQDKAGKYCIPEGTKFDTLWQLVEYLKLK

ADGLIYCLKEACPNSSASNASGAAAPTLPAHPSTLTHPQRRIDTLNSDGY

TPEPARITSPDKPRPMPMDTSVYESPYSDPEELKDKKLFLKRDNLLIADI

ELGCGNFGSVRQGVYRMRKKQIDVAIKVLKQGTEKADTEEMMREAQIMHQ

LDNPYIVRLIGVCQAEALMLVMEMAGGGPLHKFLVGKREEIPVSNVAELL

HQVSMGMKYLEEKNFVHRDLAARNVLLVNRHYAKISDFGLSKALGADDSY

YTARSAGKWPLKWYAPECINFRKFSSRSDVWSYGVTMWEALSYGQKPYKK

MKGPEVMAFIEQGKRMECPPECPPELYALMSDCWIYKWEDRPDFLTVEQR

MRACYYSLASKVEGPPGSTQKAEAACA

CD28 endodomain fused to the amino-terminus of
PTPN6 SH2 domain.
                                    (SEQ ID NO: 43)
MRSKRSRLLHSDYMNMTPRRPGPTRKHYQPYAPPRDFAAYRSSGGGGSGG

GGSGGGGSGGGGSMVRWFHRDLSGLDAETLLKGRGVHGSFLARPSRKNQG

DFSLSVRVGDQVTHIRIQNSGDFYDLYGGEKFATLTELVEYYTQQQGVLQ

DRDGTIIHLKYPLNCSDPTSERWYHGHMSGGQAETLLQAKGEPWTFLVRE

SLSQPGDFVLSVLSDQPKAGPGSPLRVTHIKVMCEGGRYTVGGLETFDSL

TDLVEHFKKTGIEEASGAFVYLRQPY

41BB endodomain fused to the amino-terminus of
PTPN6 SH2 domain
                                    (SEQ ID NO: 44)
MKRGRKKLLYIFKQPFMRPVQTTQEEDGCSCRFPEEEEGGCELSGGGGSG

GGGSGGGGSGGGGSMVRWFHRDLSGLDAETLLKGRGVHGSFLARPSRKNQ

GDFSLSVRVGDQVTHIRIQNSGDFYDLYGGEKFATLTELVEYYTQQQGVL

QDRDGTIIHLKYPLNCSDPTSERWYHGHMSGGQAETLLQAKGEPWTFLVR

ESLSQPGDFVLSVLSDQPKAGPGSPLRVTHIKVMCEGGRYTVGGLETFDS

LTDLVEHFKKTGIEEASGAFVYLRQPY

OX40 endodomain fused to the amino-terminus of
PTPN6 SH2 domain
                                    (SEQ ID NO: 45)
MRDQRLPPDAHKPPGGGSFRTPIQEEQADAHSTLAKISGGGGSGGGGSGG

GGSGGGGSMVRWFHRDLSGLDAETLLKGRGVHGSFLARPSRKNQGDFSLS

VRVGDQVTHIRIQNSGDFYDLYGGEKFATLTELVEYYTQQQGVLQDRDGT

IIHLKYPLNCSDPTSERWYHGHMSGGQAETLLQAKGEPWTFLVRESLSQP

GDFVLSVLSDQPKAGPGSPLRVTHIKVMCEGGRYTVGGLETFDSLTDLVE

HFKKTGIEEASGAFVYLRQPY
```

Suitably, the fusion protein may comprise the sequence shown as any of SEQ ID NOs: 40 to 45 or a variant thereof having at least 80, 85, 90, 95, 98 or 99% sequence identity Kinase Domain The heterologous signalling domain may be a kinase domain. For example, the heterologous signalling domain may comprise an AKT kinase domain or a JAK kinase domain.

Akt, also known as protein kinase B (PKB), is a serine/threonine-specific protein kinase that plays a key role in multiple cellular processes such as glucose metabolism, apoptosis, cell proliferation, transcription and cell migration.

Following activation of the TCR, T cells secrete IL2 which supports survival and proliferation. However this secretion is transient and T cells that are activated and expanded in vitro become dependent on exogenous IL2 for survival. By increasing AKT phosphorylation following ITAM phosphorylation associated with TCR or CAR activation, the dependence of activated T cells on exogenous IL2 may be reduced or removed and their proliferation and survival enhanced.

The Akt kinase domain is shown as SEQ ID NO: 46.

```
Akt kinase domain
                                    SEQ ID NO: 46
AEEMEVSLAKPKHRVTMNEFEYLKLLGKGTFGKVILVKEKATGRYYAMKI

LKKEVIVAKDEVAHTLTENRVLQNSRHPFLTALKYSFQTHDRLCFVMEYA

NGGELFFHLSRERVFSEDRARFYGAEIVSALDYLHSEKNVVYRDLKLENL

MLDKDGHIKITDFGLCKEGIKDGATMKTFCGTPEYLAPEVLEDNDYGRAV

DWWGLGVVMYEMMCGRLPFYNQDHEKLFELILMEEIRFPRTLGPEAKSLL

SGLLKKDPKQRLGGGSEDAKEIMQHRFFAGIVWQHVYEKKLSPPPFKPQVT

SETDTRYFDEEFTAQMITITPPDQDDSMECVDSERRPHFPQFSYSASGTA
```

The heterologous signalling domain may be or comprise the sequence shown as SEQ ID NO: 46, or a variant thereof having at least 80, 85, 90, 95, 98 or 99% sequence identity provided that the sequence provides an effective kinase domain.

By way of example, the fusion protein may be or comprise the any of the sequences shown as SEQ ID NO: 47 to 49 and 62 which contain a ZAP70-SH2 domain fused directly to an Akt kinase domain, a ZAP70-SH2 domain fused to an Akt kinase domain via a linker a ZAP70 mutated to be non-functional and fused to an Akt kinase domain; and a dual SHP-2 SH2 domain fused to an Akt kinase domain, respectively.

ZAP70-SH2 domain fused directly to an Akt kinase domain

SEQ ID NO: 47

MPDPAAHLPFFYGSISRAEAEEHLKLAGMADGLFLLRQCLRSLGGYVLSL

VHDVRFHHFPIERQLNGTYAIAGGKAHCGPAELCEFYSRDPDGLPCNLRK

PCNRPSGLEPQPGVFDCLRDAMVRDYVRQTWKLEGEALEQAIISQAPQVE

KLIATTAHERMPWYHSSLTREEAERKLYSGAQTDGKFLLRPRKEQGTYAL

SLIYGKTVYHYLISQDKAGKYCIPEGTKFDTLWQLVEYLKLKADGLIYCL

KEACPNSSASNASGAAAPTLPAHPSTLTHPAEEMEVSLAKPKHRVTMNEF

EYLKLLGKGTFGKVILVKEKATGRYYAMKILKKEVIVAKDEVAHTLTENR

VLQNSRHPFLTALKYSFQTHDRLCFVMEYANGGELFFHLSRERVFSEDRA

RFYGAEIVSALDYLHSEKNVVYRDLKLENLMLDKDGHIKITDFGLCKEGI

KDGATMKTFCGTPEYLAPEVLEDNDYGRAVDWWGLGVVMYEMMCGRLPFY

NQDHEKLFELILMEEIRFPRTLGPEAKSLLSGLLKKDPKQRLGGGSEDAK

EIMQHRFFAGIVWQHVYEKKLSPPFKPQVTSETDTRYFDEEFTAQMITIT

PPDQDDSMECVDSERRPHFPQFSYSASGTA

ZAP70-SH2 domain fused to an Akt kinase domain via a linker

SEQ ID NO: 48

MPDPAAHLPFFYGSISRAEAEEHLKLAGMADGLFLLRQCLRSLGGYVLSL

VHDVRFHHFPIERQLNGTYAIAGGKAHCGPAELCEFYSRDPDGLPCNLRK

PCNRPSGLEPQPGVFDCLRDAMVRDYVRQTWKLEGEALEQAIISQAPQVE

KLIATTAHERMPWYHSSLTREEAERKLYSGAQTDGKFLLRPRKEQGTYAL

SLIYGKTVYHYLISQDKAGKYCIPEGTKFDTLWQLVEYLKLKADGLIYCL

KEACPNSSASNASGAAAPTLPAHPSTLTHPSGGGGSGGGGSGGGGSGGGG

SAEEMEVSLAKPKHRVTMNEFEYLKLLGKGTFGKVILVKEKATGRYYAMK

ILKKEVIVAKDEVAHTLTENRVLQNSRHPFLTALKYSFQTHDRLCFVMEY

ANGGELFFHLSRERVFSEDRARFYGAEIVSALDYLHSEKNVVYRDLKLEN

LMLDKDGHIKITDFGLCKEGIKDGATMKTFCGTPEYLAPEVLEDNDYGRA

VDWWGLGVVMYEMMCGRLPFYNQDHEKLFELILMEEIRFPRTLGPEAKSL

LSGLLKKDPKQRLGGGSEDAKEIMQHRFFAGIVWQHVYEKKLSPPFKPQV

TSETDTRYFDEEFTAQMITITPPDQDDSMECVDSERRPHFPQFSYSASGT

A

ZAP70 mutated to be non-functional and fused to an Akt kinase domain

SEQ ID NO: 49

MPDPAAHLPFFYGSISRAEAEEHLKLAGMADGLFLLRQCLRSLGGYVLSL

VHDVRFHHFPIERQLNGTYAIAGGKAHCGPAELCEFYSRDPDGLPCNLRK

PCNRPSGLEPQPGVFDCLRDAMVRDYVRQTWKLEGEALEQAIISQAPQVE

KLIATTAHERMPWYHSSLTREEAERKLYSGAQTDGKFLLRPRKEQGTYAL

SLIYGKTVYHYLISQDKAGKYCIPEGTKFDTLWQLVEYLKLKADGLIYCL

KEACPNSSASNASGAAAPTLPAHPSTLTHPAEEMEVSLAKPKHRVTMNEF

EYLKLLGKGTFGKVILVKEKATGRYYAMKILKKEVIVAKDEVAHTLTENR

VLQNSRHPFLTALKYSFQTHDRLCFVMEYANGGELFFHLSRERVFSEDRA

RFYGAEIVSALDYLHSEKNVVYRDLKLENLMLDKDGHIKITDFGLCKEGI

-continued

KDGATMKTFCGTPEYLAPEVLEDNDYGRAVDWWGLGVVMYEMMCGRLPFY

NQDHEKLFELILMEEIRFPRTLGPEAKSLLSGLLKKDPKQRLGGGSEDAK

EIMQHRFFAGIVWQHVYEKKLSPPFKPQVTSETDTRYFDEEFTAQMITIT

PPDQDDSMECVDSERRPHFPQFSYSASGTA dual SHP-2 SH2 domain fused to an Akt kinase domain SEQ ID No. 62

WFHPNITGVEAENLLLTRGVDGSFLARPSKSNPGDFTLSVRRNGAVTHIK

IQNTGDYYDLYGGEKFATLAELVQYYMEHHGQLKEKNGDVIELKYPLNCA

DPTSERWFHGHLSGKEAEKLLTEKGKHGSFLVRESQSHPGDFVLSVRTGD

DKGESNDGKSKVTHVMIRCQELKYDVGGGERFDSLTDLVEHYKKNPMVET

LGTVLQLKQPLNTTRINAEEMEVSLAKPKHRVTMNEFEYLKLLGKGTFGK

VILVKEKATGRYYAMKILKKEVIVAKDEVAHTLTENRVLQNSRHPFLTAL

KYSFQTHDRLCFVMEYANGGELFFHLSRERVFSEDRARFYGAEIVSALDY

LHSEKNVVYRDLKLENLMLDKDGHIKITDFGLCKEGIKDGATMKTFCGTP

EYLAPEVLEDNDYGRAVDWWGLGVVMYEMMCGRLPFYNQDHEKLFELILM

EEIRFPRTLGPEAKSLLSGLLKKDPKQRLGGGSEDAKEIMQHRFFAGIVW

QHVYEKKLSPPFKPQVTSETDTRYFDEEFTAQMITITPPDQDDSMECVDS

ERRPHFPQFSYSASGTA

The fusion protein may comprise the sequence shown as any of SEQ ID NO: 47 to 49 or 62 or a variant thereof having at least 80, 85, 90, 95, 98 or 99% sequence identity.

Janus kinase (JAK) is a family of intracellular, nonreceptor tyrosine kinases that transduce cytokine-mediated signals via the JAK-STAT pathway. The four JAK family members are: Janus kinase 1 (JAK1); Janus kinase 2 (JAK2); Janus kinase 3 (JAK3); and Tyrosine kinase 2 (TYK2).

Kinase containing domain of JAK2

SEQ ID NO: 50

RNEDLIFNESLGQGTFTKIFKGVRREVGDYGQLHETEVLLKVLDKAHRNY

SESFFEAASMMSKLSHKHLVLNYGVCVCGDENILVQEFVKFGSLDTYLKK

NKNCINILWKLEVAKQLAWAMHFLEENTLIHGNVCAKNILLIREEDRKTG

NPPFIKLSDPGISITVLPKDILQERIPWVPPECIENPKNLNLATDKWSFG

TTLWEICSGGDKPLSALDSQRKLQFYEDRHQLPAPKWAELANLINNCMDY

EPDFRPSFRAIIRDLNSLFTPDYELLTENDMLPNMRIGALGFSGAFEDRD

PTQFEERHLKFLQQLGKGNFGSVEMCRYDPLQDNTGEVVAVKKLQHSTEE

HLRDFEREIEILKSLQHDNIVKYKGVCYSAGRRNLKLIMEYLPYGSLRDY

LQKHKERIDHIKLLQYTSQICKGMEYLGTKRYIHRDLATRNILVENENRV

KIGDFGLTKVLPQDKEYYKVKEPGESPIFWYAPESLTESKFSVASDVWSF

GVVLYELFTYIEKSKSPPAEFMRMIGNDKQGQMIVFHLIELLKNNGRLPR

PDGCPDEIYMIMTECWNNNVNQRPSFRDLALRVDQIRDNM

Protease Domain

The present invention also provides a fusion protein which comprises (i) an SH2 domain from a protein which binds an ITAM or ITIM-containing protein and (ii) a protease domain.

The protease domain may be any protease which is capable of cleaving at a specific recognition sequence. As such the protease domain may be any protease which enables the separation of a single target polypeptide into two distinct polypeptides via cleavage at a specific target sequence.

The protease domain may be a Tobacco Etch Virus (TeV) protease domain.

TeV protease is a highly sequence-specific cysteine protease which is chymotrypsin-like proteases. It is very specific for its target cleavage site and is therefore frequently used for the controlled cleavage of fusion proteins both in vitro and in vivo. The consensus TeV cleavage site is ENLYFQ\S (where '\' denotes the cleaved peptide bond). Mammalian cells, such as human cells, do not express endogenous TeV protease.

Accordingly, the TeV cleavage recognition site is shown as SEQ ID NO: 51.

SEQ ID NO: 51—Tev cleavage site
ENLYFQS

The TeV protease domain is shown as SEQ ID NO: 52.

```
                                           SEQ ID NO: 52
SLFKGPRDYNPISSTICHLTNESDGHTTSLYGIGFGPFIITNKHLFRRNN

GTLLVQSLHGVFKVKNTTTLQQHLIDGRDMIIIRMPKDFPPFPQKLKFRE

PQREERICLVTTNFQTKSMSSMVSDTSCTFPSSDGIFWKHWIQTKDGQCG

SPLVSTRDGFIVGIHSASNFTNTNNYFTSVPKNFMELLTNQEAQQWVSGW

RLNADSVLWGGHKVFMSKPEEPFQPVKEATQLMNELVYSQ
```

Accordingly, the protease domain may be or comprise the sequence shown as SEQ ID NO: 52, or a variant thereof having at least 80, 85, 90, 95, 98 or 99% sequence identity provided that the sequence provides an effective protease function.

By way of example, the fusion protein may be or comprise the sequence shown as SEQ ID NO: 53 or 54, which contains a ZAP70-SH2 domain fused to a TEV protease sequence or a PTPN6-SH2 domain fused to a TEV protease sequence; respectively.

```
                                           SEQ ID NO: 53
MPDPAAHLPFFYGSISRAEAEEHLKLAGMADGLFLLRQCLRSLGGYVLSL

VHDVRFHHFPIERQLNGTYAIAGGKAHCGPAELCEFYSRDPDGLPCNLRK

PCNRPSGLEPQPGVFDCLRDAMVRDYVRQTWKLEGEALEQAIISQAPQVE

KLIATTAHERMPWYHSSLTREEAERKLYSGAQTDGKFLLRPRKEQGTYAL

SLIYGKTVYHYLISQDKAGKYCIPEGTKFDTLWQLVEYLKLKADGLIYCL

KEACPNSSASNASGAAAPTLPAHPSTLTHPSGGGGSGGGGSGGGGSGGGG

SSLFKGPRDYNPISSTICHLTNESDGHTTSLYGIGFGPFIITNKHLFRRN

NGTLLVQSLHGVFKVKNTTTLQQHLIDGRDMIIIRMPKDFPPFPQKLKFR

EPQREERICLVTTNFQTKSMSSMVSDTSCTFPSSDGIFWKHWIQTKDGQC

GSPLVSTRDGFIVGIHSASNFTNTNNYFTSVPKNFMELLTNQEAQQWV

SGWRLNADSVLWGGHKVFMSKPEEPFQPVKEATQLMNELVYSQ

SEQ ID NO: 54
MVRWFHRDLSGLDAETLLKGRGVHGSFLARPSRKNQGDFSLSVRVGDQVT

HIRIQNSGDFYDLYGGEKFATLTELVEYYTQQQGVLQDRDGTIIHLKYPL

NCSDPTSERWYHGHMSGGQAETLLQAKGEPWTFLVRESLSQPGDFVLSVL

SDQPKAGPGSPLRVTHIKVMCEGGRYTVGGLETFDSLTDLVEHFKKTGIE

EASGAFVYLRQPYYSGGGGSSLFKGPRDYNPISSTICHLTNESDGHTTSL

YGIGFGPFIITNKHLFRRNNGTLLVQSLHGVFKVKNTTTLQQHLIDGRDM

IIIRMPKDFPPFPQKLKFREPQREERICLVTTNFQTKSMSSMVSDTSCTF

PSSDGIFWKHWIQTKDGQCGSPLVSTRDGFIVGIHSASNFTNTNNYFTSV

PKNFMELLTNQEAQQWVSGWRLNADSVLWGGHKVFMSKPEEPFQPVKEAT

QLMNELVYSQ
```

The fusion protein may comprise the sequence shown as SEQ ID NO: 53 or 54; or a variant thereof having at least 80, 85, 90, 95, 98 or 99% sequence identity.

The SH2 domain and heterologous domain of the fusion protein may be separated by a linker in order to spatially separate the SH2 domain and the heterologous domain.

Transcriptional Signal

A fusion protein which comprises a protease, as described in the previous section, may be co-expressed in a cell with a membrane-tethered protein having a protease cleavage site. Cleavage of the membrane-tethered protein at the protease site will release the membrane-distal part of the protein.

The membrane tethered protein may, for example, be a membrane-tethered transcription factor. When cleavage occurs, the transcription is released from its tether and free to transit to the nucleus.

A fusion between ZAP70 SH2 or PTPN6 SH2 domain and a protease domain will result in membrane-proximal recruitment of the protease following ITAM or ITIM phosphorylation, respectively.

Phosphorylation of ITAM or ITIM domains results in recruitment of the ZAP70 SH2 or PTPN6 SH2 fused with the protease domain, respectively, to the membrane-proximal area. This results in the transcription factor being cleaved from its tether and transferred to the nucleus. This may have many applications: for example upon activation the T-cell may be programmed to express transcription factors which act to prevent the T-cell from differentiating. For instance, upon activation the T-cell may be programmed to express a cytokine such as IL2, IL7 or IL15 which may act to stimulate proliferation and survival of the T-cell, or IL12 which may convert a hostile tumour microenvironment to one which more favours immune rejection of a tumour.

In particular, there is provided a cell which co-expresses:
(i) a fusion protein comprising an SH2 domain from a protein which binds a phosphorylated ITAM; and
(ii) a membrane tethered transcription factor
wherein the transcription factor, when released from the membrane tether, increases the expression of IL2, Il7 and/or IL5 in the cell.

There is also provided a cell which co-expresses:
(i) a fusion protein comprising an SH2 domain from a protein which binds a phosphorylated ITIM; and
(ii) a membrane tethered transcription factor
wherein the transcription factor, when released from the membrane tether, increases the expression of IL2 in the cell.

Protease Recognition Site

The protease recognition site may be any amino acid sequence which enables the protease domain of the fusion protein to specifically cleave the membrane tethered transcription factor between the membrane tether and the transcription factor. For example, in one embodiment the protease domain is a TeV protease domain and the protease recognition site is a TeV protease recognition site.

Membrane Tether

The membrane tether may be any sequence, signal or domain which is capable of localising the transcription factor and protease recognition site proximal to a membrane. For example, the membrane tether may be a myrsitylation signal or a transmembrane domain.

Suitably, a transmembrane domain may be any protein structure which is thermodynamically stable in a membrane. This is typically an alpha helix comprising of several hydrophobic residues. The transmembrane domain of any transmembrane protein can be used to supply the transmembrane portion. The presence and span of a transmembrane domain of a protein can be determined by those skilled in the art using the TMHMM algorithm (http://www.cbs.dtu.dk/services/TMHMM-2.0/). Further, given that the transmembrane domain of a protein is a relatively simple structure, i.e a polypeptide sequence predicted to form a hydrophobic alpha helix of sufficient length to span the membrane, an artificially designed TM domain may also be used (U.S. Pat. No. 7,052,906 B1 describes synthetic transmembrane components).

The transmembrane domain may be derived from CD28, which gives good stability.

Transcription Factor

The transcription factor may be any transcription factor chosen to stimulate a desired response following phosphorylation of the relevant ITAM or ITIM motifs.

The transcripton factor can be natural or artificial. Artificial transcription factors may be derived from, for example, TALENs, zinc-finger assemblies or CrispR/CAS9, the latter co-expressed with a guide mRNA.

Preferably, the transcription factor will contain a nuclear localization signal to aid its transportation to the nuclease following cleavage by the protease domain.

By way of example, nucleic acid sequence (ii) (which encodes a protein comprising a membrane tethered transcription factor which comprises: (i) a membrane tether; (ii) a protease recognition site; and (iii) a transcription factor) may encode a protein which consists of or comprises the sequence shown as SEQ ID NO: 55, which contains a RQR8 domain; a CD4-Endotox1 transmembrane domain, a TEV protease recognition site and a VP16-GAL4 transcription factor.

SEQ ID NO: 55
MGTSLLCWMALCLLGADHADACPYSNPSLCSGGGGSELPTQGTFSNVSTN

VSPAKPTTTACPYSNPSLCSGGGGSPAPRPPTPAPTIASQPLSLRPEACR

PAAGGAVHTRGLDFACDMALIVLGGVAGLLLFIGLGIFFCVRCRHRRRQA

ERMAQIKRVVSEKKTAQAPHRFQKTCSPISGGGGSENLYFQMPKKKRKVA

PPTDVSLGDELHLDGEDVAMAHADALDDFDLDMLGDGDSPGPGFTPHDSA

PYGALDMADFEFEQMFTDALGIDEYGGSGGGSMQILVASDATMKLLSSIE

QACDICRLKKLKCSKEKPKCAKCLKNNWECRYSPKTKRSPLTRAHLTEVE

SRLERLEQLFLLIFPREDLDMILKMDSLQDIKALLTGLFVQDNVNKDAVT

DRLASVETDMPLTLRQHRISATSSSEESSNKGQRQLTV

Suitably, the protein may comprise the sequence shown as SEQ ID NO: 55; or a variant thereof having at least 80, 85, 90, 95, 98 or 99% sequence identity Receptor The present invention further provides a nucleic acid construct which comprises (a) a nucleic acid sequence encoding a fusion protein according to the first aspect of the present invention which comprises a PTPN6 SH2 domain, or a truncated protein according to the third aspect of the present invention; and (b) a nucleic acid sequence encoding a receptor comprising an ITIM containing endodomain.

Castration Signal

A fusion protein which comprises a protease, as described above, may be co-expressed in a cell with a target receptor which comprises an intracellular protease cleavage site. Cleavage of the target receptor at the protease site will release an intracellular, membrane-distal part of the target receptor.

The target receptor may, for example, be a T-cell receptor (TCR), or a chimeric antigen receptor (CAR).

The receptor may comprise an activatory or co-stimulatory endodomain positioned at the end of the intracellular part of the protein. Cleavage at the protease cleavage site then removes the activatory or co-stimulatory endodomain from the target CAR, reducing or preventing target receptor-mediated T cell activation.

Alternatively, the target receptor may comprise an inhibitory endodomain positioned at the end of the intracellular part of the protein. Cleavage at the protease cleavage site then removes the inhibitory endodomain from the target CAR, "switching-on" the potential for target receptor mediated T cell activation.

The inhibitory endodomain may, for example, comprise a CD148 or CD45 endodomain or an ITIM-containing endodomain from a protein such a PD1, PDCD1, BTLA4, LILRB1, LAIR1, CTLA4, KIR2DL1, KIR2DL4, KIR2DL5, KIR3DL1 or KIR3DL3.

By way of example, the target receptor may comprise the sequence shown as SEQ ID NO: 56, which contains a CAR against CD33 containing an ITIM endodomain from PD-1.

SEQ ID NO: 56
MAVPTQVLGLLLLWLTDARCDIQMTQSPSSLSASVGDRVTITCRASEDIY

FNLVWYQQKPGKAPKLLIYDTNRLADGVPSRFSGSGSGTQYTLTISSLQP

EDFATYYCQHYKNYPLTFGQGTKLEIKRSGGGGSGGGGSGGGGSGGGGSR

SEVQLVESGGGLVQPGGSLRLSCAASGFTLSNYGMHWIRQAPGKGLEWVS

SISLNGGSTYYRDSVKGRFTISRDNAKSTLYLQMNSLRAEDTAVYYCAAQ

DAYTGGYFDYWGQGTLVTVSSMDPATTTKPVLRTPSPVHPTGTSQPQRPE

DCRPRGSVKGTGLDFACDIYVGVVGGLLGSLVLLVWVLAVICSRAARGTI

GARRTGQPLKEDPSAVPVFSVDYGELDFQWREKTPEPPVPCVPEQTEYAT

IVFPSGMGTSSPARRGSADGPRSAQPLRPEDGHCSWPL

Suitably, the protein may comprise the sequence shown as SEQ ID NO: 56; or a variant thereof having at least 80, 85, 90, 95, 98 or 99% sequence identity.

Where the receptor comprises a protease cleavage site between a transmembrane domain and an activating endodomain, the castration signal fusion protein may be used to inhibit the receptor. For instance, a first CAR might be constructed whereby its endodomain is separated from the transmembrane domain by a protease cleavage site. A second CAR recognizing a different antigen might comprise of an ITIM containing endodomain. Recognition of the cognate antigen of the second receptor would result in recruitment of the castration signal fusion protein to the membrane and subsequent cleavage at the protease recognition site. Such cleavage would separate the activating endodomain from the first receptor and prevent activation and signal propagation from said receptor.

This would result in an "AND NOT" type logic gate where a sustained signal would be transmitted only if the first CAR was activated in isolation (i.e. when the first CAR bound its cognate antigen but the second CAR did not bind its cognate antigen). Such 'logic gates' may be useful, for example, because it is relatively rare for the presence (or absence) of a single antigen to effectively describe a cancer, which can lead to a lack of specificity. Targeting antigen expression on normal cells leads to on-target, off-tumour toxicity. In some cancers, a tumour is best defined by presence of one antigen (typically a tissue-specific antigen) and the absence of another antigen which is present on normal cells. For example, acute myeloid leukaemia (AML) cells express CD33. Normal stem cells express CD33 but also express CD34, while AML cells are typically CD34 negative. Targeting CD33 alone to treat AML is associated with significant toxicity as it depletes normal stem cells. However, specifically targeting cells which are CD33 positive but not CD34 positive would avoid this considerable off-target toxicity.

Potential pairs of antigens for such an 'AND NOT' gate are shown in Table 2.

TABLE 2

| Disease | TAA | Normal cell which expresses TAA | Antigen expressed by normal cell but not cancer cell |
|---|---|---|---|
| AML | CD33 | stem cells | CD34 |
| Myeloma | BCMA | Dendritic cells | CD1c |
| B-CLL | CD160 | Natural Killer cells | CD56 |
| Prostate cancer | PSMA | Neural Tissue | NCAM |
| Bowel cancer | A33 | Normal bowel epithelium | HLA class I |

By way of example, the receptor which comprises a protease cleavage site between a transmembrane domain and an activating endodomain may be the sequence shown as SEQ ID NO: 57, which contains a CAR against CD19 with a cleavable CD3-zeta endodomain.

SEQ ID NO: 57
MSLPVTALLLPLALLLHAARPDIQMTQTTSSLSASLGDRVTISCRASQDI

SKYLNWYQQKPDGTVKLLIYHTSRLHSGVPSRFSGSGSGTDYSLTISNLE

QEDIATYFCQQGNTLPYTFGGGTKLEITKAGGGGSGGGGSGGGGSGGGGS

EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSSDPTTTPAPRPPTPAPTIASQPLSLRPEACR

PAAGGAVHTRGLDFACDIFWVLVVVGGVLACYSLLVTVAFIIFWVRCRHR

RRQAERMAQIKRVVSEKKTAQAPHRFQKTCSPISGGGGSENLYFQMRRVK

FSRSADAPAYQQGQNQLYNELNLGRREEYDVLDKRRGRDPEMGGKPRRKN

PQEGLYNELQKDKMAEAYSEIGMKGERRRGKGHDGLYQGLSTATKDTYDA

LHMQALPPR

Suitably, the receptor may comprise the sequence shown as SEQ ID NO: 57; or a variant thereof having at least 80, 85, 90, 95, 98 or 99% sequence identity.

Where the receptor comprises an activating endodomain fused to an inhibitory endodomain via a protease cleavage site, a castration signal fusion protein can be used to activate artificial signalling domains. For instance, a first CAR might be constructed whereby its endodomain comprises an activating endodomain fused to an inhibitory endodomain via a protease cleavage site. A second CAR recognizing a different antigen might comprise of an ITIM containing endodomain. Recognition of the cognate antigen of the second receptor would result in recruitment of the castration signal fusion protein to the membrane and subsequent cleavage of inhibitory endodomain from the activating endodomain of the first receptor. Cleavage, and thus separation, of the inhibitory domain from the activating domain would allow activation of the first CAR following antigen binding and hence activation of signalling via the first receptor.

This would result in an "AND" type CAR logic gate where productive signalling would occur only if both the first and second receptors were activated. Such 'logic gates' are useful, for example, because most cancers cannot be differentiated from normal tissues on the basis of a single antigen. Hence, considerable "on-target off-tumour" toxicity occurs whereby normal tissues are damaged by the therapy. For some cancers, targeting the presence of two cancer antigens may be more selective and therefore effective than targeting one. For example, B-chronic lymphocytic leukaemia (B-CLL) is a common leukaemia which is currently treated by targeting CD19. This treats the lymphoma but also depletes the entire B-cell compartment such that the treatment has a considerable toxic effect. B-CLL has an unusual phenotype in that CD5 and CD19 are co-expressed. By targeting only cells which express CD5 and CD19, it would be possible to considerably reduce on-target off-tumour toxicity.

Potential pairs of antigens for such an 'AND' logic gate are shown in Table 3.

TABLE 3

| Cancer Type | Antigens |
|---|---|
| Chronic Lymphocytic Leukaemia | CD5, CD19 |
| Neuroblastoma | ALK, GD2 |
| Glioma | EGFR, Vimentin |
| Multiple myeloma | BCMA, CD138 |
| Renal Cell Carcinoma | Carbonic anhydrase IX, G250 |
| T-ALL | CD2, N-Cadherin |
| Prostate Cancer | PSMA, hepsin (or others) |

By way of example, the receptor which comprises an activating endodomain fused to an inhibitory endodomain via a protease cleavage site may be the sequence shown as SEQ ID NO: 58, which contains a CAR against CD19 with a CD3-zeta endodomain and a cleavable CD148 endodomain.

SEQ ID NO: 58
MSLPVTALLLPLALLLHAARPDIQMTQTTSSLSASLGDRVTISCRASQDI

SKYLNWYQQKPDGTVKLLIYHTSRLHSGVPSRFSGSGSGTDYSLTISNLE

QEDIATYFCQQGNTLPYTFGGGTKLEITKAGGGGSGGGGSGGGGSGGGGS

EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSSDPTTTPAPRPPTPAPTIASQPLSLRPEACR

-continued

```
PAAGGAVHTRGLDFACDIFWVLVVVGGVLACYSLLVTVAFIIFWVRRVKF

SRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDAL

HMQALPPRENLYFQMAVFGCIFGALVIVTVGGFIFWRKKRKDAKNNEVSF

SQIKPKKSKLIRVENFEAYFKKQQADSNCGFAEEYEDLKLVGISQPKYAA

ELAENRGKNRYNNVLPYDISRVKLSVQTHSTDDYINANYMPGYHSKKDFI

ATQGPLPNTLKDFWRMVWEKNVYAIIMLTKCVEQGRTKCEEYWPSKQAQD

YGDITVAMTSEIVLPEWTIRDFTVKNIQTSESHPLRQFHFTSWPDHGVPD

TTDLLINFRYLVRDYMKQSPPESPILVHCSAGVGRTGTFIAIDRLIYQIE

NENTVDVYGIVYDLRMHRPLMVQTEDQYVFLNQCVLDIVRSQKDSKVDLI

YQNTTAMTIYENLAPVTTFGKTNGYIA
```

Suitably, the receptor may comprise the sequence shown as SEQ ID NO: 58; or a variant thereof having at least 80, 85, 90, 95, 98 or 99% sequence identity.

Blocking Signal

The present invention provides a truncated protein which comprises an SH2 domain from a protein which binds a phosphorylated immunoreceptor tyrosine-based activation motif (ITAM) but lacks a kinase domain For example, the truncated protein may comprise the ZAP70 SH2 domain but lack the ZAP70 kinase domain. In other words, the present invention provides a truncated protein which: (i) comprises the sequence shown as SEQ ID NO: 2 but does not comprise the sequence shown as SEQ ID NO: 26.

Over-expression of the ZAP70 SH2 domain results in competition with full-length/wild-type ZAP70. Since the truncated ZAP70 cannot propagate signals, signal transmission is reduced in proportion to the ratio between wild-type ZAP70 and the truncated protein. This may be useful to reduce strength of T-cell activation for instance to prevent T-cell over-activation which can result in T-cell exhaustion, activation induced cell death and in a clinical setting can result in cytokine storms.

The present invention also provide a truncated protein which comprises an SH2 domain from a protein which binds a phosphorylated immunoreceptor tyrosine-based inhibition motif (ITIM) but lacks a phosphatase domain For example, the truncated protein may comprise the PTPN6 SH2 domain but lack the PTPN6 phosphatase domain. In other words, the present invention provides a truncated protein which: (i) comprises the sequence shown as SEQ ID NO: 6 but does not comprise the sequence shown as SEQ ID NO: 27.

In this case, ITIM signalling can be reduced in proportion to the ratio between wild-type PTPN6 and the truncated protein. This may be useful to reduce inhibitory signals such as PD1 signalling. This may have application when T-cells are targeting a tumour which over-expresses PDL1 (or similar inhibitory receptors) to evade immune rejection.

The use of a blocking signal or a cross-wire signal as described above, offers a significant advantage over traditional immune checkpoint blockade approaches which typically block a single ligand/receptor interaction, such as PD-L1/PD1, with an antibody. As explained above, the inhibitory immune receptor class contains many members with redundancies and expression patterns which fluctuate with T-cell state. The use of an antibody or a recombinant ligand/receptor may effectively block one inhibitory receptor, but will not affect inhibitory signals transmitted from the rest. Genomic editing of individual inhibitory receptors (Menger et al, Cancer Res. 2016 Apr. 15; 76(8):2087-93) has a similar limitation. Strategies of fusions between individual inhibitory receptors and co-stimulatory domains also suffer from similar limitations (Liu et al, Cancer Res. 2016 Mar. 15; 76(6):1578-90).

The method of the present invention will block (and depending on the strategy re-interpret) inhibitory signals transmitted via an ITIM. Hence an entire class of inhibitory signals are modulated. A list of inhibitory receptors which signal through ITIMs is provided in Table II of Odorizzi and Wherry (2012) J. Immunol. 188:2957-2965. They include: PD1, BTLA, 2B4, CTLA-4, GP49B, Lair-1, Pir-B, PECAM-1, CD22, Siglec 7, Siglec 9, KLRG1, ILT2, CD94-NKG2A and CD5.

Nucleic Acid

In one aspect the present invention provides a nucleic acid which encodes a fusion protein or a truncated protein according to the present invention.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

Nucleic Acid Construct

In one aspect the present invention provides a nucleic acid construct which co-expresses a truncated protein or fusion protein of the present invention with another protein. The nucleic acid construct may comprise: a nucleic acid sequence encoding a truncated protein or a fusion protein of the present invention; and a nucleic acid encoding another protein.

The present invention provides a nucleic acid construct which co-expresses a truncated protein or fusion protein of the present invention with a chimeric antigen receptor. The nucleic acid construct may comprise: (i) a nucleic acid sequence encoding a truncated protein or a fusion protein of the present invention; and (ii) a nucleic acid encoding a chimeric antigen receptor.

The chimeric antigen receptor (CAR) may be an activatory CAR comprising an ITAM-containing endodomain, such as CD3 zeta. The CAR may be an inhibitory CAR comprising a "ligation-off" endodomain, as described in WO2015/075469 which may comprise all or part of the endodomain from a receptor-like tyrosine phosphatase, such as CD148 or CD45. The CAR may be an inhibitory CAR comprising a "ligation-on" endodomain, as described in WO2015/075470 which may comprise an ITIM domain.

The fusion proteins and truncated proteins of the invention may be used together with a cell expressing a "logic gate" combination of two or more CARs. An OR gate comprises two activatory CARs as described in WO2015/075468. An AND gate comprises an activatory CAR and a "ligation off" inhibitory CAR, as described in WO2015/075469. An AND not comprises an activatory CAR and a "ligation on" inhibitory CAR, as described in WO2015/075470.

Thus the present invention provides a nucleic acid construct which comprises:
(i) a nucleic acid sequence encoding a truncated protein or fusion protein of the invention;
(ii) a first chimeric antigen receptor (CAR); and
(iii) a second chimeric antigen receptor.

With reference to the transcription signal aspect of the invention, there is provided a nucleic acid construct which comprises (i) a nucleic acid sequence encoding a fusion protein comprising a SH2 domain; and a protease domain; and (ii) a nucleic acid sequence encoding a membrane tethered transcription factor which comprises: a membrane tether; a protease recognition site; and a transcription factor.

With reference to the castration signal aspect of the invention, there is provided a nucleic acid construct which comprises (i) a nucleic acid sequence encoding a fusion protein which comprises an SH2 domain and a protease domain (e.g. a TeV domain); and (ii) a nucleic acid sequence encoding a receptor which comprises a protease cleavage site.

For example, the present invention provides a nucleic acid construct which comprises: (a) a nucleic acid sequence encoding a fusion protein which comprises (i) PTPN6 SH2 domain; and (ii) a protease domain (e.g. a TeV domain); (b) a nucleic acid sequence encoding a receptor which comprises a protease cleavage site; and (c) a nucleic acid sequence encoding a receptor comprising an ITIM containing endodomain.

The receptor may be a T-cell receptor (TCR) or a chimeric antigen receptor (CAR).

Suitably, the protein encoded by nucleic acid sequence (b) may be a T-cell receptor (TCR) or a chimeric antigen receptor (CAR) which comprises: (i) a protease cleavage site between a transmembrane domain and an activating endodomain; or (ii) an activating endodomain fused to an inhibitory endodomain via a protease cleavage site.

Where the nucleic acid construct of the invention, produces discrete polypeptides, such when it coexpresses a fusion protein of the invention and a CAR, it may also comprise a nucleic acid sequence enabling expression of both proteins. For example, it may comprise a sequence encoding a cleavage site between the two nucleic acid sequences. The cleavage site may be self-cleaving, such that when the nascent polypeptide is produced, it is immediately cleaved into the two proteins without the need for any external cleavage activity.

Various self-cleaving sites are known, including the Foot-and-Mouth disease virus (FMDV) 2a self-cleaving peptide, which has the sequence shown:

RAEGRGSLLTCGDVEENPGP    SEQ ID NO: 59 or

QCTNYALLKLAGDVESNPGP    SEQ ID NO: 60

The co-expressing sequence may be an internal ribosome entry sequence (IRES). The co-expressing sequence may be an internal promoter.

Chimeric Antigen Receptor (CAR)

Figure 13:
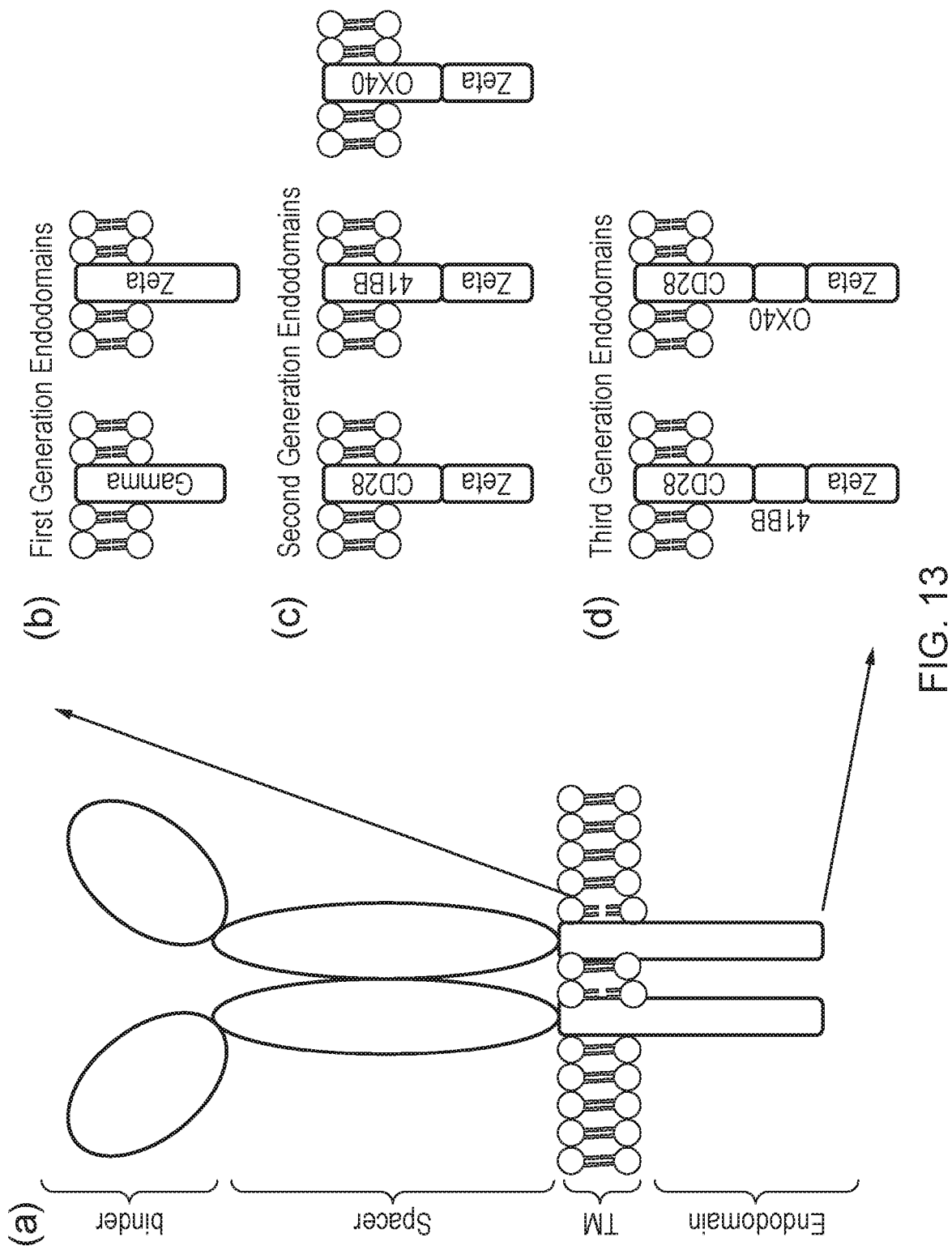
FIG. 13—(a) Generalized architecture of a CAR: A binding domain recognizes antigen; the spacer elevates the binding domain from the cell surface; the trans-membrane domain anchors the protein to the membrane and the endodomain transmits signals. (b) to (d): Different generations and permutations of CAR endodomains: (b) initial designs transmitted ITAM signals alone through FcεR1-γ or CD3ζ endodomain, while later designs transmitted additional (c) one or (d) two co-stimulatory signals in cis.

CARs, which are shown schematically in FIG. 13, are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A common spacer domain used is the Fc of IgG1. More compact spacers can suffice e.g. the stalk from CD8α and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

CAR-encoding nucleic acids may be transferred to T cells using, for example, retroviral vectors. Lentiviral vectors may be employed. In this way, a large number of cancer-specific T cells can be generated for adoptive cell transfer. When the CAR binds the target-antigen, this results in the transmission of an activating signal to the T-cell it is expressed on. Thus the CAR directs the specificity and cytotoxicity of the T cell towards tumour cells expressing the targeted antigen.

CARs typically therefore comprise: (i) an antigen-binding domain; (ii) a spacer; (iii) a transmembrane domain; and (iii) an intracellular domain which comprises or associates with a signalling domain.

Antigen Binding Domain

The antigen binding domain is the portion of the CAR which recognizes antigen. Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain antibody; an artificial single binder such as a Darpin (designed ankyrin repeat protein); or a single-chain derived from a T-cell receptor.

The antigen binding domain may comprise a domain which is not based on the antigen binding site of an antibody. For example the antigen binding domain may comprise a domain based on a protein/peptide which is a soluble ligand for a tumour cell surface receptor (e.g. a soluble peptide such as a cytokine or a chemokine); or an extracellular domain of a membrane anchored ligand or a receptor for which the binding pair counterpart is expressed on the tumour cell.

The antigen binding domain may be based on a natural ligand of the antigen.

The antigen binding domain may comprise an affinity peptide from a combinatorial library or a de novo designed affinity protein/peptide.

Spacer Domain

CARs comprise a spacer sequence to connect the antigen-binding domain with the transmembrane domain and spatially separate the antigen-binding domain from the endodomain. A flexible spacer allows the antigen-binding domain to orient in different directions to facilitate binding.

In aspects of the present invention which require two CARs, the first and second CARs may comprise different spacer molecules. For example, the spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

All the spacer domains mentioned above form homodimers. However the mechanism is not limited to using homodimeric receptors and should work with monomeric receptors as long as the spacer is sufficiently rigid. An example of such a spacer is CD2 or truncated CD22.

Since CARs are typically homodimers (see FIG. 13a), cross-pairing may result in a heterodimeric chimeric antigen receptor. This is undesirable for various reasons, for example: (1) the epitope may not be at the same "level" on the target cell so that a cross-paired CAR may only be able to bind to one antigen; (2) the VH and VL from the two different scFv could swap over and either fail to recognize target or worse recognize an unexpected and unpredicted antigen. For the "AND" and "AND NOT" gates described above, the spacer of the first CAR may be sufficiently different from the spacer of the second CAR in order to avoid cross-pairing but sufficiently similar to co-localise. Pairs of orthologous spacer sequences may be employed. Examples are murine and human CD8 stalks, or alternatively spacer domains which are monomeric—for instance the ectodomain of CD2.

Examples of spacer pairs which co-localise are shown in the following Table:

| Stimulatory CAR spacer | Inhibitory CAR spacer |
| --- | --- |
| Human-CD8aSTK | Mouse CD8aSTK |
| Human-CD28STK | Mouse CD8aSTK |
| Human-IgG-Hinge | Human-CD3z ectodomain |
| Human-CD8aSTK | Mouse CD28STK |
| Human-CD28STK | Mouse CD28STK |
| Human-IgG-Hinge-CH2CH3 | Human-IgM-Hinge-CH2CH3CD4 |

Transmembrane Domain

The transmembrane domain is the sequence of the CAR that spans the membrane.

A transmembrane domain may be any protein structure which is thermodynamically stable in a membrane. This is typically an alpha helix comprising of several hydrophobic residues. The transmembrane domain of any transmembrane protein can be used to supply the transmembrane portion of the invention. The presence and span of a transmembrane domain of a protein can be determined by those skilled in the art using the TMHMM algorithm (http://www.cbs.dtu.dk/services/TMHMM-2.0/). Further, given that the transmembrane domain of a protein is a relatively simple structure, i.e a polypeptide sequence predicted to form a hydrophobic alpha helix of sufficient length to span the membrane, an artificially designed TM domain may also be used (U.S. Pat. No. 7,052,906 B1 describes synthetic transmembrane components).

The transmembrane domain may be derived from CD28, which gives good receptor stability.

Activating Endodomain

The endodomain is the signal-transmission portion of the CAR. It may be part of or associate with the intracellular domain of the CAR. After antigen recognition, receptors cluster, native CD45 and CD148 are excluded from the synapse and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signaling may be needed. For example, chimeric CD28 and OX40 can be used with CD3-Zeta to transmit a proliferative/survival signal, or all three can be used together.

Where a CAR comprises an activating endodomain, it may comprise the CD3-Zeta endodomain alone, the CD3-Zeta endodomain with that of either CD28 or OX40 or the CD28 endodomain and OX40 and CD3-Zeta endodomain.

Any endodomain which contains an ITAM motif can act as an activation endodomain in this invention. Suitable endodomains which contain an ITAM motif are described herein.

Inhibitory Domain

In embodiments referred to above as the "AND" gate, the first CAR may comprise an activating endodomain fused to an inhibitory endodomain via a protease cleavage site. As such the inhibitory endodomain inhibits T-cell activation by the first CAR in the absence of activation of the second CAR. Upon activation of the second CAR, the ITIM in the endodomain of the second CAR is phosphorylated and the PTPN6/protease domain fusion protein is recruited to the membrane. This results in cleavage of the first CAR between the activating endodomain and inhibitory endodomain, thus enabling T-cell activation.

The inhibitory endodomains may comprise any sequence which inhibits T-cell signalling by the activating CAR when it is in the same endodomain.

The inhibitory endodomain may be or comprise a tyrosine phosphatase, such as a receptor-like tyrosine phosphatase. An inhibitory endodomain may be or comprise any tyrosine phosphatase that is capable of inhibiting the TCR signalling when co-localised with the activating endodomain of the CAR. An inhibitory endodomain may be or comprise any tyrosine phosphatase with a sufficiently fast catalytic rate for phosphorylated ITAMs that is capable of inhibiting the TCR signalling when co-localised with the activating endodomain of the CAR.

Vector

The present invention also provides a vector, or kit of vectors which comprises one or more nucleic acid sequence(s) or construct(s) according to the present invention. Such a vector may be used to introduce the nucleic acid sequence(s) or construct(s) into a host cell so that it expresses the proteins encoded by the nucleic acid sequence or construct.

The vector may, for example, be a plasmid or a viral vector, such as a retroviral vector or a lentiviral vector, or a transposon based vector or synthetic mRNA.

The vector may be capable of transfecting or transducing a T cell.

Cell

The present invention also relates to an immune cell comprising the fusion protein, truncated protein, nucleic acid and/or nucleic acid construct of the present invention.

The cell may be a cytolytic immune cell.

Cytolytic immune cells can be T cells or T lymphocytes which are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

Natural Killer Cells (or NK cells) are a type of cytolytic cell which form part of the innate immune system. NK cells provide rapid responses to innate signals from virally infected cells in an MHC independent manner.

NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The cells of the invention may be any of the cell types mentioned above.

T or NK cells expressing the molecules of the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, T or NK cells expressing the molecules of the invention may be derived from ex vivo differentiation of inducible progenitor cells or embryonic progenitor cells to T cells. Alternatively, an immortalized T-cell line which retains its lytic function and could act as a therapeutic may be used.

In all these embodiments, cells are generated by introducing DNA or RNA coding for the receptor component and signalling component by one of many means including transduction with a viral vector, transfection with DNA or RNA.

The cell of the invention may be an ex vivo T or NK cell from a subject. The T or NK cell may be from a peripheral blood mononuclear cell (PBMC) sample. T or NK cells may be activated and/or expanded prior to being transduced with nucleic acid of the invention, for example by treatment with an anti-CD3 monoclonal antibody.

The T or NK cell of the invention may be made by:
 (i) isolation of a T or NK cell-containing sample from a subject or other sources listed above; and
 (ii) transduction or transfection of the T or NK cells with one or more a nucleic acid sequence(s) according to the invention.

The T or NK cells may then by purified, for example, selected on the basis of expression of the antigen-binding domain of the antigen-binding polypeptide.

The present invention also provides a cell which comprises a fusion protein or a truncated protein of the invention and a chimeric antigen receptor (CAR).

The chimeric antigen receptor (CAR) may be an activatory CAR comprising an ITAM-containing endodomain, such as CD3 zeta. The CAR may be an inhibitory CAR comprising a "ligation-off" endodomain, as described in WO2015/075469 which may comprise all or part of the endodomain from a receptor-like tyrosine phosphatase, such as CD148 or CD45. The CAR may be an inhibitory CAR comprising a "ligation-on" endodomain, as described in WO2015/075470 which may comprise an ITIM domain.

The fusion proteins and truncated proteins of the invention may be used together with a cell expressing a "logic gate" combination of two or more CARs. An OR gate comprises two activatory CARs as described in WO2015/075468. An AND gate comprises an activatory CAR and a "ligation off" inhibitory CAR, as described in WO2015/075469. An AND not comprises an activatory CAR and a "ligation on" inhibitory CAR, as described in WO2015/075470.

Thus the present invention provides a cell which comprises:
(i) a nucleic acid sequence encoding a truncated protein or fusion protein of the invention;
(ii) a first chimeric antigen receptor (CAR); and
(iii) a second chimeric antigen receptor.

With reference to the transcription signal aspect of the invention, there is provided a cell which comprises (i) a fusion protein comprising an SH2 domain and a protease; and (ii) a membrane tethered transcription factor which comprises: a membrane tether, a protease recognition site; and a transcription factor.

With reference to the castration signal aspect of the invention there is provided a cell which comprises (i) a fusion protein comprising an SH2 domain and a protease; and (ii) receptor which comprises a protease cleavage site.

The receptor may, for example be a T-cell receptor (TCR) or a chimeric antigen receptor (CAR) which comprises: (i) a protease cleavage site between a transmembrane domain and an activating endodomain; or (ii) an activating endodomain fused to an inhibitory endodomain via a protease cleavage site.

Composition

The present invention also relates to a pharmaceutical composition containing a plurality of cells of the invention. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The cells of the present invention may be capable of killing target cells, such as cancer cells.

The cells of the present invention may be used for the treatment of an infection, such as a viral infection.

The cells of the invention may also be used for the control of pathogenic immune responses, for example in autoimmune diseases, allergies and graft-vs-host rejection.

The cells of the invention may be used for the treatment of a cancerous disease, such as bladder cancer, breast cancer, colon cancer, endometrial cancer, kidney cancer (renal cell), leukemia, lung cancer, melanoma, non-Hodgkin lymphoma, pancreatic cancer, prostate cancer and thyroid cancer.

The cells of the invention may be used to treat: cancers of the oral cavity and pharynx which includes cancer of the tongue, mouth and pharynx; cancers of the digestive system which includes oesophageal, gastric and colorectal cancers; cancers of the liver and biliary tree which includes hepatocellular carcinomas and cholangiocarcinomas; cancers of the respiratory system which includes bronchogenic cancers and cancers of the larynx; cancers of bone and joints which includes osteosarcoma; cancers of the skin which includes melanoma; breast cancer; cancers of the genital tract which include uterine, ovarian and cervical cancer in women, prostate and testicular cancer in men; cancers of the renal tract which include renal cell carcinoma and transitional cell carcinomas of the utterers or bladder; brain cancers including gliomas, glioblastoma multiforme and medullobastomas; cancers of the endocrine system including thyroid cancer, adrenal carcinoma and cancers associated with multiple endocrine neoplasm syndromes; lymphomas including Hodgkin's lymphoma and non-Hodgkin lymphoma; Multiple Myeloma and plasmacytomas; leukaemias both acute and chronic, myeloid or lymphoid; and cancers of other and unspecified sites including neuroblastoma.

Treatment with the cells of the invention may help prevent the escape or release of tumour cells which often occurs with standard approaches.

The invention will now be further described by way of Examples, which are meant to serve to assist one of ordinary skill in the art in carrying out the invention and are not intended in any way to limit the scope of the invention.

EXAMPLES

Example 1—Subjugation of the T Cell Activation Pathway to Augmented or Non-Physiological Signals A number of SH2 domains involved in early T cell signal activation were tested to determine whether T cell activation signals could be subjugated or "hijacked", such that when a T cell was activated the signal could be modulated or re-transmitted.

Figure 8:
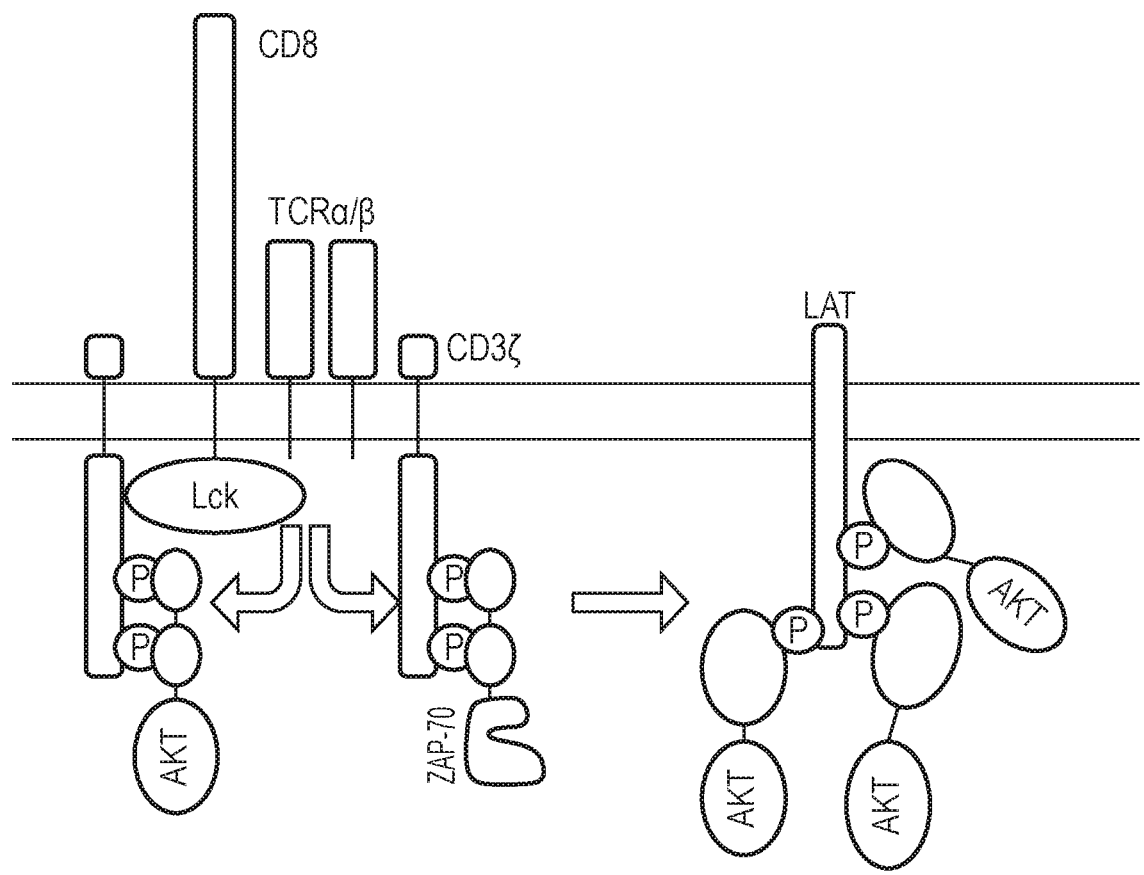
FIG. 8—Several fusions of different SH2 domains and AKT kinase domain were constructed: ZAP-AKT, GRAP-AKT, GRB-AKT and PLC-γ.

The inventors generated several chimeric AKT constructs by linking the kinase domain of AKT to SH2 domains from Zap70, Grap, Grb2 and PLCγ (FIG. 8).

In non-transduced (NT) T cells, very low levels of phosphorylation of the endogenous AKT were detectable following treatment with OKT3 to induce cross-linking and activation of the TCR (FIG. 10b:top panel). However, in cells expression the Zap-AKT construct, significant levels of phospho-AKT were observed (FIG. 10b:bottom panel).

Linker for activation of T cell (LAT) is a downstream target of ZAP70 and is bound by several SH2-containing proteins, such as Grb2, Grap and PLCγ. It was anticipated that the SH2 domains from each of these LAT-binders would also allow the activation signal from CD3-zeta to be hijacked. However, this was not the case.

Figure 9:
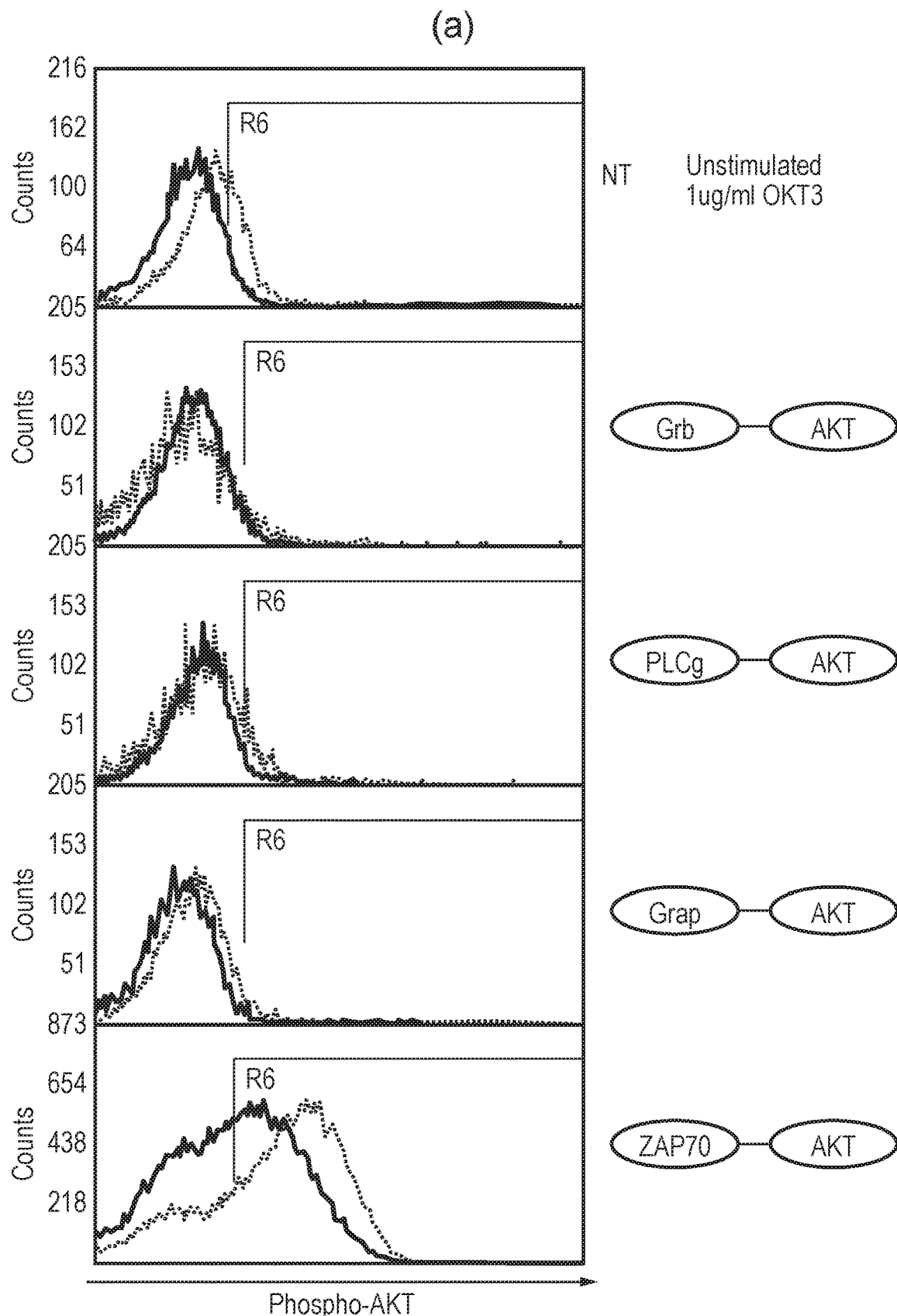
FIG. 9—(a) Phospho-AKT staining of T-cells transduced with the different SH2/AKT fusions with and without activation with the mitogenic antibody OKT3. (b) Phospho-AKT staining of T-cells transduced with ZAP-AKT fusion, an improved ZAP-AKT fusion where ZAP and AKT are connected via a flexible linker, and a control ZAP-AKT where R190K substitution removes ability of ZAP to bind ITAMs. T-cells were either stimulated with OKT3 or not-stimulated with OKT3. The facs plots are overlaid over that of non-transduced T-cells.
Figure 9:
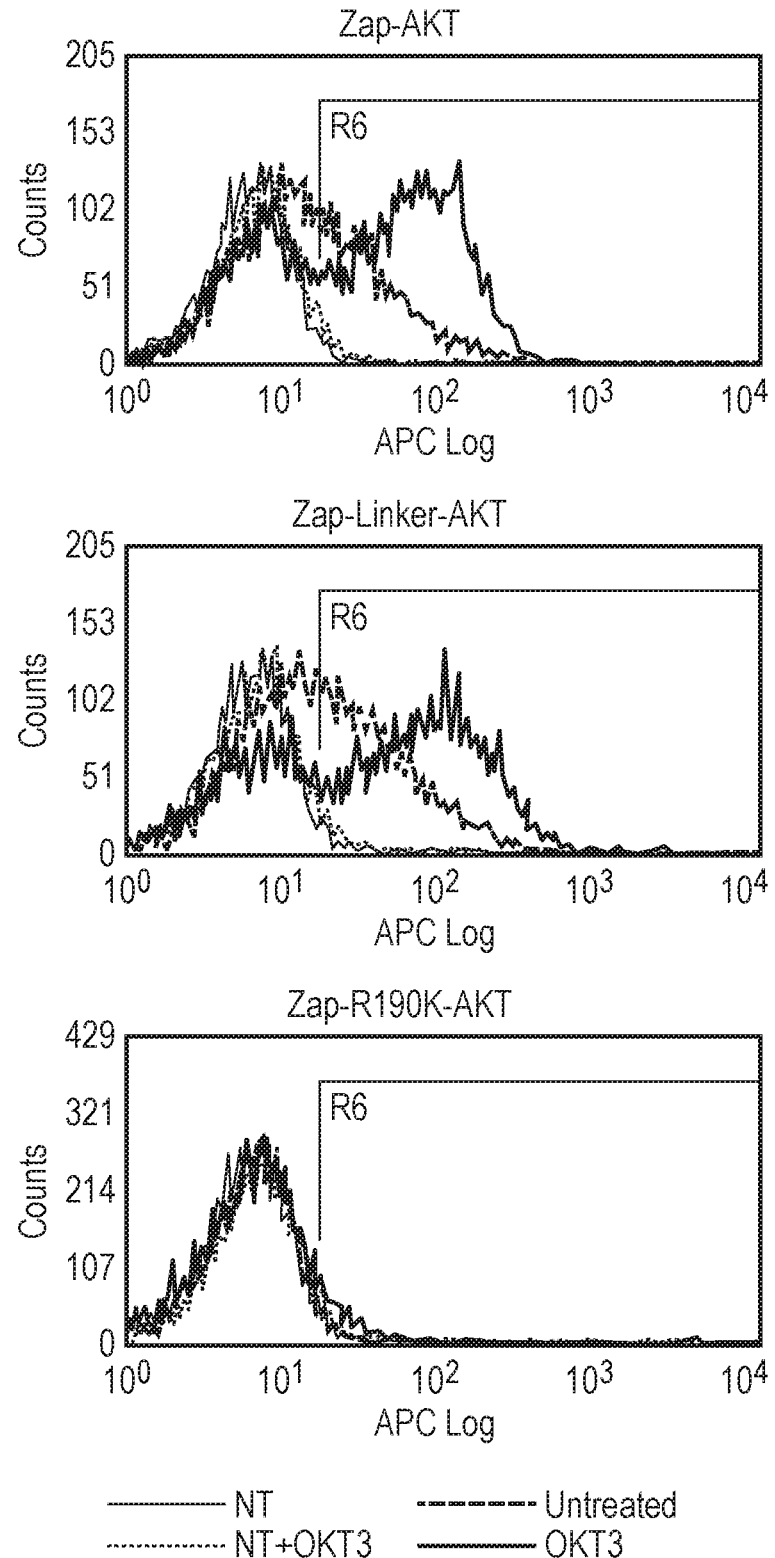

No TCR-dependent phosphorylation of the AKT kinase domain was observed above levels observed for NT T cells when the AKT kinase domain was linked to the SH2 domains from Grb2, Grap or PLCγ (FIG. 9a).

This demonstrates that this system of T cell signalling hijacking specifically requires the tandem SH2 domain from a very early T cell signalling molecule, such as Zap70 or Tyrosine-protein phosphatase non-receptor type 6 (PTPN6).

Example 2—Transcriptional Control

The TeV protease was fused to the Zap70 SH2 domain. A membrane-bound transcription factor was also generated as follows: RQR8 was cloned in frame with the VP16/GAL4 transcription factor separated by a TeV cleavage site. This fusion protein allows release of the VP16/GAL4 transcription factor (which contains a nuclear localizing signal) upon TeV cleavage.

These proteins were both expressed in a T-cell which also expressed a CD19-specific chimeric antigen receptor. To demonstrate that the ZAP70-TeV approach is needed, the transcription factor was co-expressed with a CD19 CAR whose endodomain was replaced by TeV (FIG. 11).

Figure 12:
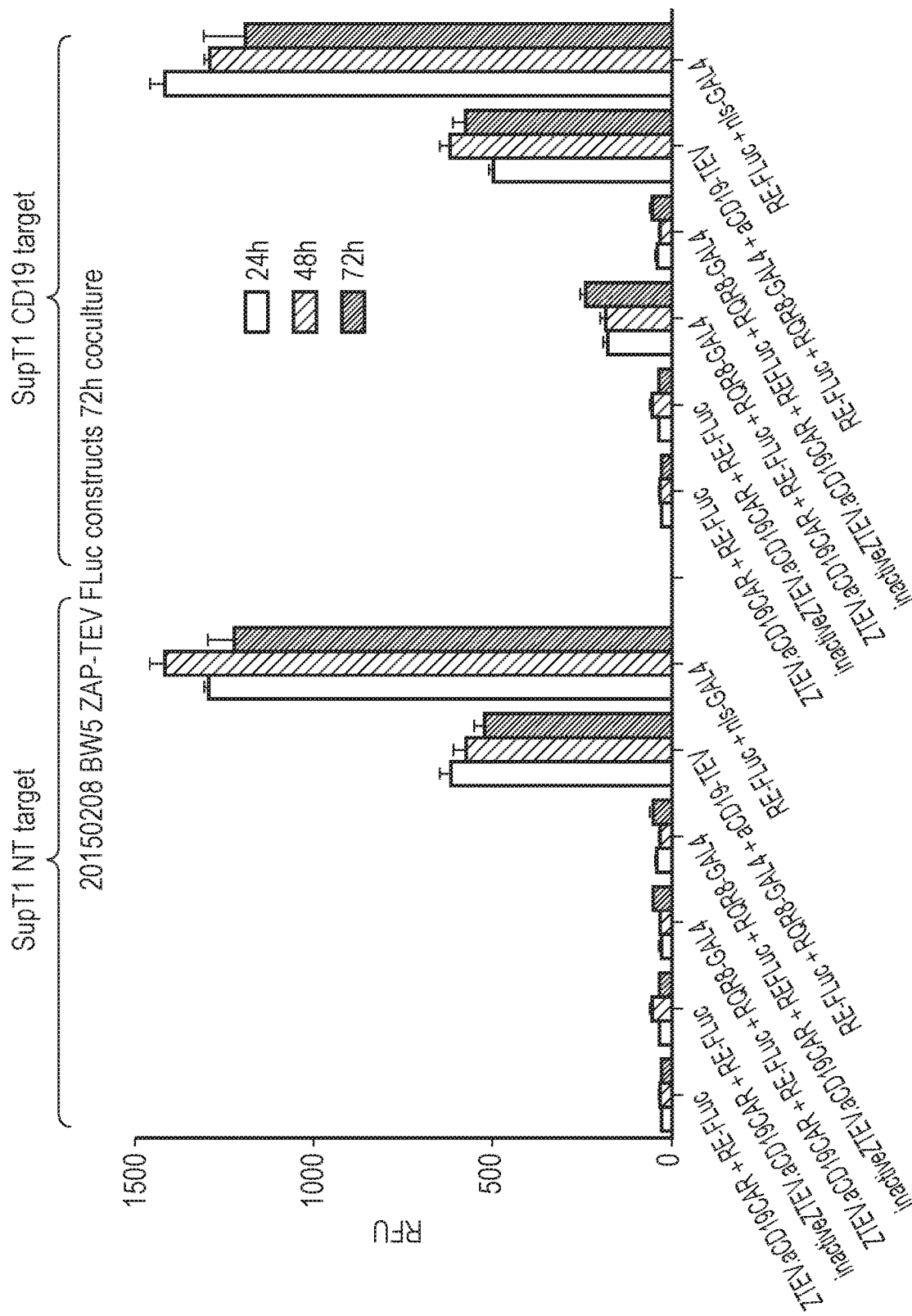
FIG. 12—Activity of ZAP-TeV based transcriptional switches and control expressing T-cells after exposure to CD19 negative (left), or CD19 positive (right) targets. Activity is measured by light output after adding Luciferase. In order the conditions tested are: (a) aCD19 CAR co-expressed with ZAP-TeV; (b) aCD19 CAR co-expressed with inactive (R190K); (c) aCD19 CAR co-expressed with ZAP-TeV and the membrane tethered transcription factor; (d) aCD19 CAR co-expressed with inactive (R190K) ZAP-TEV co-expressed with the membrane tethered transcription factor; (e) aCD19 CAR/TeV fusion co-expressed with the membrane-tethered transcription factor; (f) constitutively active GAL4/VP16 transcription factor.

T-cells were exposed to CD19 negative and positive targets. Transcriptional activation was measured by a Luciferase cassette responsive to GALv/VP16. Only the condition where a standard CD19 CAR was co-expressed with ZAP-TeV and the membrane tethered transcription factor resulted in selective transcriptional activation upon CD19 recognition. The CD19 CAR fused directly to TeV resulted in constitutive transcriptional activation (FIG. 12).

Example 3—PD-1 Signal Blockade Using Truncated SHP-1 (PTPN6) or Truncated SHP-2

PBMC cells were transduced as shown in the following table:

| Name on FIG. 15 key | Description | Construct(s) |
|---|---|---|
| NT | Untransduced | — |
| FMC63 | Transduced with CD19 CAR only | SFG.aCD19_fmc63-HCH2CH3w-CD28tmZw |
| PD1 | Transduced with PD1 only | pDual-PD1-GFP |
| FMC63 + PD1 | Co-transduced with CD19CAR and PD1 | SFG.aCD19_fmc63-HCH2CH3w-CD28tmZw and pDual-PD1-GFP |
| FMC63 − SHP1 + PD1 | Co-transduced with a) bicistronic construct encoding CD19CAR and truncated SHP1, and b) PD1 | SFG.aCD19_fmc63-HCH2CH3w-CD28tm-Zeta_w-2A-dualSH2_SHP-1 and pDual-PD1-GFP |
| FMC63 − SHP2 + PD1 | Co-transduced with a) bicistronic construct encoding CD19CAR and truncated SHP1, b) PD1 | SFG.aCD19_fmc63-HCH2CH3w-CD28tm-Zeta_w-2A-dualSH2_SHP-2 and pDual-PD1-GFP |

The cells were co-cultured for 48 hours with SupT1 cells transduced with CD19, PDL1 or both and IFNγ release measured by ELISA. The results are shown in FIG. 15.

The presence of PDL1 on SupT1 target cells caused a reduction in IFNγ release. There was increased IFNγ release with PBMC which expressed CAR together with the truncated SHP-1 or truncated SHP-2 construct compared with those which expressed CAR alone. This indicates that the truncated SHp-1 and SHP-2 constructs successfully inhibited the PDL1 inhibitory signal from the target cells.

Example 4—PD-1 Signal Hijack Using a Fusion of SHP-2 SH2 Domains and Zap70 Kinase PBMC cells were transduced as shown in the following table:

| Name on FIG. 16 key | Description | Construct(s) |
|---|---|---|
| NT | Untransduced | — |
| FMC63 | Transduced with CD19 CAR only | SFG.aCD19_fmc63-HCH2CH3w-CD28tmZw |
| PD1 | Transduced with PD1 only | pDual-PD1-GFP |
| FMC63 + PD1 | Co-transduced with CD19CAR and PD1 | SFG.aCD19_fmc63-HCH2CH3w-CD28tmZw and pDual-PD1-GFP |
| FMC63 − SHP2Zap70 + PD1 | Co-transduced with a) bicistronic construct encoding CD19CAR and fusion of SHP2 SH2domains and Zap70 kinase, and b) PD1 | SFG.aCD19_fmc63-HCH2CH3w-CD28tm-Zeta_w-2A-dualSH2_SHP-2-Zap70_Kinase and pDual-PD1-GFP |

Figure 16A:
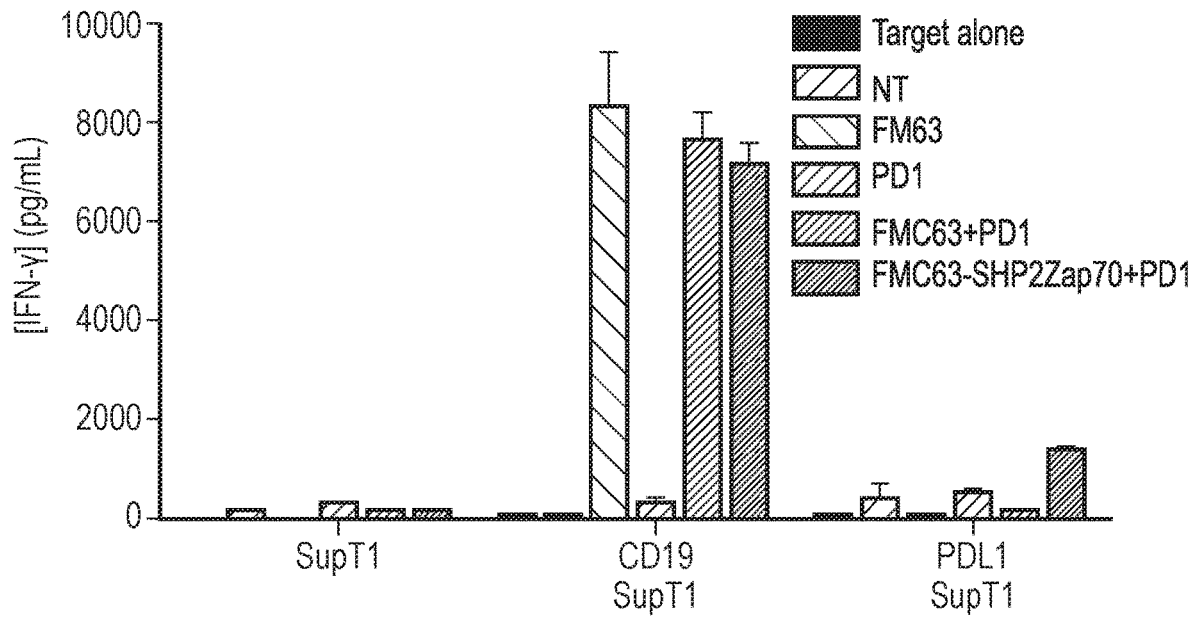
FIG. 16—PD-1 signal hijack using a fusion of SHP-2 SH2 domains and Zap70 kinase PBMC cells were cotransduced with PD1 and either CAR alone (FMC63); or a bicistronic construct containing CAR and a fusion protein comprising SHP-2 SH2 domains and the ZAP70 kinase. These cells were co-cultured in a 1:1 ratio for 24 hours with SupT1 cells transduced with CD19 or PDL1. IFNγ release was measured by ELISA (A) and killing of SupT1 cells was quantified by FACS (B).

The cells were co-cultured in a 1:1 ratio for 24 hours with SupT1 cells transduced with CD19 or PDL1. IFNγ release was measured by ELISA (FIG. 16A). An increase in IFN-γ production in was seen co-cultures of CAR-SHP2.Zap70+ PD1 transduced T cells with PDL1 SupT1 target cells compared with CAR+PD1 transduced T cells.

Figure 16B:
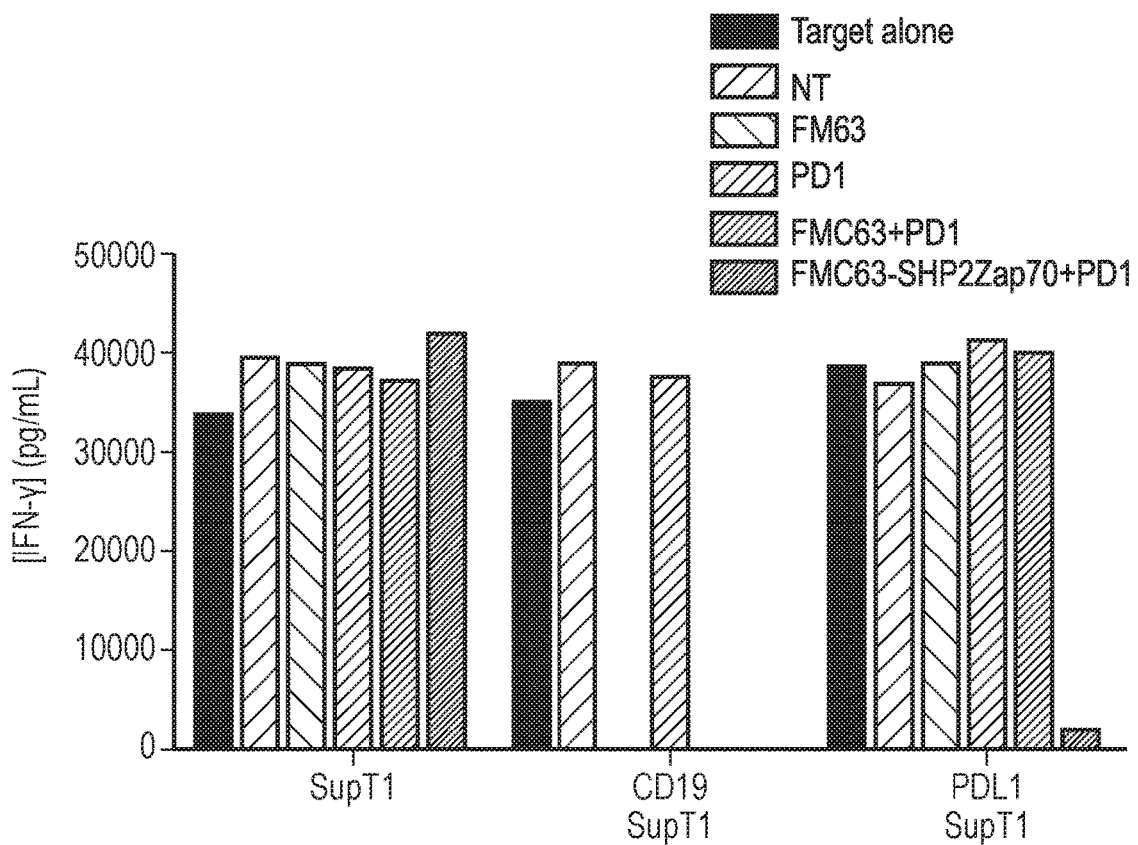

A cytotoxicity assay was also conducted in which killing of SupT1 cells was quantified by FACS (FIG. 16B). Near complete killing of PDL1 SupT1 targets was observed in co-cultures of PDL1 positive target cells with CAR-SHP2.Zap70+PD1 transduced T cells. By contrast, killing was not seen with CAR+PD1 alone construct. This indicated that replacing the phosphatase domain of SHP2 with the kinase domain of Zap70 successfully converted the inhibitory PD1 signal to an activatory signal. The SHP-2-Zap70 kinase fusion protein therefore successfully hijacked the inhibitory PDL1-PD1 signal and turned it into a T-cell activation signal.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

The invention claimed is:

1. An isolated T cell, which comprises a chimeric antigen receptor (CAR), wherein the T cell further comprises a SHP-2 domain lacking a SHP-2 phosphatase domain, and wherein the sequence of the SHP-2 domain is SEQ ID NO: 11 or SEQ ID NO: 12.

2. A nucleic acid construct, which comprises: a first nucleic acid sequence encoding a chimeric antigen receptor (CAR); and a second nucleic acid sequence encoding a SHP-2 domain lacking a SHP-2 phosphatase domain, wherein the sequence of the SHP-2 domain is SEQ ID NO: 11 or SEQ ID NO; 12.

3. A vector, which comprises the nucleic acid construct according to claim 2.

4. The vector according to claim 3, which is a retroviral or lentiviral vector.

5. A pharmaceutical composition comprising a plurality of the isolated T cells according to claim 1.

* * * * *

UNITED STATES PATENT AND TRADEMARK OFFICE
CERTIFICATE OF CORRECTION

PATENT NO. : 11,345,734 B2
APPLICATION NO. : 15/577378
DATED : May 31, 2022
INVENTOR(S) : Martin Pulé et al.

It is certified that error appears in the above-identified patent and that said Letters Patent is hereby corrected as shown below:

On the Title Page

Item (57), Line 15, "(ii)" should be -- (iv) --.

In the Claims

At Column 159, Lines 5-6, "domain is SEQ ID NO: 11 or SEQ ID NO: 12." should be -- domain consists of the amino acid sequence as set forth in SEQ ID NO: 11, or the amino acid sequence as set forth in SEQ ID NO: 12. --.

At Column 159, Lines 11-12, "domain is SEQ ID NO: 11 or SEQ ID NO; 12." should be -- domain consists of the amino acid sequence as set forth in SEQ ID NO: 11, or the amino acid sequence as set forth in SEQ ID NO: 12. --.

At Column 159, Line 13, "vector," should be -- vector --.

Signed and Sealed this
Twenty-seventh Day of December, 2022

Katherine Kelly Vidal
*Director of the United States Patent and Trademark Office*